United States Patent
Kim et al.

(10) Patent No.: US 9,772,301 B2
(45) Date of Patent: Sep. 26, 2017

(54) METHOD FOR PRODUCING A SENSOR INCLUDING A CORE-SHELL NANOSTRUCTURE

(71) Applicant: INHA-INDUSTRY PARTNERSHIP INSTITUTE, Icheon (KR)

(72) Inventors: Sang Sub Kim, Gyeonggi-do (KR); Sun-Woo Choi, Gyeongsangbuk-do (KR); Akash Katoch, Icheon (KR)

(73) Assignee: INHA-INDUSTRY PARTNERSHIP INSTITUTE, Incheon (KR)

( * ) Notice: Subject to any disclaimer, the term of this patent is extended or adjusted under 35 U.S.C. 154(b) by 0 days.

(21) Appl. No.: 14/611,882

(22) Filed: Feb. 2, 2015

(65) Prior Publication Data

US 2015/0300980 A1    Oct. 22, 2015

Related U.S. Application Data

(63) Continuation of application No. PCT/KR2013/001198, filed on Feb. 15, 2013.

(30) Foreign Application Priority Data

Aug. 2, 2012  (KR) .................. 10-2012-0084858
Feb. 13, 2013  (KR) .................. 10-2013-0015359

(51) Int. Cl.
*G01N 27/414* (2006.01)
*H01L 29/06* (2006.01)
(Continued)

(52) U.S. Cl.
CPC .......... *G01N 27/4146* (2013.01); *B82Y 15/00* (2013.01); *B82Y 40/00* (2013.01);
(Continued)

(58) Field of Classification Search
CPC ............. H01L 29/0669; G01N 27/125–27/127
See application file for complete search history.

(56) References Cited

U.S. PATENT DOCUMENTS

| | | | | |
|---|---|---|---|---|
| 8,440,997 | B2 * | 5/2013 | Wang | B82Y 20/00 257/130 |
| 2011/0048538 | A1 | 3/2011 | Huang et al. | |
| 2015/0268207 | A1 * | 9/2015 | Motayed | G01N 33/0031 506/13 |

FOREIGN PATENT DOCUMENTS

| | | |
|---|---|---|
| KR | 1020100108983 A | 10/2010 |
| KR | 1020110074289 A | 6/2011 |

(Continued)

OTHER PUBLICATIONS

Na, Chan Woong, et al. "Selective detection of NO 2 and C 2 H 5 OH using a Co 3 O 4-decorated ZnO nanowire network sensor." Chemical Communications 47.18 (2011): 5148-5150.*

(Continued)

*Primary Examiner* — Victor A Mandala
*Assistant Examiner* — Regan J Rundio
(74) *Attorney, Agent, or Firm* — Sheridan Ross P.C.

(57) ABSTRACT

The present invention relates to a sensor including a core-shell nanostructure, and more particularly, to a sensor including: a base material; a sensing part including a core-shell nanostructure that has a core including a first metal oxide and a shell including a second metal oxide formed on the core; and two electrode layers spaced from each other on the sensing part.

1 Claim, 72 Drawing Sheets

(51) Int. Cl.
    *H01L 29/225*     (2006.01)
    *H01L 21/02*     (2006.01)
    *B82Y 15/00*     (2011.01)
    *B82Y 40/00*     (2011.01)
    *H01L 29/24*     (2006.01)
    *G01N 27/12*     (2006.01)

(52) U.S. Cl.
    CPC .. *H01L 21/02554* (2013.01); *H01L 21/02603* (2013.01); *H01L 29/0669* (2013.01); *H01L 29/0673* (2013.01); *H01L 29/24* (2013.01); *G01N 27/127* (2013.01); *H01L 29/225* (2013.01)

(56) References Cited

FOREIGN PATENT DOCUMENTS

| KR | 10-1091639 B1 | 12/2011 |
| KR | 10-2012-0059038 | 6/2012 |

OTHER PUBLICATIONS

Chen, Yu-Jin, et al. "Synthesis and enhanced ethanol sensing characteristics of α-Fe2O3/SnO2 core-shell nanorods." Nanotechnology 20.4 (2008): 045502.*

Qin Kuang, Chang-Shi Lao, Zhou Li, Yu-Zi Liu, Zhao-Xiong Xie, Lan-Sun Zheng, and Zhong Lin Wang. Enhancing the Photon- and Gas-Sensing Properties of a Single SnO2 Nanowire Based Nanodevice by Nanoparticle Surface Functionalization. J. Phys. Chem. C 2008, 112, 11539-11544.*

Tadatsugu Minami, Toshihiro Miyata, Takashi Yamamoto. Work function of transparent conducting multicomponent oxide thin films prepared by magnetron sputtering. Surface and Coatings Technology 108-109 (1998) 583-587.*

Mashock, Mark, et al. "Modulating gas sensing properties of CuO nanowires through creation of discrete nanosized p—n junctions on their surfaces." ACS applied materials & interfaces 4.8 (2012): 4192-4199.*

Hwang, In-Sung, et al. "Synthesis and gas sensing characteristics of highly crystalline ZnO—SnO 2 core-shell nanowires." Sensors and Actuators B: Chemical 148.2 (2010): 595-600.*

Pan, Ko-Ying, et al. "Synthesis of SnO 2-ZnO core-shell nanowires and their optoelectronic properties." Journal of Nanomaterials 2012 (2012): 6.*

Tharsika, T., et al. "Enhanced ethanol gas sensing properties of SnO2-core/ZnO-shell nanostructures." Sensors 14.8 (2014): 14586-14600.*

Choi, Sun-Woo, et al. "Striking sensing improvement of n-type oxide nanowires by electronic sensitization based on work function difference." Journal of Materials Chemistry C 3.7 (2015): 1521-1527.*

Huang, Hui, et al. "Low-temperature growth of SnO2 nanorod arrays and tunable n-p-n sensing response of a ZnO/SnO2 heterojunction for exclusive hydrogen sensors." Advanced Functional Materials 21.14 (2011): 2680-2686.*

Chen, Jiajun, Kai Wang, and Weilie Zhou. "Vertically Aligned ZnO Nanorod Arrays Coated with SnO2/Noble Metal Nanoparticles for Highly Sensitive and Selective Gas Detection." IEEE Transactions on Nanotechnology 10.5 (2011): 968-974.*

Yu, Ji Haeng, and Gyeong Man Choi. "Electrical and CO gas-sensing properties of ZnO/SnO 2 hetero-contact." Sensors and Actuators B: Chemical 61.1 (1999): 59-67.*

Chen et al. "Synthesis and enhanced ethanol sensing characteristics of α-Fe2O3/SnO2 core—shell nanorods," Nanotechnology, Jan. 2009, vol. 20, No. 4, 6 pages.

Choi et al. "Synthesis of SnO2—ZnO core—shell nanofibers via a novel two-step process and their gas sensing properties," Nanotechnology, Nov. 2009, vol. 20, No. 46, 6 pages.

International Search Report prepared by the Korean Patent Office on May 2, 2013, for International Application No. PCT/KR2013/001198.

Gim, Sang Seop: "Development of Highly Sensitive Nanosensors Anchored with Metal Nanoparticles by γ-ray Irradiation for Detecting Toxic Gases", Ministry of Eduction, Science and Technology report, Sep. 2010; pp. 27, 28 and figure 7.

* cited by examiner

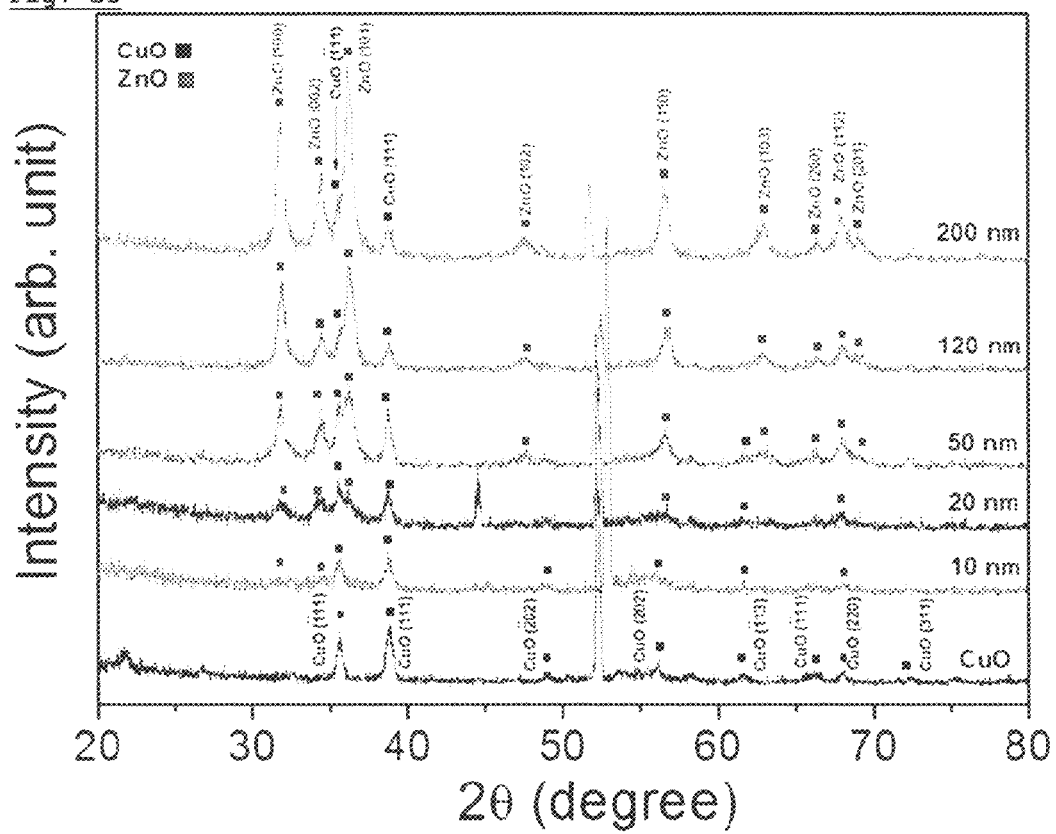

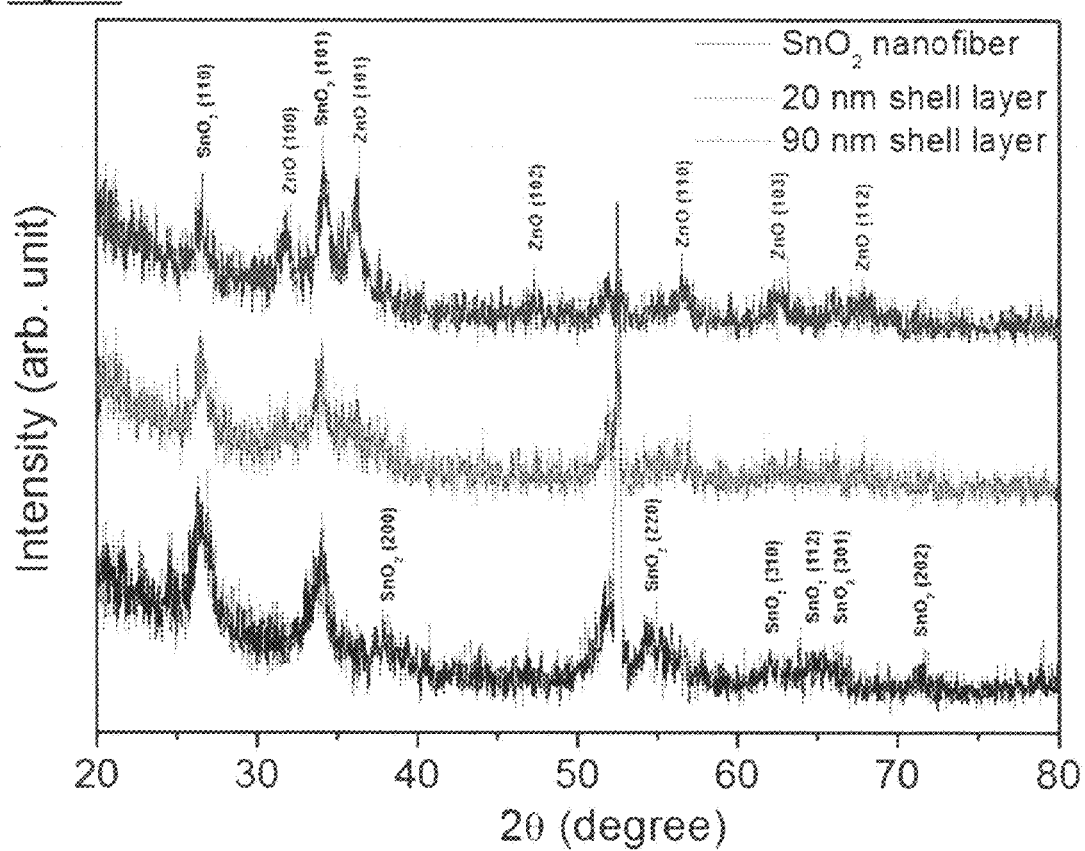

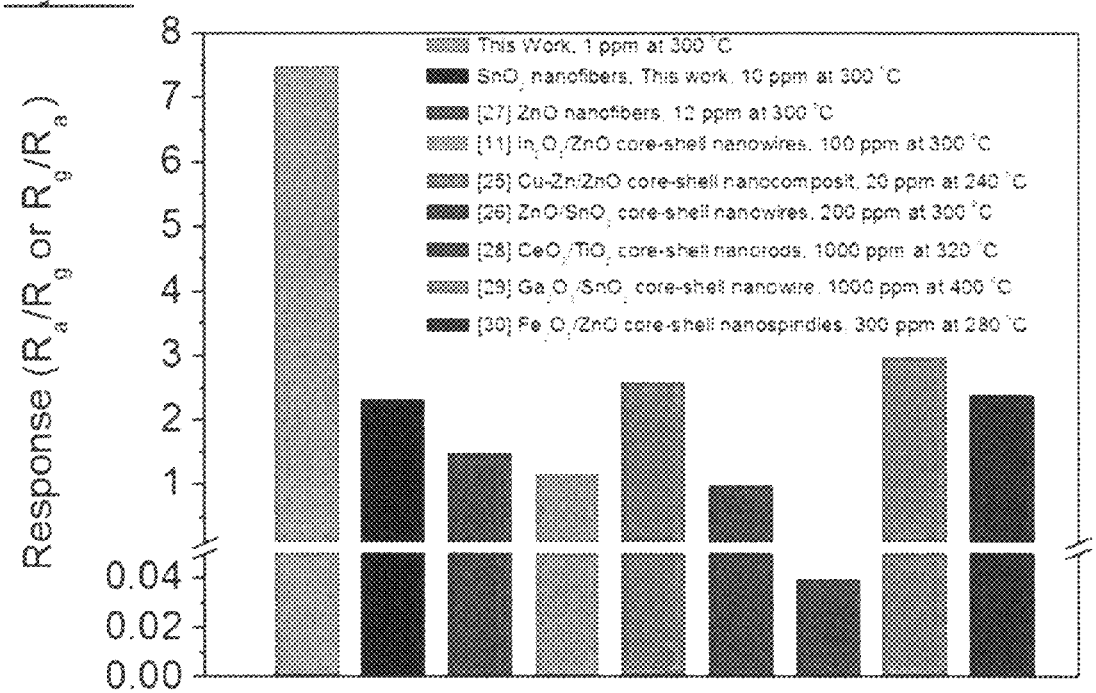

METHOD FOR PRODUCING A SENSOR INCLUDING A CORE-SHELL NANOSTRUCTURE

CROSS-REFERENCE TO RELATED APPLICATIONS

This application is a continuation of International Application No. PCT/KR2013/001198, filed Feb. 15, 2013, which PCT application designates the United States and claims the benefit of Korean Application No. 10-2012-0084858, filed Aug. 2, 2012, and Korean Application No. 10-2013-0015359, filed Feb. 13, 2013, the entire disclosures of each of which are incorporated by reference herein.

TECHNICAL FIELD

The present disclosure invention relates to an sensor including: a base material; a sensing part including a core-shell nanostructure that has a core including a first metal oxide formed on the base material, and a shell including a second metal oxide formed on the core; and two electrode layers spaced apart from each other on the sensing part.

BACKGROUND ART

A chemical sensor is a sensor using, as a sensing principle, a density change of conduction electrons on a surface of a semiconductor material, which is caused by a chemical interaction between a chemical species to be sensed and the surface of the semiconductor material disposed on a sensing part, and an electrical resistivity change of the semiconductor material, which is induced by the density change. For example, in case that the semiconductor material disposed on the sensing part is a metal oxide, when a chemical species to be sensed is attached to a surface of the metal oxide, an oxidation-reduction reaction occurs on the surface of the metal oxide to change the electrical resistivity of the metal oxide, so that the chemical species may be sensed through the electrical resistivity change.

Recently, studies on nano chemical sensors using metal oxides having nanostructures, such as a nanowire, a nanotube, and a nanoribbon, as a semiconductor material included in the sensing part of the chemical sensor, are being actively conducted. This is because the nano chemical sensor using the nano structured metal oxide has a high surface area to volume ratio compared to an existing chemical sensor in which a bulk or thin film semiconductor material is included in the sensing part, and thus is expected to have a higher sensitivity. For example, a study on a nano chemical sensor in which a nanostructure, which is prepared by using a photolithography process, is included in the sensing part, has been reported. Also, for example, Korea Patent No. 1027074 entitled "NANOSTRUCTURE GAS SENSORS AND NANOSTRUCTURE GAS SENSOR ARRAY WITH METAL OXIDE LAYER AND METHOD OF PRODUCING THE SAME" discloses a high sensitive nano chemical sensor in which a nanostructured metal oxide is included in a sensing part.

If a high sensitive chemical sensor, which has an excellent sensitivity to detect an infinitesimal gas, is developed, the high sensitive chemical sensor may be applicable to a national defense and a special purpose as well as various industrial fields, thereby playing a role in creating safer communities. Especially, since a reducing gas including various volatile organic compounds (VOC) is considerably harmful to the human body, and has a high risk of explosion, in case that a high sensitive nano chemical sensor is developed and thus, it is possible to preemptively detect an infinitesimal amount of a reducing gas, the high sensitive nano chemical sensor is expected to be very useful. If a kind of reducing gas, for example, CO is inhaled, since the CO forms carboxy-hemoglobin in blood to disturb an oxygen transfer and reduce an gas exchange performance of red blood cells to cause a death, it is required to detect an infinitesimal amount of CO in a ppm level to hundreds ppm level. However, a high sensitive nano chemical sensor, which is sufficiently sensitive to the reducing gas, was not studied or reported before.

DISCLOSURE OF THE INVENTION

Technical Problem

One object of the present invention is to provide a sensor including a core-shell nanostructure, and a method for preparing the same.

Technical Solution

In order to achieve the objects, the present invention provides a sensor including: a base material; a sensing part including a core-shell nanostructure that has a core including a first metal oxide and a shell including a second metal oxide formed on the core; and two electrode layers spaced from each other on the sensing part.

The present invention also provides a sensor including: a base material; two electrode layers spaced apart from each other on the base material; a sensing part including a core-shell nanostructure that has a core including a first metal oxide formed on the electrode and a shell including a second metal oxide formed on the core.

Advantageous Effects

A sensor according to the present invention may include, as a sensing material, a nanowire including discrete nano islands formed on a surface thereof, and through this, a modulation of a conduction channel of a nanowire core may be maximized, so that the sensor may sense an infinitesimal amount of a gas. Also, through a combination using a transfer of conduction carriers by a p-n junction, and a combination using a transfer of conduction carriers by to a work function difference, the sensor may sense an infinitesimal amount of an oxidizing gas or a reducing gas.

Further, since a shell thickness is adjusted to a value equal to or less than a Debye length to form a fully depleted layer, the sensor of the present invention may be usefully used in various fields as a sensor having an especially excellent sensitivity in detecting an infinitesimal amount of a reducing gas. If a reducing gas, for example, CO is inhaled, the CO may disturb an oxygen transfer due to high adsorptive power thereof to carboxy-hemoglobin to cause a death. However, since an infinitesimal amount of the reducing gas may be detected with a high sensitivity by using the sensor including the core-shell nanostructure of the present invention, such a danger may be prevented. Meanwhile, in the sensor of the present invention, the core-shell structure may be prepared, for example, by forming a core having a networked shape of nanowires through an electro spinning method, and performing several times of atomic layer deposition to form the shell on the core, and since the electrospinning method and the atomic layer deposition are very simple methods, the cost and time taken to produce the sensor may be reduced.

Also, when the shell is formed by using the atomic layer deposition, since the performed number of the atomic layer deposition tends to be in linear proportion to the shell thickness, the performed number of the atomic layer deposition may be adjusted by using the linear proportion relation to form a desired shell thickness, and accordingly, the shell thickness may be adjusted to a value equal to or less than a Debye length to improve a sensitivity of the sensor with a reducing gas.

Further, since a core-shell nanostructure included in the sensing part of the sensor according to the present invention is a species of a nanostructure and has a surface area to volume ratio, a wider area thereof may be exposed to a gas to be sensed, especially, when the core-shell nanostructure has a networked structure of nanowires, a large area deposition is additionally possible at room temperature, and also, since the core-shell nanostructure has a nanoscale, the formation of an ultrathin and ultralight element is possible.

Furthermore, since the core-shell nanostructure included in the sensing part of the sensor of the present invention includes the core and the shell having different compounds to allow a heterojunction to be formed on an interface between the core and the shell, the sensor may be prepared so as to have a sensitivity higher than that of a nanostructure formed of a single material or a nanostructure of an alloy.

BRIEF DESCRIPTION OF THE DRAWINGS

FIG. 33 is an X-ray θ-2θ diffraction pattern (XRD pattern) of each of a CuO—ZnO core-shell nanowire prepared so as to have various thicknesses according to Specific Example 1 of the present invention, and a comparison group of a CuO nanowire;

FIG. 38 shows an X-ray θ-2θ diffraction pattern (XRD pattern) of each of a $SnO_2$—ZnO core-shell nanowire prepared so as to have various thicknesses according to Specific Example 1 of the present invention, and a comparison group of a CuO nano wire;

FIG. 39F expresses the results of FIGS. 39A to 39D in one graph;

MODE FOR CARRYING OUT THE INVENTION

Figure 1A:
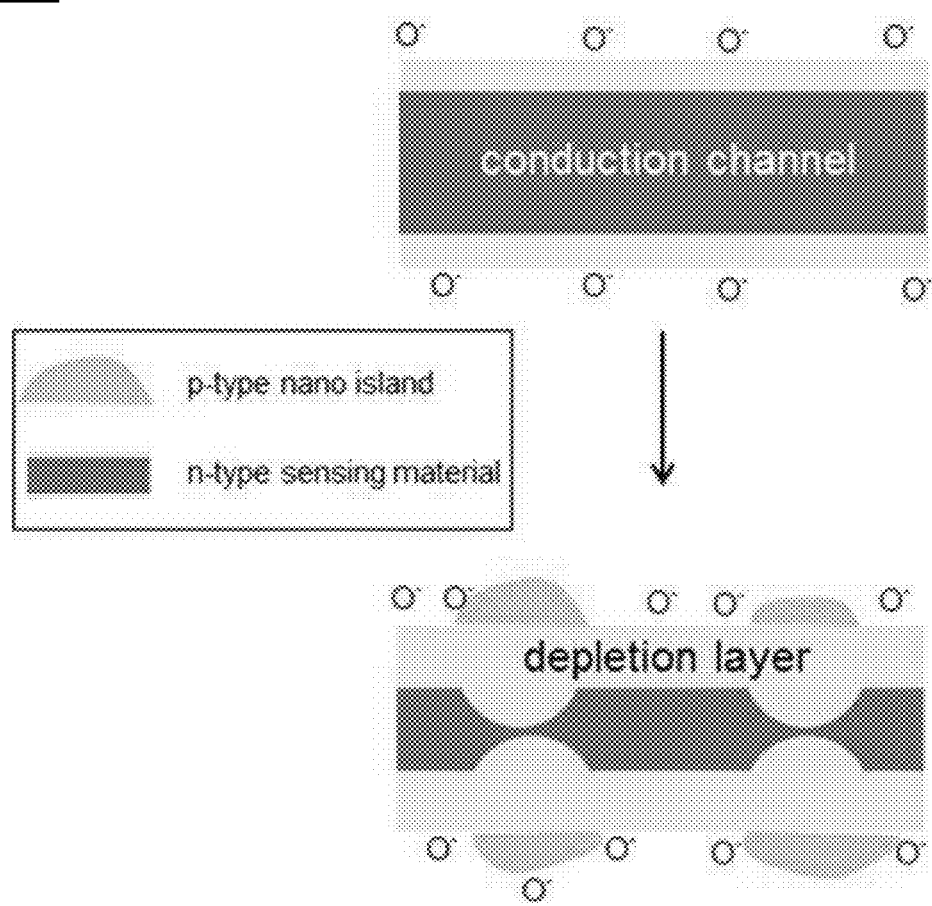
FIG. 1A is a view illustrating a conduction channel variation of a sensor according to an embodiment of the present invention.

Hereinafter, embodiments of the present invention will be described with reference to the accompanying drawings in such a manner that it may easily be carried out by a person with ordinary skill in the art to which the present invention pertains. The present invention may, however, be embodied in different forms and should not be construed as limited to the embodiments set forth herein. In order to clarify the present invention, parts not related to the description are omitted from the drawings, and the same reference numbers are used throughout the drawings to refer to the same or like parts.

Throughout the description, when one part (or element, device, etc.) is referred to as being 'connected' to another part (or element, device, etc.), it should be understood that the former can be 'directly connected' to the latter, or 'electrically connected' to the latter via an intervening part (or element, device, etc.).

Throughout the description, when one element is referred to as being "on" another element, it should be understood that the former can contact the latter, or intervening layers may be also be present.

Throughout the description, when it is said that a part "includes" an element, it means that the part may further include other elements unless otherwise described. The terms of degree, such as "about (approximately)", "Substantially", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention. The term of degree "step (doing) -" or "step of -" used herein does not refer to "the step for -". Throughout the description, the term "combination thereof" included in the Markush type expressions refers to a mix or combination of one or more selected from the group consisting of constituent elements described in the Markush type expression, and refers to including one or more selected from the group consisting of the above-described constituent elements.

Throughout the description, the term "Debye length" refers to the distance that a negative particle, i.e., a free electron given inside plasma is shielded by positive particles around the free electron and thus is movable by kinetic energy thereof regardless of an outside, but is not limited thereto. Alternatively, the term "Debye length" refers to the distance that a charge disappears, and for example, may refer to a minimum distance that an electron is movable due to adsorption of oxygen when oxygen is adsorbed on a surface of an n-type shell and electrons, i.e., charge carriers of an n-type oxide semiconductor move toward the adsorbed oxygen and disappear from the surface of the n-type shell, but is not limited thereto. For example, the Debye length of a shell material may be varied with inherent properties such as a dielectric constant of the shell material and the like, and the height of a potential barrier generated according to a bending phenomenon of the band from a heterojunction between the shell material and a core material, but is not limited thereto.

Also, throughout the specification, the term "depletion layer" refers to a space where a charge carrier is depleted, for example, a space where in case of a p-type semiconductor, a hole, i.e., a charge carrier is depleted, or in case of an n-type oxide semiconductor, an electron, i.e., a charge carrier is depleted, but is not limited thereto. Also, throughout the specification, the term "fully depleted layer" may refer to a space where charge carriers are fully depleted, but is not limited thereto.

The term "reducing gas" as used herein refers to a gas that accelerates a reduction reaction of a material reacting with the gas and does not easily cause an oxidation reaction, and the "reduction" in the reducing gas may refer to "losing oxygen", "obtaining hydrogen", or "obtaining electrons", but is not limited thereto.

Throughout the specification, the term "core-shell nanostructure" generally refers to nanostructures having a core-shell nanostructure, and for example, may include a nanostructure in which a nanowire is formed as a core, and a shell surrounds an outer surface of the nanowire. At this time, the "core-shell nanostructure" may include a structure in which the shell fully surrounds the outer surface of the nanowire, or and discretely surrounds the outer surface of the nanowire.

The present invention provides a sensor including:
a base material;
a sensing part including a core-shell nanostructure that has a core including a first metal oxide formed on the base material, and a shell including a second metal oxide formed on the core; and
two electrode layers spaced apart from each other on the sensing part.

Also, the present invention provides a sensor including:
a base material;
two electrode layers spaced apart from each other on the base material; and a sensing part including core-shell nanostructure that has a core including a first metal oxide formed on the electrode layer, and a shell including a second metal oxide formed on the core.

At this time, in the sensor according to the present invention, the core may be an oxide semiconductor nanowire, and the shell may be oxide semiconductor nano islands that are discretely attached to a surface of the oxide semiconductor nanowire, wherein the nanowire and the nano islands may respectively be:

1) an n-type oxide semiconductor nanowire and p-type oxide semiconductor nano islands;

2) a p-type oxide semiconductor nanowire and n-type oxide semiconductor nano islands;

3) an n-type oxide semiconductor nanowire and n-type oxide semiconductor nano islands, in which an n-type oxide semiconductor of the nano islands and an n-type oxide semiconductor of the nanowire may have different work functions from each other.

At this time, in the sensor according to the present invention, the nanowire generally refers to nanostructures that have one-dimensional structure and include a nanoline, a nanoneedle, a nanotube, and a nanobelt.

Hereinafter, the sensor in which the core is an oxide semiconductor nanowire and the shell is oxide semiconductor nano islands that are attached to a surface of the oxide semiconductor nanowire as described above, will be described in detail.

The sensor according to the present invention includes, as gas sensing materials, an oxide semiconductor nanowire, and oxide semiconductor nano islands that are discretely attached to a surface of the nanowire.

That is, the sensor according to the present invention is a sensor using, as a gas sensing material, an oxide semiconductor nanowire including discrete nano islands formed on a surface thereof in order to show excellent sensor characteristics such as high sensitivity, short response time, recovery time and the like, and may detect an infinitesimal amount of a chemical gas by discretely forming the oxide semiconductor nano islands on the surface of the oxide semiconductor nanowire having fundamentally excellent sensing characteristics.

At this time, in the sensor according to the present invention, the nanowire and the nano islands may be:

1) an n-type oxide semiconductor nanowire and p-type oxide semiconductor nano islands;

2) a p-type oxide semiconductor nanowire and n-type oxide semiconductor nano islands;

3) an n-type oxide semiconductor nanowire and n-type oxide semiconductor nano islands, in which an n-type oxide semiconductor of the nano islands and an n-type oxide semiconductor of the nanowire may have different work functions from each other.

Hereinafter, respective cases that the nanowire and the nano islands are 1), 2), and 3) will be described.

Figure 1B:
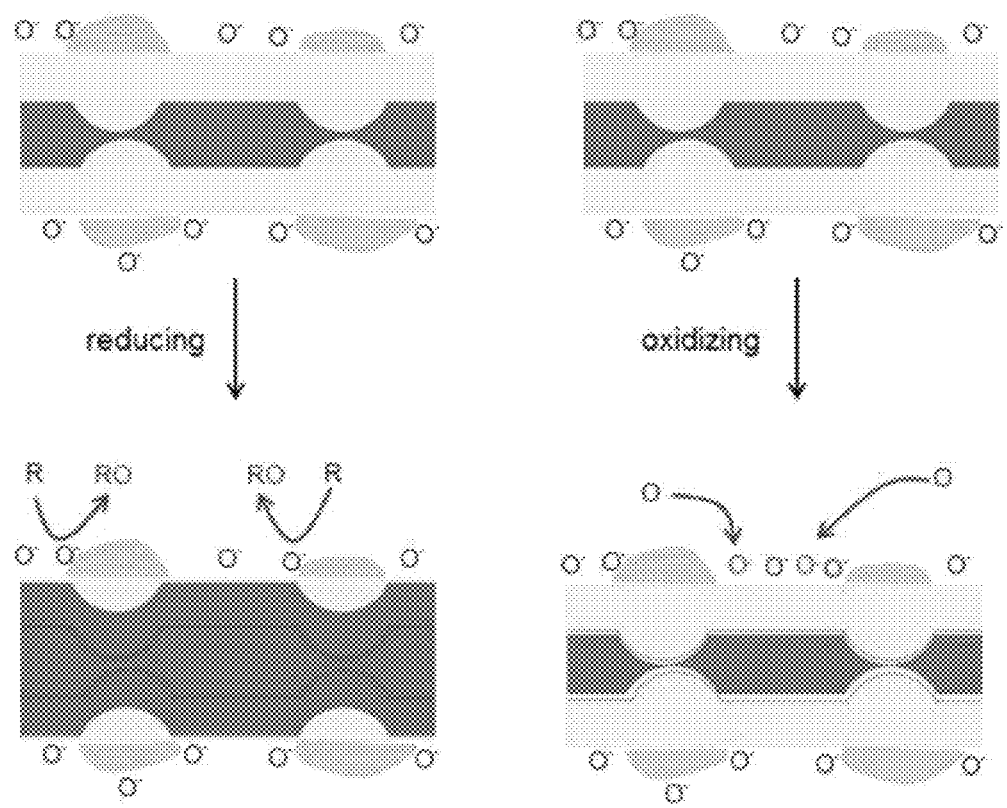
FIG. 1B is a view illustrating a conduction channel variation of a sensor according to an embodiment of the present invention.

1) Case that the Nanowire and the Nano Islands are an n-Type Oxide Semiconductor Nanowire and p-Type Oxide Semiconductor Nano Islands, Respectively As described above, the nanowire and the nano islands of the sensor according to the present invention may be an n-type oxide semiconductor nanowire and p-type oxide semiconductor nano islands, respectively, and are schematically illustrated through FIGS. 1A and 1B.

As illustrated in FIG. 1A, in a combination of p-type oxide semiconductor nano islands and an n-type oxide semiconductor nanowire, a catalyst effect of the nano islands, and an electron transfer between the nano island and the nanowire take place in a direction from the n-type nanowire to the p-type nano islands, and accordingly, a conduction channel of the nanowire, which is reduced by adsorption of oxygen in the atmosphere, is further reduced.

At this time, as illustrated in FIG. 1B, it may be seen that resistance of the nanowire that is a gas sensing material, increases to a very high value due to a reduction of conduction channel according to a formation of the nano islands, and a resistance change with respect to a reducing gas is much greater than a resistance change with respect to an oxidizing gas due to structural limitations (such as a size and shape of the nanowire) of the nanowire.

Therefore, when the nanowire and the nano islands of the sensor according to the present invention are an n-type oxide semiconductor nanowire and p-type oxide nano islands, respectively as described above, an infinitesimal amount of a reducing gas may be more easily sensed.

At this time, $ZnO$, $SnO_2$, $In_2O_3$, $WO_3$, $Fe_2O_3$, $TiO_2$ or the like may be used as the n-type oxide semiconductor. However, the n-type oxide semiconductor is not limited thereto, but an oxide semiconductor, which is usable as a gas sensing material, may be appropriately selected to be used as the n-type oxide semiconductor.

Also, $Co_3O_4$, $CoO$, $NiO$, $Ni_2O_3$, $MnO_2$, $Mn_3O_4$, $CuO$, $Cr_2O_3$, $Bi_2O_3$ or the like may be used as the p-type oxide semiconductor. However, the p-type oxide semiconductor is not limited thereto, but an oxide semiconductor, which is usable as a gas sensor, may be appropriately selected to be used as the p-type oxide semiconductor.

It is preferable that the nanowire and the nano islands of the sensor according to the present invention use $SnO_2$ as the n-type oxide semiconductor nanowire and $Cr_2O_3$ as the p-type oxide nano islands, respectively. When the nanowire and the nano islands of the sensor according to the present invention are formed in a combination of $SnO_2$ and $Cr_2O_3$, the sensor may sense reducing gases, such as hydrogen ($H_2$) and carbon monoxide (CO) with a more excellent sensitivity.

Meanwhile, it is preferable that the nanowire have a diameter of 20 nm to 100 nm and the nano islands have a diameter of 10 nm to 30 nm.

When the diameter of the nanowire is less than the lower limit of the range, the maximization of the modulation effect of the nanowire conduction channel may not be expected, and when the diameter of the nano island exceeds the upper limit of the range, the nano islands contact each other to cause a resistance loss of the sensor element, so that the sensor may be vulnerable to detection of an infinitesimal amount of a gas.

In the sensor according to the present invention, the sum of areas occupied by the nano islands with respect to an entire surface area of the nanowire (the sum of the areas occupied by the nano islands/the entire surface area of the nanowire) may be preferably in a range of 0.2 to 0.5, and more preferably, be in a range of 0.4 to 0.5. When the ratio of the areas does not meet the range, gas sensing performance may be lowered.

Figure 2A:
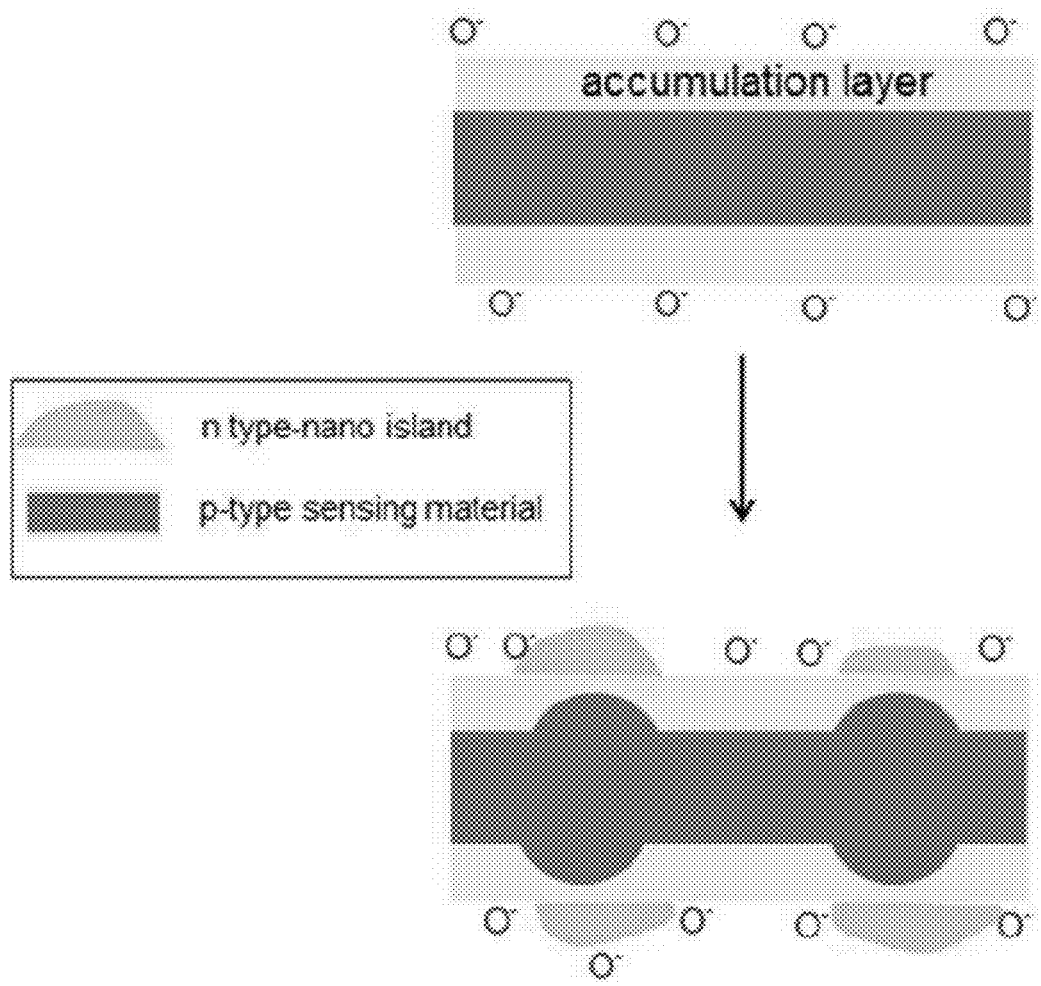
FIG. 2A is a view illustrating a conduction channel variation of a sensor according to another embodiment of the present invention.
Figure 2B:
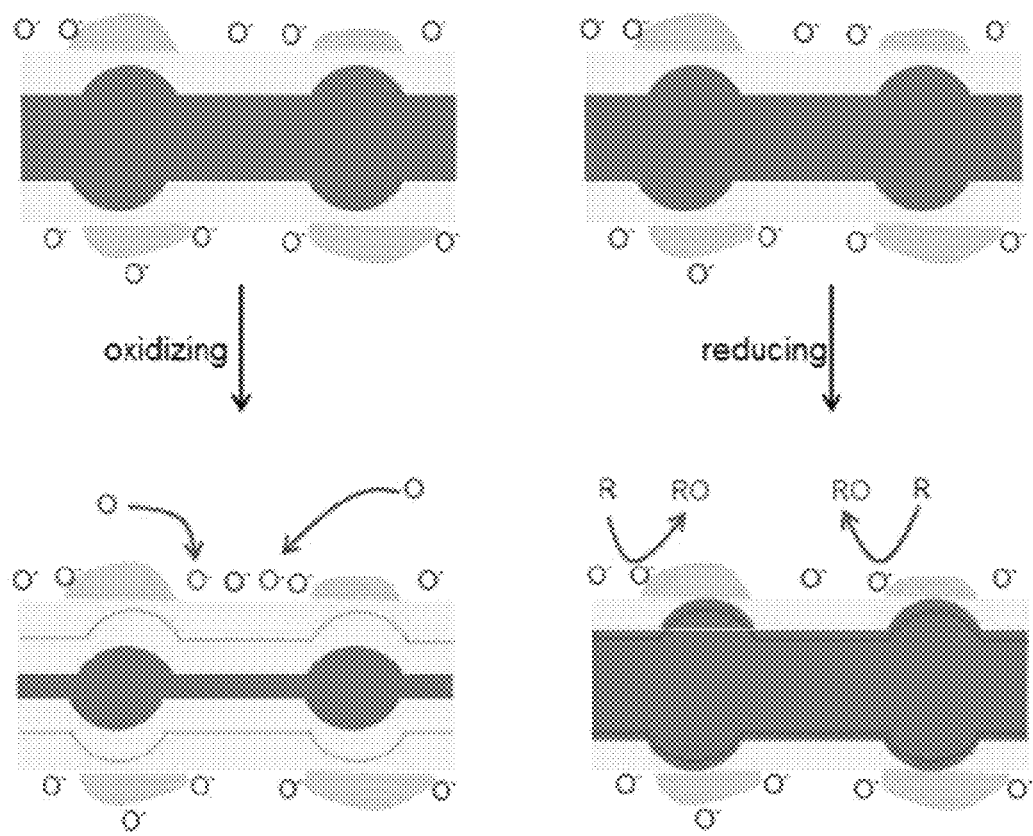
FIG. 2B is a view illustrating a conduction channel variation of a sensor according to another embodiment of the present invention.

2) Case that the Nanowire and the Nano Islands are a p-Type Oxide Semiconductor Nanowire and n-Type Oxide Semiconductor Nano Islands, Respectively As described above, the nanowire and the nano islands of the sensor according to the present invention may be a p-type oxide semiconductor nanowire and n-type oxide semiconductor nano islands, respectively, and are schematically illustrated in FIGS. 2A and 2B.

When a p-type oxide semiconductor nanowire is used, the resistance of the nanowire is changed by holes that are majority charges, differently from an n-type oxide semiconductor nanowire, and accordingly, a conduction channel variation according to gas adsorption occurs by a charge (hole) accumulation layer formed on a portion near a surface of the nanowire other than a center of the nanowire.

That is, as illustrated in FIG. 2A, in a combination of the n-type oxide semiconductor nano islands and the p-type oxide semiconductor nanowire, since an electron transfer takes place from the nano islands to the nanowire, a hole accumulation layer around a surface of the nanowire is decreased, and accordingly, the resistance of the nanowire that is a gas sensing material, increases to a high value.

At this time, as illustrated in FIG. 2B, when the nanowire that is the gas sensing material, is exposed to a reducing gas, the hole accumulation layer is further decreased, and since the diameter of the nanowire is limited, a change of the hole accumulation layer is also limited and accordingly, a resistance change of a sensor material is decreased. On the other hand, when the nanowire that is the gas sensing material, is exposed to an oxidizing gas, it may be seen that since a change of the hole accumulation layer is relatively large, a resistance change will become much larger. Therefore, as described above, when the nanowire and the nano islands of the sensor according to the present invention are the p-type oxide semiconductor nanowire and the n-type oxide semiconductor nano islands, the sensor may more easily sense an infinitesimal amount of an oxidizing gas.

At this time, $ZnO$, $SnO_2$, $In_2O_3$, $WO_3$, $Fe_2O_3$, $TiO_2$ or the like may be used as the n-type oxide semiconductor. However, the n-type oxide semiconductor is not limited thereto, but an oxide semiconductor, which is usable as a gas sensing material, may be appropriately selected to be used as the n-type oxide semiconductor.

Also, $Co_3O_4$, $CoO$, $NiO$, $Ni_2O_3$, $MnO_2$, $Mn_3O_4$, $CuO$, $Cr_2O_3$, $Bi_2O_3$ or the like may be used as the p-type oxide semiconductor. However, the p-type oxide semiconductor is not limited thereto, but an oxide semiconductor, which is usable as a gas sensing material, may be appropriately selected to be used as the p-type oxide semiconductor Meanwhile, it is preferable that the nanowire have a diameter of 20 nm to 100 nm, and the nano islands have a diameter of 10 nm to 30 nm.

When the diameter of the nanowire is less than the lower limit of the range, the maximization of the modulation effect of the nanowire conduction channel may not be expected, and when the diameter of the nano islands exceeds the upper limit of the range, the nano islands contact each other to cause a resistance loss of the sensor element, so that the sensor may be vulnerable to detection of an infinitesimal amount of a gas.

In the sensor according to the present invention, the sum of areas occupied by the nano islands with respect to an entire surface area of the nanowire (the sum of the areas occupied by the nano islands/the entire surface area of the nanowire) may be preferably in a range of 0.2 to 0.5, and more preferably, be in a range of 0.4 to 0.5. When the ratio of the areas does not meet the range, gas sensing performance may be lowered.

3) Case that the Nanowire and the Nano Islands are a n-Type Oxide Semiconductor Nanowire and n-Type Oxide Semiconductor Nano Islands, Respectively, and the n-Type Oxide Semiconductor Nanowire and the n-Type Oxide Semiconductor Nano Islands have Different Work Functions from Each Other As described above, the nanowire and the nano islands of the sensor according to the present invention may be an n-type oxide semiconductor nanowire and n-type oxide semiconductor nano islands, in which the n-type oxide semiconductor nanowire and the n-type oxide semiconductor nano islands may be configured to have different work functions from each other.

Like this, the case that the nano islands and the nanowire have different work functions from each other may be:

(1) a case that a work function of the nano islands is greater than that of the nanowire; or (2) a case that a work function of the nanowire is greater than that of the nano islands.

Like this, even when work functions of the nano islands and the nanowire are different from each other, an electron transfer takes place. That is, an electron transfer not according to a p-n junction but according to a work function difference between semiconductor nano islands and a semiconductor nanowire, and a catalyst effect of the nano islands may be used at the same time.

Figure 3A:
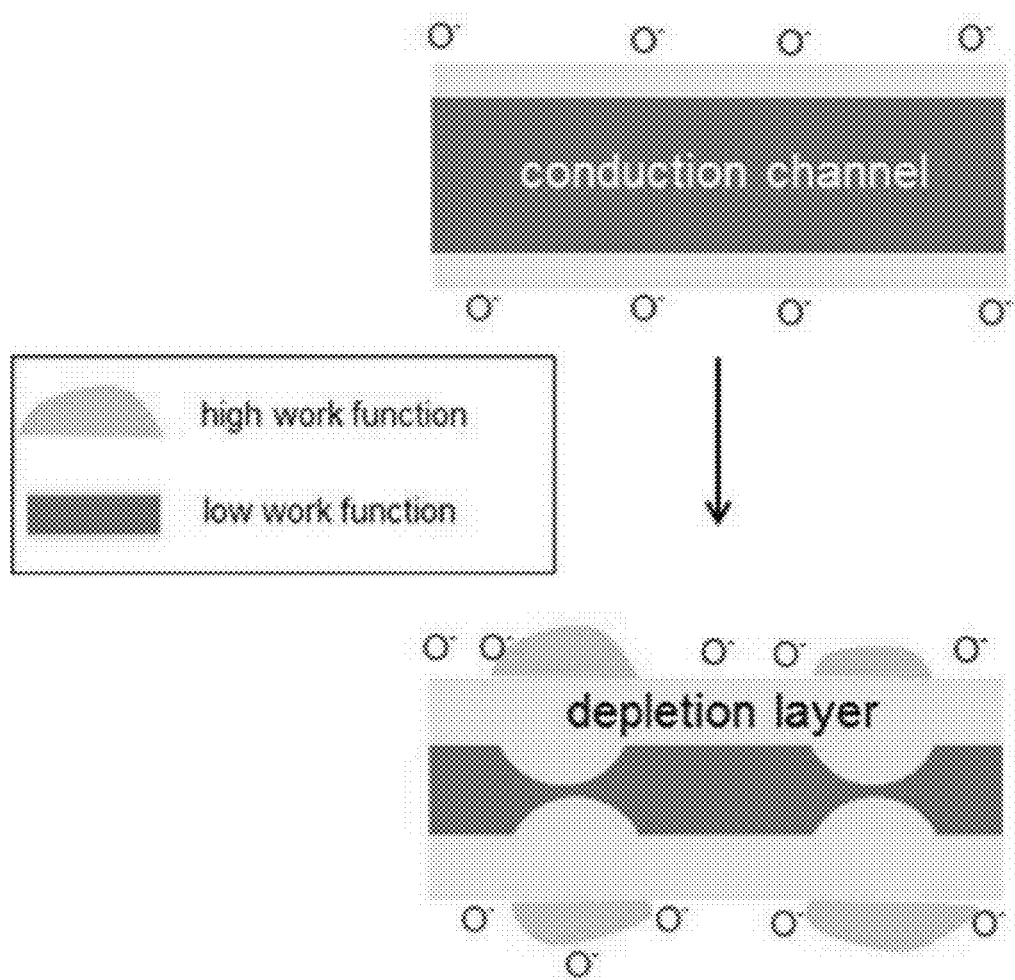
FIG. 3A is a view illustrating a conduction channel variation of a sensor according to another embodiment of the present invention.
Figure 3B:
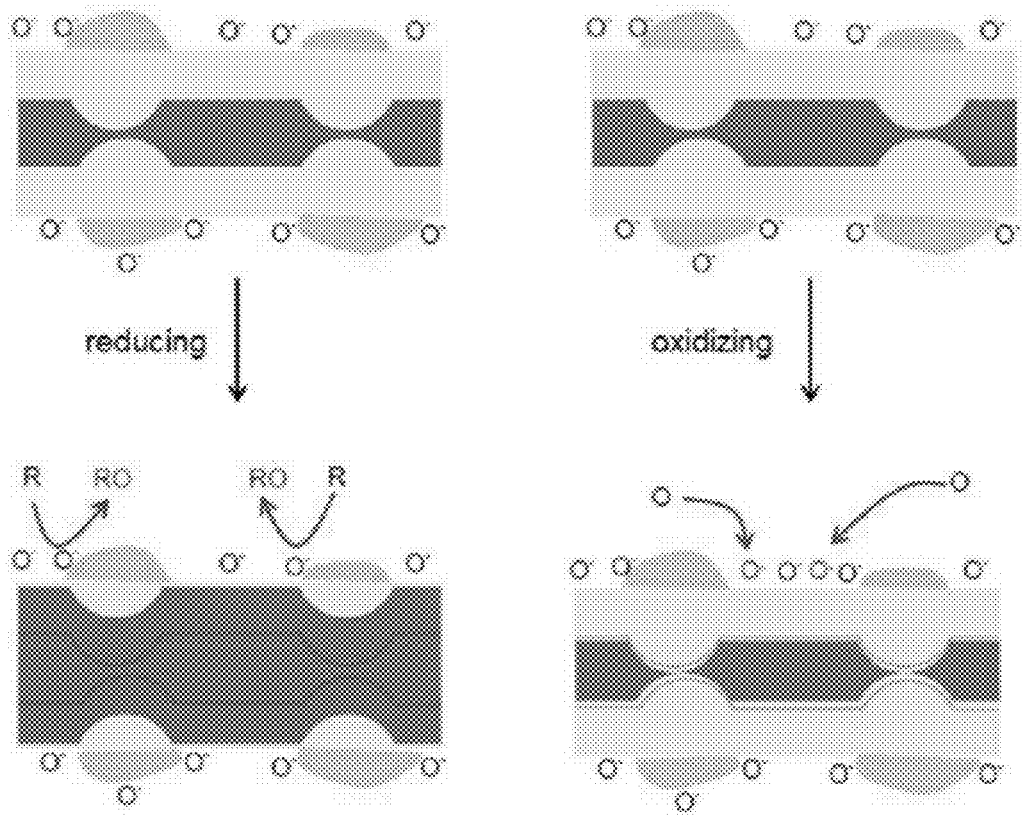
FIG. 3B is a view illustrating a conduction channel variation of a sensor according to another embodiment of the present invention.
Figure 4A:
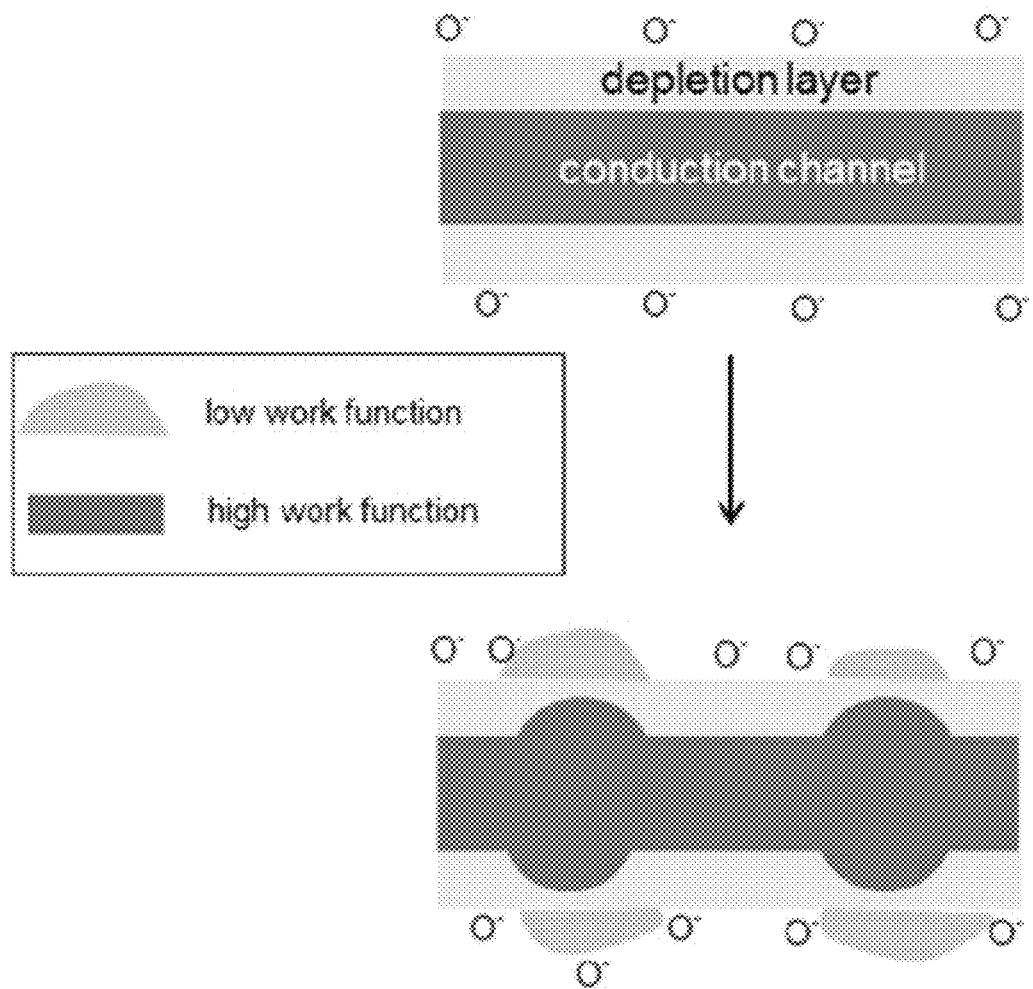
FIG. 4A is a view illustrating a conduction channel variation of a sensor according to another embodiment of the present invention.
Figure 4B:
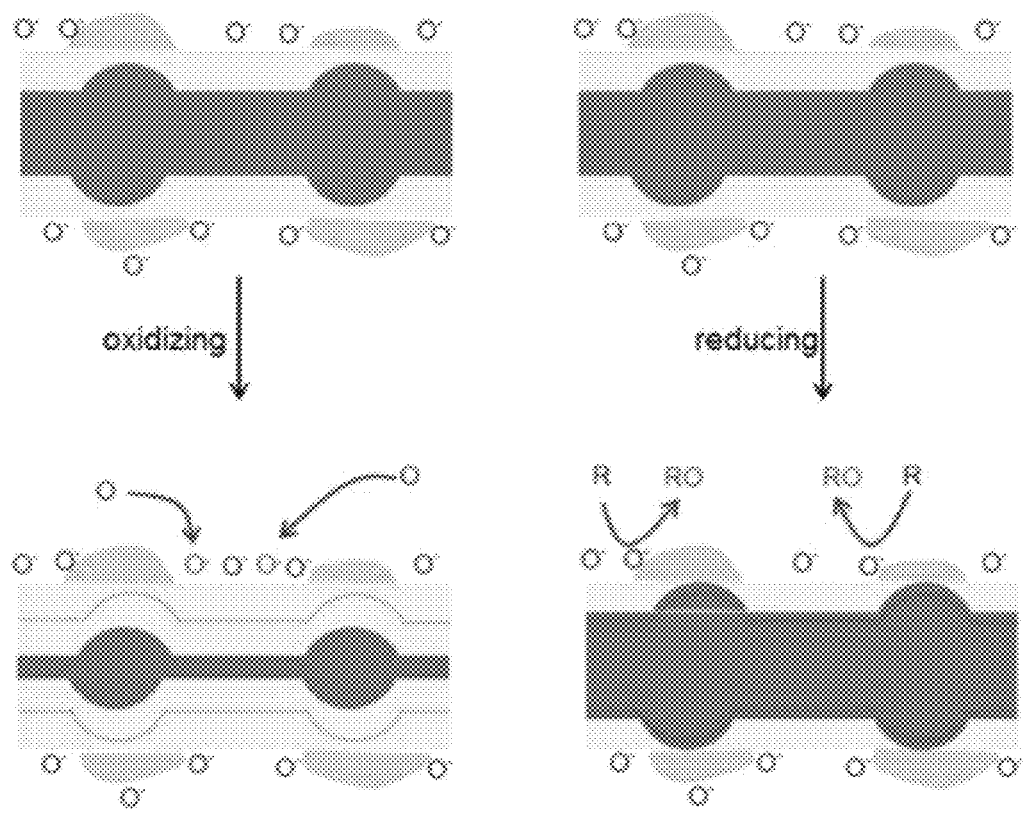
FIG. 4B is a view illustrating a conduction channel variation of a sensor according to another embodiment of the present invention.
Figure 5:
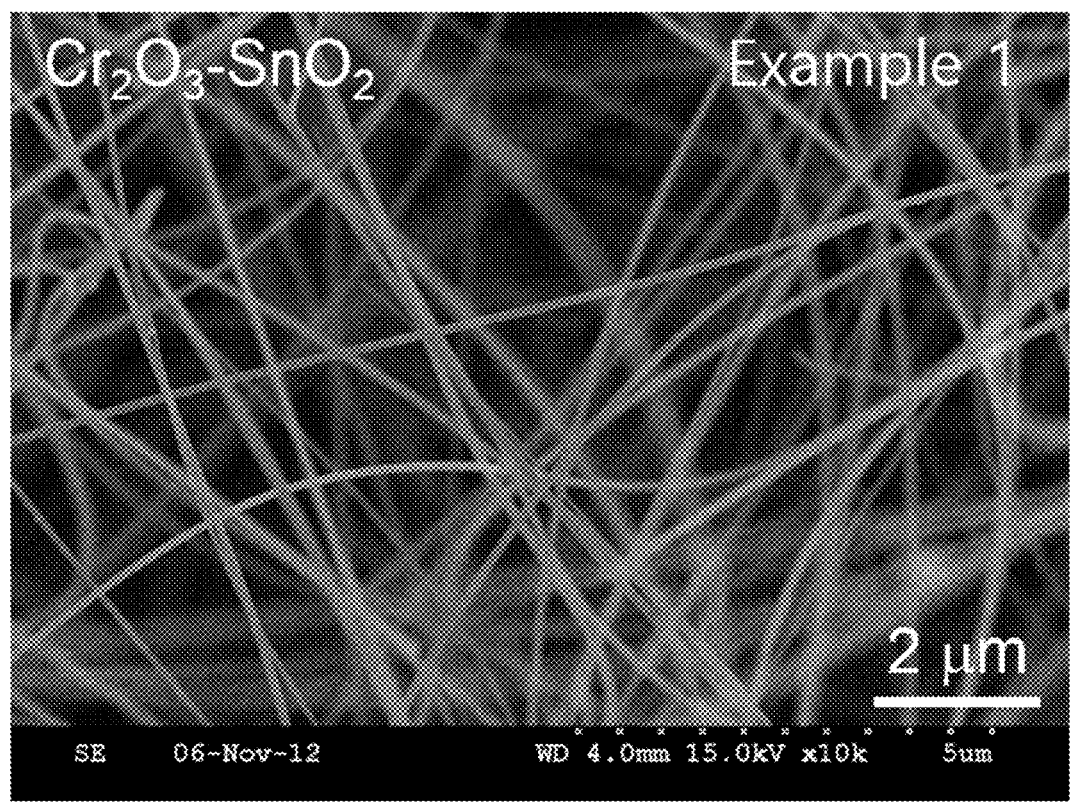
FIG. 5 is a field-emission scanning electron microscope image of a gas sensor prepared in Example 1 according to the present invention.
Figure 6:
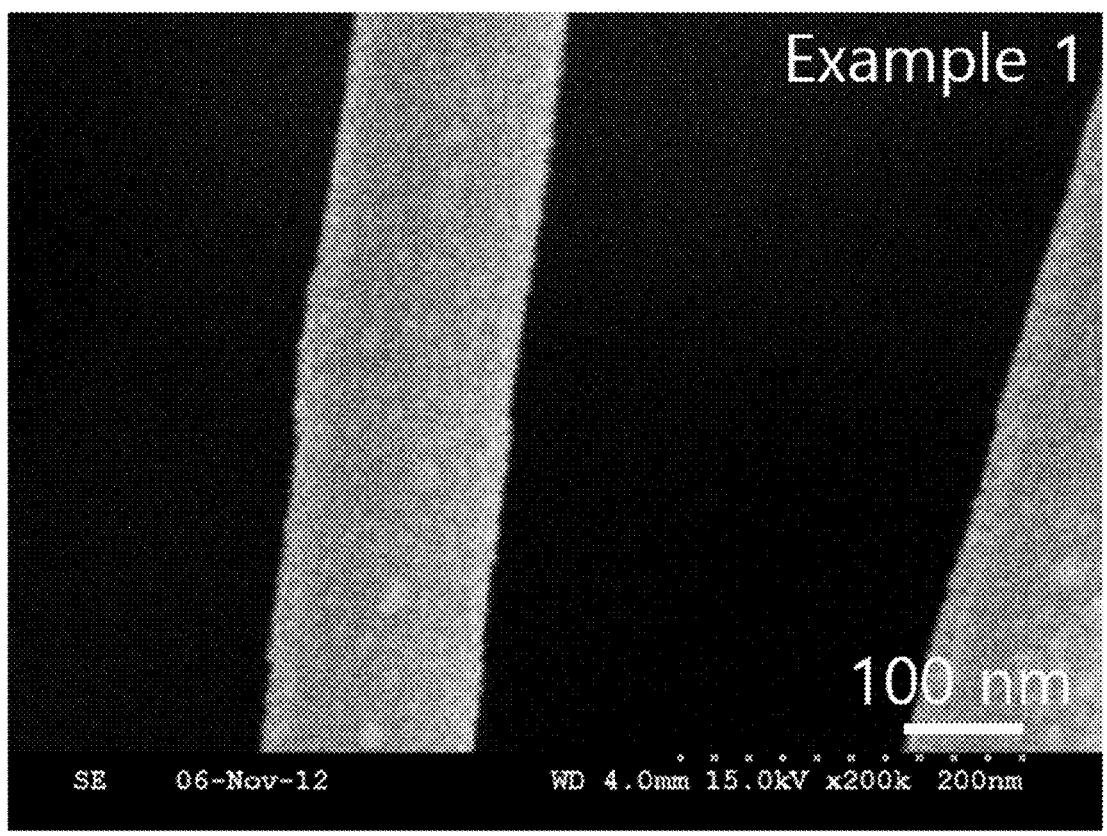
FIG. 6 is a field-emission scanning electron microscope image of a gas sensor prepared in Example 1 according to the present invention.
Figure 7:
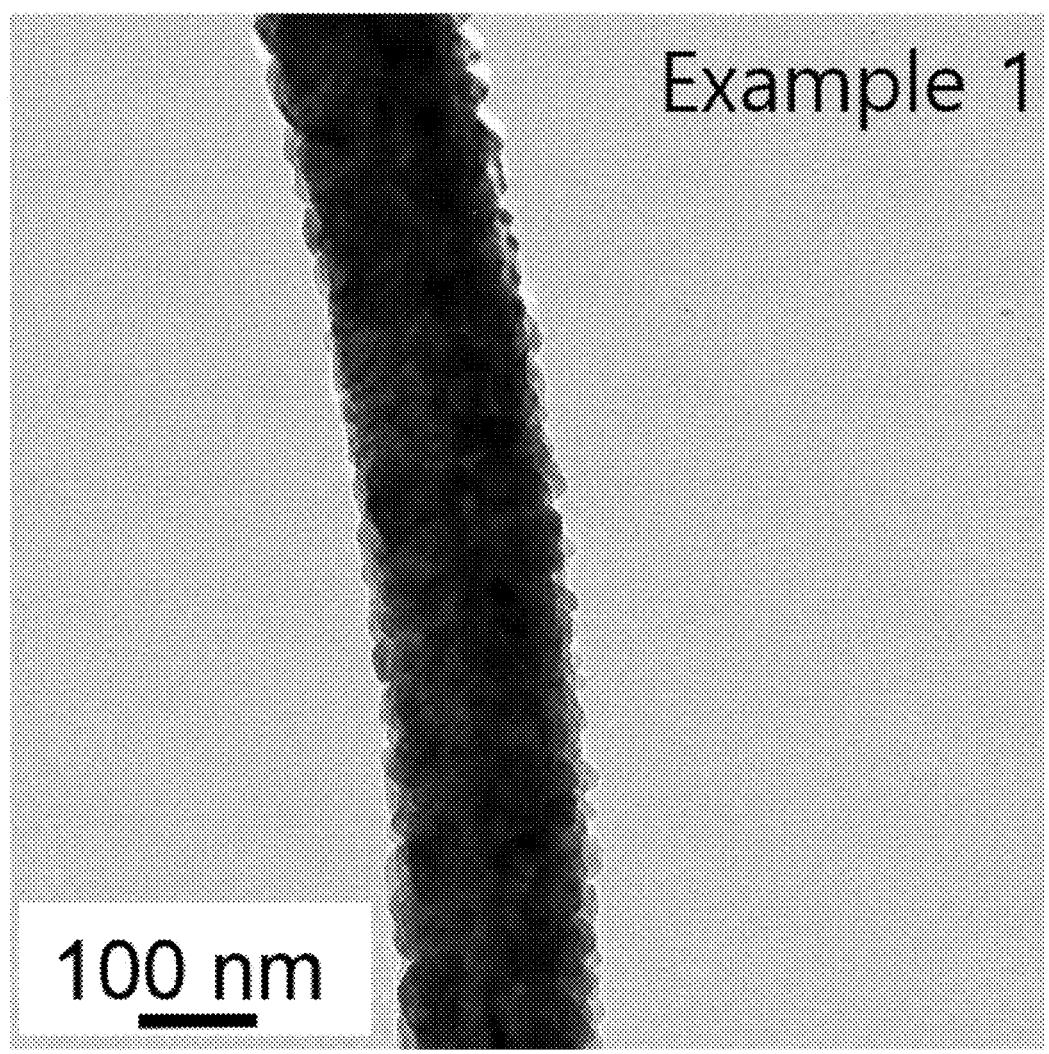
FIG. 7 is a transmission electron microscope/energy dispersive spectroscopy (TEM/EDS) image of a gas sensor prepared in Example 1 according to the present invention.
Figure 8:
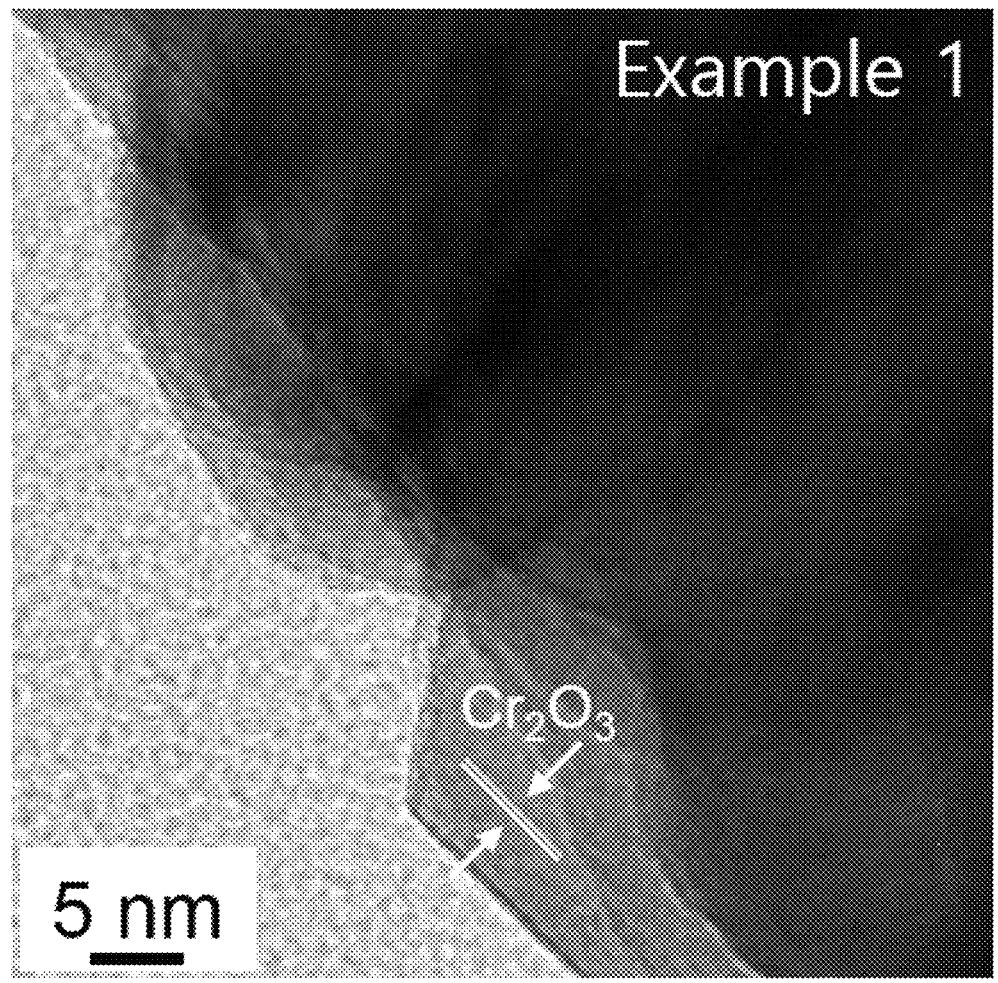
FIG. 8 is a transmission electron microscope/energy dispersive spectroscopy (TEM/EDS) image of a gas sensor prepared in Example 1 according to the present invention.

At this time, the nano islands and the nanowire of case (1) are schematically illustrated through FIGS. 3A and 3B, and the nano islands and the nanowire of case (2) are schematically illustrated through FIGS. 4A and 4B.

Hereinafter, the sensors corresponding to cases (1) and (2) will be described in detail.

(1) Case that a Work Function of the Nano Islands is Greater than that of the Nanowire In a junction between semiconductor materials, an electron transfer takes place from a small work function material to a large work function material. At this time, as illustrated in FIG. 3A, when a work function of the nano islands is greater than that of the nanowire, the electron transfer takes place from the nanowire to the nano islands, and accordingly, a conduction channel of the nanowire is decreased, so that the resistance of the nanowire increases to a very high value.

At this time, as illustrated in FIG. 3B, when an oxidizing gas is injected into a peripheral region of the nanowire in which a conduction channel is formed, a conduction channel variation is limited by a depletion layer caused by the nano islands, and thus, a resistance change is small, but when a reducing gas is injected, the conduction channel variation is significantly increased, so that it may seen that the resistance change will become relatively much larger.

Therefore, as described above, when the nanowire and the nano islands are an n-type oxide semiconductor nanowire and n-type oxide semiconductor nano islands, respectively, and the work function of the nano islands is greater than that of the nanowire, the sensor may more easily sense an infinitesimal amount of a reducing gas.

(2) Case that a Work Function of the Nanowire is Greater than that of the Nano Islands As illustrated in FIG. 4A, when a work function of the nanowire is greater than that of the nano islands, an electron transfer takes place in a direction opposite to that of case (1). That is, as illustrated in FIG. 4A, electrons are transferred from the nano islands to the nanowire, and accordingly, a conduction channel of the nanowire is increased as much as electrons supplied thereto, so that resistance of the nanowire is lowered.

At this time, as illustrated in FIG. 4B, when a reducing gas is injected into a peripheral region of the nanowire, since a depletion layer change due to electrons obtained from oxygen on a surface of the nanowire, is limited due to a restrictive diameter of the nanowire, a resistance change is limited, although a sufficient amount of a reducing gas is injected. On the other hand, when an oxidizing gas is injected, since a depletion layer change, which is caused by an electron release, takes place without limitation, it may be seen that the resistance change will be relatively much larger.

Therefore, as described above, when the nanowire and the nano islands are an n-type oxide semiconductor nanowire and n-type oxide semiconductor nano islands, respectively, and the work function of the nanowire is greater than that of the nano islands, the sensor may more easily sense an infinitesimal amount of an oxidizing gas.

Meanwhile, ZnO, $SnO_2$, $In_2O_3$, $WO_3$, $Fe_2O_3$, $TiO_2$ or the like may be used as the n-type oxide semiconductor. However, the n-type oxide semiconductor is not limited thereto, but an oxide semiconductor, which is usable as a gas sensing material, may be appropriately selected to be used as the n-type oxide semiconductor in consideration of a work function difference.

Meanwhile, it is preferable that the nanowire have a diameter of 20 nm to 100 nm, and the nano islands have a diameter of 10 nm to 30 nm.

When the diameter of the nanowire is less than the lower limit of the range, the maximization of the modulation effect of the nanowire conduction channel may not be expected, and when the diameter of the nano islands exceeds the upper limit of the range, the nano islands contact each other to cause a resistance loss of the sensor element, so that the sensor may be vulnerable to detection of an infinitesimal amount of a gas.

In the sensor according to the present invention, the sum of areas occupied by the nano islands with respect to an entire surface area of the nanowire (the sum of the area occupied by the nano island/the entire surface area of the nanowire) may be preferably in a range of 0.2 to 0.5, more preferably, be in a range of 0.4 to 0.5. When the ratio of the areas does not meet the range, gas sensing performance may be lowered.

As described above, the sensor according to the present invention includes a gas sensing material using a p-n junction and a work function difference, and this is an approach which is fundamentally different from a doping, an alloy addition or the like in a conventional art. That is, since the sensor may include a gas sensing material showing a high sensitivity and a rapid response characteristic by controlling an energy band structure on a surface of the nanowire through introduction of a discrete nano island structure, the sensor may easily sense an infinitesimal amount of a gas.

Also, the present invention provides a method for preparing a sensor, the method including: forming oxide semiconductor particles on a surface of an oxide semiconductor nanowire in a nano island structure, wherein the nanowire and the nano islands are respectively:

1) an n-type oxide semiconductor nanowire and p-type oxide semiconductor nano islands;

2) a p-type oxide semiconductor nanowire and n-type oxide semiconductor nano islands;

3) an n-type oxide semiconductor nanowire and n-type oxide semiconductor nano islands, in which the n-type oxide semiconductor nanowire and the n-type oxide semiconductor nano islands have different work functions from each other (step 1); and providing, as a gas sensing material, the oxide semiconductor nanowire including the oxide semiconductor particles formed on the surface thereof in step 1 on a substrate on which an electrode are formed (step 2).

Hereinafter, a method for preparing a sensor according to the present invention will be described for each step.

In the method for preparing the sensor according to the present invention, step 1 is a step of forming oxide semiconductor particles on a surface of an oxide semiconductor nanowire in a nano island structure.

At this time, in the step 1 as described below, the oxide semiconductor particles are formed on the surface of the oxide semiconductor nanowire in a nano island structure, wherein the nanowire and the nano islands are respectively:

1) an n-type oxide semiconductor nanowire and p-type oxide semiconductor nano islands, respectively;

2) a p-type oxide semiconductor nanowire and n-type oxide semiconductor nano islands;

3) an n-type oxide semiconductor nanowire and n-type oxide semiconductor nano islands, in which the n-type oxide semiconductor nanowire and the n-type oxide semiconductor nano islands have different work functions from each other.

At this time, the respective cases of 1), 2), and 3) are substantially the same as those described above, a description thereof will be omitted.

Meanwhile, the forming of the nano island structure in step 1 may be performed by discretely forming oxide semiconductor particles on the surface of the nanowire through methods such as a thermal deposition method, a sputtering method, a solution method, or a radioysis.

However, the forming of the nano island structure is not limited thereto, but a method for forming nanoparticles on a surface of a nanowire may be appropriately selected to form the nano island structure of step 1.

Meanwhile, in step 1, ZnO, $SnO_2$, $In_2O_3$, $WO_3$, $Fe_2O_3$, $TiO_2$ or the like may be used as the n-type oxide semiconductor. However, the n-type oxide semiconductor is not limited thereto, but an oxide semiconductor, which is usable as a gas sensing material, may be appropriately selected to be used as the n-type oxide semiconductor.

Also, $Co_3O_4$, CoO, NiO, $Ni_2O_3$, $MnO_2$, $Mn_3O_4$, CuO, $Cr_2O_3$, $Bi_2O_3$ or the like may be used as the p-type oxide semiconductor. However, the p-type oxide semiconductor is not limited thereto, but an oxide semiconductor, which is usable as a gas sensor, may be appropriately selected to be used as the p-type oxide semiconductor Meanwhile, in step 1, it is preferable that the nanowire have a diameter of 20 nm to 100 nm, and the nano islands have a diameter of 10 nm to 30 nm.

When the diameter of the nanowire is less than the lower limit of the range, the maximization of the modulation effect of the nanowire conduction channel may not be expected, and when the diameter of the nano island exceeds the upper limit of the range, the nano islands contact each other to cause a resistance loss of the sensor element, so that the sensor may be vulnerable to detection of an infinitesimal amount of a gas.

Also, in step 1, the sum of areas on which the nano islands are formed, with respect to an entire surface area of the nanowire (the sum of the areas on which the nano islands are formed/the entire surface area of the nanowire) may be preferably in a range of 0.2 to 0.5, and more preferably, be in a range of 0.4 to 0.5. When the ratio of the areas does not meet the range, gas sensing performance may be lowered.

In the method for preparing the sensor according to the present invention, step 2 is a step of providing, as a gas sensing material, the oxide semiconductor nanowire having a surface on which the oxide semiconductor particles are formed in step 1 on a substrate on which an electrode are formed.

In the step 2, the oxide semiconductor nanowire having a surface on which the oxide semiconductor particles are formed in step 1, is provided, as the gas sensing material, on a substrate on which an electrode is formed. At this time, the substrate may be a substrate which is formed of an insulation material, such as alumina, glass, or silicon oxide.

Also, the electrode of step 2 may use a metal such as Pt or Ti as an electrode material, but is not limited thereto, and an electrode material, which is typically used in a gas sensor, may be appropriately selected to be used as the electrode.

Meanwhile, the nanowire that is a gas sensing material of step 2, may be dispersed in a liquid, and then, be coated on the substrate on which the electrode is formed That is, since the nanowire that is the gas sensing material, may be easily provided on the substrate through a solution method, a very expensive or complicated equipment is not required in preparing a sensor.

However, the providing of the gas sensing material in step 2 is not limited to the above process, processes for providing a nanowire on a substrate, may be appropriately selected to perform the providing of the gas sensing material.

Meanwhile, the present invention provides a sensor including:

a base material;

a sensing part including a core-shell nanostructure that has a core including a first metal oxide formed on the base material, and a shell including a second metal oxide formed on the core; and two electrode layers spaced apart from each other on the sensing part.

Also, the present invention provides a sensor including:

a base material;

two electrode layers spaced apart from each other on the base material; and a sensing part including a core-shell nanostructure that has a core including a first metal oxide formed on the electrode layer, and a shell including a second metal oxide formed on the core, wherein the shell is coated on an entire surface of the core, and a thickness of the shell has a value equal to or less than a Debye length such that a fully depleted layer is formed throughout the entire shell.

Hereinafter, the sensor in which the shell is formed on the entire surface of the core, and the thickness of the shell has a value equal to or less than a Debye length such that the fully depleted layer is formed throughout the entire shell, will be described in detail below.

As described above, the present invention provides a sensor including: a base material; a sensing part a core-shell structure that has a core including a first metal oxide formed on the base material, and a shell including a second metal oxide formed on the core; and two electrode layers spaced apart from each other on the sensing part, wherein a thickness of the shell has a value equal to or less than a Debye length such that a fully depleted layer is formed throughout the entire shell.

Figure 26:
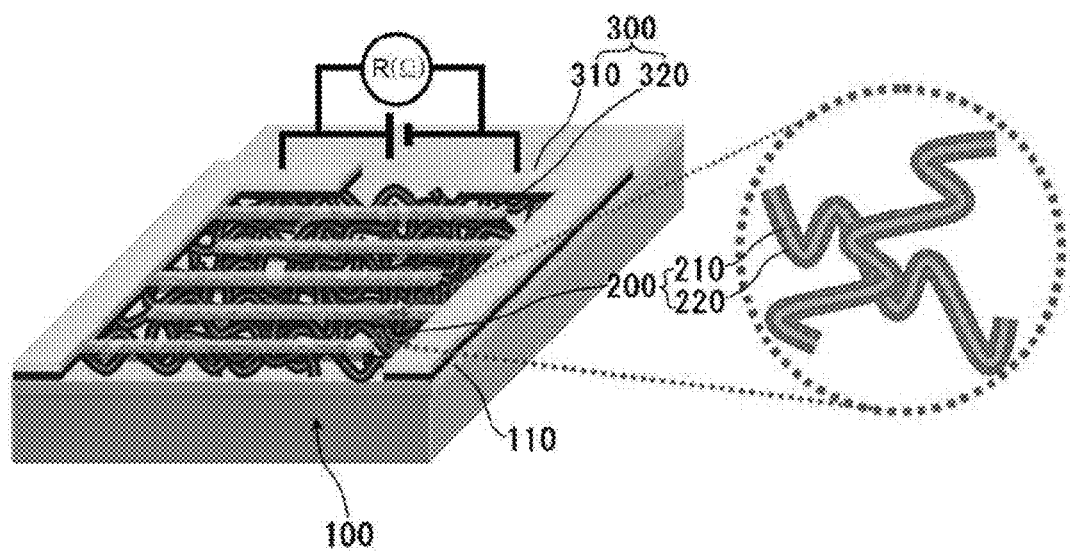
FIG. 26 is a schematic view illustrating a sensor including a core-shell nanostructure prepared according to Specific Example 1 of the present invention.

For example, in the sensor including a base material, a sensing part including a core-shell nanostructure formed on the base material, and two electrodes formed on the sensing part according to the present invention, the core-shell nanostructure may be simply illustrated in a schematic view of FIG. 26, but is not limited thereto.

Also, the present invention provides a sensor including: a base material; two electrode layers spaced apart from each other on the base material; and a sensing part including a core-shell nanostructure that includes a core including a first metal oxide formed on the electrode layer, and a shell including a second metal oxide formed on the core, wherein a thickness of the shell has a value equal to or less than a Debye length such that a fully depleted layer is formed throughout the entire shell.

Figure 27:
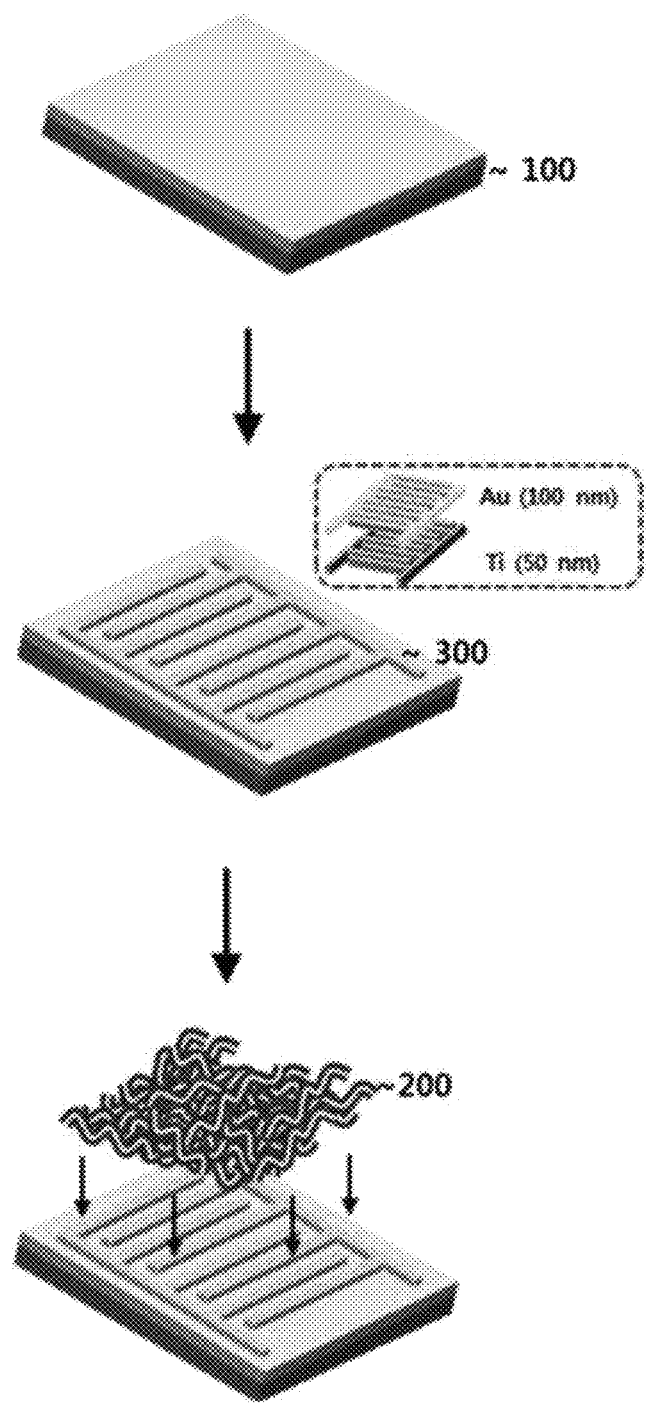
FIG. 27 is a schematic view illustrating a process of preparing a sensor including a core-shell nanostructure according to Specific Example 1 of the present invention.

For example, in the sensor according to the present invention including a base material, two electrodes formed on the base material, and a sensing part including a core-shell nanostructure formed on the electrode on the electrode layer, the core-shell nanostructure is configured such that the positions of the electrode layer and the sensing part are exchanged up and down in comparison with the core-shell nanostructure illustrated in FIG. 26, and a preparing method thereof may be simply illustrated in a schematic view of FIG. 27, but is not limited thereto.

According to Specific Example 1 of the present invention, the sensor may sense about 100 ppm or less of a reducing gas, but is not limited thereto. In the present invention, the sensor is a sensor in which a fully depleted layer is formed on an entire surface of a shell by adjusting the shell such that the shell has a thickness equal to or less than a Debye length, and accordingly, the sensor may be particularly usefully used in sensing an infinitesimal amount of a reducing gas, but is not limited thereto.

For example, the sensor may be usefully used in sensing about 100 ppm or less, for example, an infinitesimal amount, for example, about 0 ppm to about 10 ppm (excluding 0 ppm), about 0 ppm to about 20 ppm (excluding 0 ppm), about 0 ppm to about 40 ppm (excluding 0 ppm), about 0 ppm to about 70 ppm (excluding 0 ppm), about 0 ppm to about 100 ppm (excluding 0 ppm), about 10 ppm to 20 ppm, about 10 ppm to about 40 ppm, about 10 ppm to about 70 ppm, about 10 ppm to about 100 ppm, about 20 ppm to about 40 ppm, about 20 ppm to about 70 ppm, about 20 ppm to about 100 ppm, about 40 ppm to about 70 ppm, about 40 ppm to about 100 ppm, or about 70 ppm to about 100 ppm of a reducing gas, but is not limited thereto. For example, the sensor of the present invention may used in sensing an infinitesimal amount of a reducing gas in a range of from about 0.1 ppm to about 10 ppm, but is not limited thereto.

Figure 28:
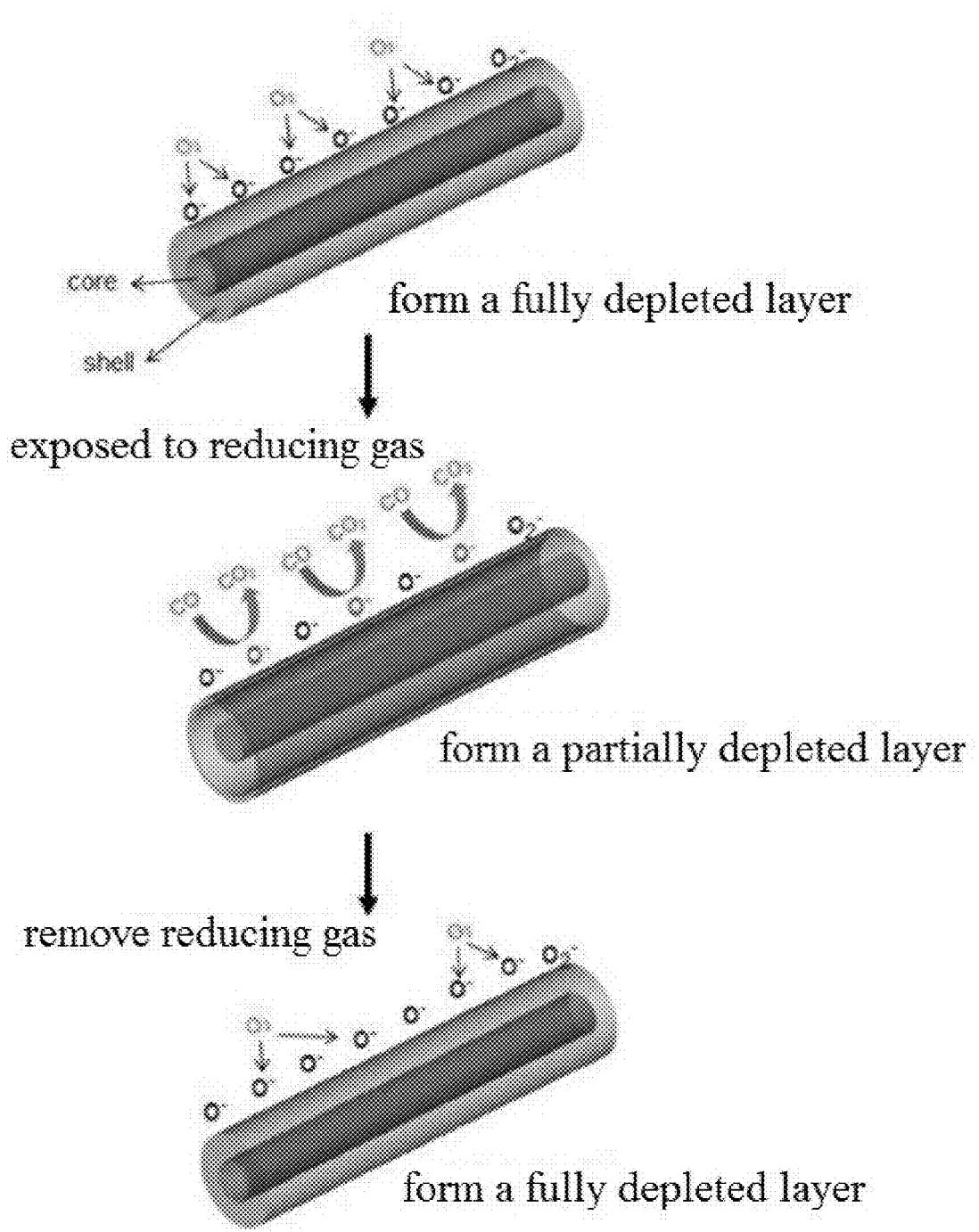
FIG. 28 is a schematic view illustrating a depletion layer changed according to a supply or a removal of a reducing gas to or from a surface of a core-shell nanostructure according to Specific Example 1 of the present invention.
Figure 29:
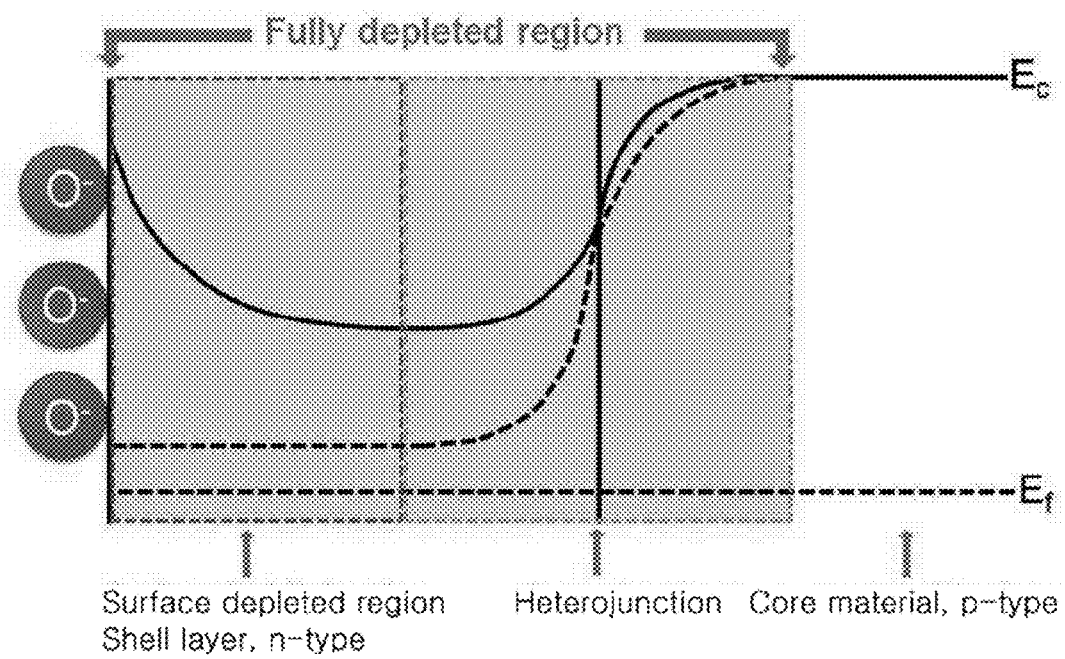
FIG. 29 is a schematic diagram showing a depletion layer model formed on a core-shell nanostructure prepared according to Specific Example 1 of the present invention, where Ec represents a conduction band energy level, and Ef represent a Fermi energy level.

In this regard, FIG. 28 is schematic views illustrating an advantage in sensing a reducing gas such as CO when the shell is adjusted so as to have a thickness equal to or less than a Debye length to form a fully depleted layer, and illustrating that the fully depleted layer of the shell is recovered by an oxygen molecule in air when the reducing gas is removed. A semiconductor gas sensor use a resistance change depending on a thickness change of a depletion layer in order to sense a gas, and a sensing part of the semiconductor gas sensor exists in a state that a depletion layer is formed to some extent by surface adsorption of oxygen always existing in the air. In detail, when oxygen is adsorbed on a surface of the sensing part, oxygen attracts electrons from a surface of the sensing part to be in a negative oxygen ion state, and accordingly, a depletion layer is formed on the surface of the sensing part due to an electron depletion. At this time, when a reducing gas is supplied to the sensor, the negative oxygen ion and the reducing gas react to return some electrons to the sensing part of the sensor, so that the electron depletion extent of the depletion layer is weakened. After that, when the supply of the reducing gas is cut off, adsorption of oxygen in the air takes place again, and thus, the electron depletion extent of the depletion layer is strengthened. Here, when a fully depleted layer is formed on the shell of the core-shell nanostructure included in the sensing part of the sensor, such a phenomenon is maximized, and accordingly, the sensor of the present invention may have a sensitivity even with respect to an infinitesimal amount of a reducing gas, but is not limited thereto. When a reducing gas to be sensed exists in an excessive amount, or an oxidizing gas is applied as a target to be sensed, the sensor according to the present invention may not show a high sensitivity, but the present invention is not limited thereto.

According to Specific Example 1 of the present invention, the sensor may sense a gas selected from the group consisting of $H_2$, CO, $CH_4$, $NH_3$, $CH_3OH$, $C_2H_5OH$, $C_3H_8$, $H_2S$, dimethylamine, triethylamine, benzene, toluene, xylene, and combinations thereof, but is not limited thereto. As described above, the sensor of the present invention is optimized for sensing an infinitesimal amount of a reducing gas, and accordingly, may be expected to show a high sensitivity when a reducing gas, such as $H_2$, CO, $CH_4$, $NH_3$, $CH_3OH$, $C_2H_5OH$, $C_3H_8$, $H_2S$, dimethylamine, triethylamine, benzene, toluene, or xylene is applied as a material to be sensed, but is not limited thereto. For example, the sensor according to the present invention may be a sensor that senses a reducing gas including various volatile organic compounds, but is not limited thereto.

For example, the base material may be a material including a conductive metal base material or an insulation base material, but is not limited thereto. For example, the base material may be a material including a silicon wafer, a conductive metal base material, such as an aluminum base material, or an insulation base material, such as a quartz base material and an oxide base material, but is not limited thereto. For example, the base material may be an insulation base material in itself, or be a material having similar physical characteristics as the insulation base material by further adding an insulation layer to an upper portion thereof, but is not limited thereto. For example, the insulation layer may be a material including a silicon oxide, a silicon dioxide, a silicon nitride, or various polymers, but is not limited thereto.

According to Specific Example 1 of the present invention, the first metal oxide and the second metal oxide may be different metal oxides from each other, but are not limited thereto. For example, different metal oxides are used as the first metal oxide included in the core and the second metal oxide included in the shell, respectively such that a heterojunction may be formed on an interface between the core and shell of the core-shell nanostructure, but the present invention is not limited thereto. The heterojunction may contribute to improvement of a sensitivity of the sensor including the core-shell nanostructure of the present invention, but is not limited thereto. For example, the first metal oxide and the second metal oxide may have different energy band structures from each other, and accordingly, a fully depleted layer may be formed in the core-shell nanostructure of the present invention, but the present invention is not limited thereto.

According to Specific Example of the present invention, each of the first metal oxide and the second metal oxide may independently include an oxide of a metal selected from the group consisting of Ti, Sn, Zn, Mn, Mg, Ni, W, Co, Fe, Ba, In, Zr, Cu, Al, Bi, Pb, Ag, Cd, Y, Mo, Rh, Pd, Sb, Cs, La, and combinations thereof, but the present invention is not limited thereto. For example, a metal oxide semiconductor, which is usable as each of the first metal oxide and the second metal oxide, may include a material selected from the group consisting of $TiO_2$, $SnO_2$, ZnO, $MnO_2$, MgO, NiO, $WO_3$, $Co_3O_4$, $Fe_2O_3$, $BaTiO_3$, $In_2O_3$, $ZrO_2$, $CuAlO_2$, $Bi_2O_3$, metal oxide composites (for example, Ti-doped $SnO_2$, Sn-doped ZnO, Mg-doped ZnO, Mn-doped ZnO, Ni-doped ZnO, Co-doped ZnO, Fe-doped ZnO, Mn-doped MgO, Ni-doped MgO, Co-doped MgO, Fe-doped MgO, Mg-doped $MnO_2$, Ni-doped $MnO_2$, Co-doped $MnO_2$, Fe-doped $MnO_2$, Mg-doped NiO, Mn-doped NiO, Co-doped NiO, Fe-doped NiO, Mg-doped $Co_3O_4$, Mn-doped $Co_3O_4$, Ni-doped $Co_3O_4$, Fe-doped $Co_3O_4$, Mg-doped $Fe_2O_3$, Mn-doped $Fe_2O_3$, Ni-doped $Fe_2O_3$, Co-doped $Fe_2O_3$, or Ag-doped ZnO), PZT (referred to as a generic term of solid solutions of $PbZrO_3$ and $PbTiO_3$), an Ag oxide, a Cd oxide, an Y oxide, Mo oxide, an Rh oxide, a Pd oxide, a Sb oxide, a Cs oxide, an La oxide, and combinations thereof, but is not limited thereto.

According to Specific Example 1 of the present invention, the shell may include nanoparticles of the second metal oxide, but is not limited thereto. In case that the shell corresponding to a surface portion of the sensing part includes a plurality of nanosized particles to have a rough surface, the case may increase a surface area of the shell compared to a case that the shell has a smoothing surface, and accordingly, a sensitivity of a sensor may be improved while a region adsorbing gas molecules is expanded, but the present invention is not limited thereto.

For example, a particle size of the first metal oxide included in the core may be larger than that of the second metal oxide included in the shell, but the present invention is not limited thereto. For example, it may be confirmed that the core and the shell are apparently formed of different materials from each other by using a difference between the particle size included in the core and the particle size included in the shell, and accordingly, it may be confirmed that a heterojunction that is formed between the core and the shell exists, but the present invention is not limited thereto. For example, the particle size of the second metal oxide is smaller than that of the first metal oxide included in the core, and accordingly, a channel, which is formed between small particles forming the shell, may function as a path for an electron transfer, and contribute to improvement of sensitivity of the sensor, but the present invention is not limited thereto.

According to Specific Example 1 of the present invention, the core may include a nanowire shape having a diameter of about 20 nm to about 200 nm, but is not limited thereto. For example, the core may include a nanowire shape having a diameter of about 20 nm to about 50 nm, about 20 nm to about 80 nm, about 20 nm to about 100 nm, about 20 nm to about 130 nm, about 20 nm to about 150 nm, about 20 nm to about 200 nm, about 50 nm to about 80 nm, about 50 nm to about 100 nm, about 50 nm to about 130 nm, about 50 nm to about 150 nm, about 50 nm to about 200 nm, about 80 nm to about 100 nm, about 80 nm to about 130 nm, about 80 nm to about 150 nm, about 80 nm to about 200 nm, about 100 nm to about 130 nm, about 100 nm to about 150 nm, about 100 nm to about 200 nm, about 130 nm to about 150 nm, about 130 nm to about 200 nm, or about 150 nm to about 200 nm, but is not limited thereto.

For example, the core may have a networked shape of nanowires, and an electrospinning method of electrospinning a solution including a precursor of the first metal oxide and a polymer, may be used in order to form the core having the networked shape of nanowires, but the present invention is not limited thereto. For example, the electrospinning method may include a method of electrospinning, in an organic solvent, the solution including the precursor of the first metal oxide and the polymer, but is not limited thereto. Here, a precursor compound of a metal oxide, which is generally used in the art, may be used as the precursor of the first metal oxide, and a polymer, which is generally used in the art in performing the electrospinning method, may be used as the polymer, but the present invention is not limited thereto.

For example, a thickness of the shell may be adjusted to a value equal to or less than a Debye length in order to form a fully depleted layer throughout the entire shell, and the Debye length may be a value determined according to a species of a compound forming the shell, but is not limited thereto. In detail, the Debye length may be a value determined under the influence of a change in intrinsic characteristics such as a dielectric constant according to a species of the compound forming the shell, and also, be a value determined under the influence of a height of a potential barrier according to a band bending phenomenon resulting from a heterojunction between the shell and the core, but is not limited thereto. For example, when the material forming the core is n-type $SnO_2$, and the material forming the shell is n-type ZnO, a Debye length, which is formed on the surface of the shell, may be about 69 nm, and a Debye length, which is formed on the heterojunction between the shell and the core, may be 53 nm, but the present invention is not limited thereto.

For example, the shell may be formed by using an atomic layer deposition (ALD), but is not limited thereto. For example, the atomic layer deposition may be performed several times, and the thickness of the shell may be adjusted to the Debye length or less by adjusting the performed number of the atomic layer deposition, but the present invention is not limited thereto. For example, the shell may be formed outside the core by using a chemical vapor deposition (CVD), a laser ablation, or a template, but the present invention is not limited thereto.

According to Specific Example 1 of the present invention, the core-shell nanostructure may include a p-n type core-shell nanostructure or an n-n type core-shell nanostructure, but is not limited thereto. For example, the p-n type core-shell nanostructure may include a core that includes a p-type metal oxide semiconductor and a shell that includes an n-type metal oxide semiconductor, for example, a CuO—ZnO, CuO—$SnO_2$, CuO—$TiO_2$, NiO—ZnO, NiO—$SnO_2$, NiO—$TiO_2$, $Co_3O_4$—ZnO, $CO_3O_4$—$SnO_2$, or $Co_3O_4$—$TiO_2$ core-shell nanostructure, but the present invention is not limited thereto. For example, the n-n type core-shell nanostructure may include a core that includes an n-type metal oxide semiconductor and a shell that includes an n-type metal oxide semiconductor. Here, the n-type metal oxide semiconductor included in the core and the n-type metal oxide semiconductor included in the shell may be different species, and, for example, a $Fe_2O_3$—ZnO, $In_2O_3$—ZnO, $SnO_2$—ZnO, $TiO_2$—ZnO, ZnO—$TiO_2$, or $TiO_2$—$SnO_2$ core-shell nanostructure may be included in the n-n type core-shell nanostructure, but the present invention is not limited thereto. In case that each of the p-n type or n-n type core-shell nanostructure is included in the sensing part of the sensor, the case may allow the sensor to show a high sensitivity with respect to a reducing gas compared to a case that a nanostructure formed of a single material is included in the sensing part of the sensor, but the present invention is not limited thereto. Also, the core-shell nanostructure of the present invention may be suitable to prepare the sensing part of the sensor having a high sensitivity compared to an alloy hetero nanostructure prepared by alloying different materials, but the present invention is not limited thereto.

In relation to this, in the core-shell hetero nanostructure of the present invention, a depletion layer, which is formed in the shell layer and a heterojunction of an interface between different materials, contributes to improvement of the sensitivity of the sensor. As described above, a sensing mechanism of the semiconductor gas sensor is related to a resistance change occurring in an interaction between a gas molecule and a semiconductor material. When the sensor is exposed to the air, oxygen molecules are rapidly adsorbed on a surface of the sensor to form negative ions, and, at this time, since electrons are attracted from a vicinity of the surface, a formation of a depletion layer in the surface is induced. In the core-shell nanostructure, an insulation surface layer is supported by a heterojunction formed on an interface between the shell material and the core material to form a wide insulation layer. When the sensor is exposed to a reducing gas, such as Co, negative ions are again released during a reaction with CO gas molecules. In the core-shell nanostructure, the depletion layer, which is formed in the shell layer and the heterojunction, causes a resistance change. A gas sensitivity of the core-shell structure is greatly affected by a thickness of the shell, and in detail, when a width of the shell layer is adjusted to a width or less of the depletion layer according to the present invention, the gas sensitivity may be greatly improved, but the present invention is lot limited thereto.

For example, when the metal oxide semiconductor is an n-type oxide semiconductor and is exposed to oxidizing chemical species molecules, such as oxygen molecules, and thus oxidizing chemical species molecules are adsorbed on a surface of the metal oxide semiconductor, the metal oxide semiconductor donates electrons to the oxidizing species to form a depletion layer on the surface of the metal oxide semiconductor, so that electric resistance is increased. Meanwhile, when the metal oxide semiconductor is an n-type oxide semiconductor, and is exposed to reducing chemical species molecules, such as $H_2$ or $CO_2$ molecules, and thus reducing chemical molecules are adsorbed on a surface of the metal oxide semiconductor, $H_2$ or CO molecules combine with oxygen molecules adsorbed on the surface of the metal oxide semiconductor to be converted into $H_2O$ or $CO_2$, and $H_2O$ or $CO_2$ are separated from the metal oxide semiconductor, electrons captured by separated oxygen are excited to be transferred to a conduction band of the metal oxide semiconductor, so that resistance of the metal oxide semiconductor is decreased. The sensor of the present invention may sense an infinitesimal amount of a reducing gas with a high sensitivity by using the aforementioned resistance change, but is not limited thereto.

According to Specific Example 1 of the present invention, the electrode layer may include a single-layered electrode layer containing a metal selected from the group consisting of Au, Pt, Cu, and combinations thereof, or include a multi-layered electrode layer including a layer of a metal selected from the group consisting of Ti, Ni, Cr, and combinations thereof in addition to the single-layered electrode layer, but is not limited thereto. For example, Au, Pt, or Cu of metals included in the electrode layer, may substantially function as an electrode, and Ti, Ni, or Cr of metals included in the electrode layer, may be further included in order to improve bondability between the electrode layer and other parts of the sensor, but the present invention is not limited thereto. For example, as illustrated in the schematic view of FIG. 47, while the sensor may include a multi-layered electrode layer including all of an Au metal layer and a Ti metal layer, the present invention is not limited thereto. For example, the multi-layered electrode layer may include the Au metal layer functioning as an electrode and a Ni metal layer improving bondability at the same time, but is not limited thereto. For example, a method, such as a sputtering method or an evaporation method, which is generally used in fabricating an electrode in the art, may be used in order to form the electrode, but the present invention is not limited thereto.

Further, the present invention provides a method for preparing a sensor, the method including:

forming a core including a first metal oxide on a base material;

forming a shell including a second metal oxide on the core to form a sensing part including a core-shell nanostructure; and forming two electrode layers spaced apart from each other on the sensing part, wherein a thickness of the shell has a value equal to or less than a Debye length to form a fully depleted layer throughout the entire shell.

Also, the present invention provides a method for preparing a sensor, the method including:

forming two electrode layers spaced apart from each other on the base material; and forming a core including a first metal oxide, forming a shell including a second metal oxide on the core to form a sensing part including a core-shell nanostructure, and depositing the core-shell nanostructure on the electrode layer as a sensing part, wherein a thickness of the shell has a value equal to or less than a Debye length to form a fully depleted layer throughout the entire shell.

The preparing method of the present invention is a method for preparing a sensor including the core-shell nanostructure, in which the thickness of the shell has the value of the Debye length or less to form the fully depleted layer throughout the entire shell, and in the description thereof, details with respect to some repeated elements will be omitted. Also, although a description with respect to repeated elements is omitted, this will be equally to the preparing method.

For example, in the preparing method of the present invention, when the core-shell nanostructure is formed, a firing process may be included after forming the core, and the firing process may be added after forming the shell, but the present invention is not limited thereto.

According to Specific Example 1 of the present invention, the forming of the core may include electrospinning a solution including a precursor of the first metal oxide and a polymer to form the core in a nanowire shape, that is, may include using an electrospinning method, but is not limited thereto. For example, the electrospinning method may include a method performed through a method of electrospinning, in an organic solvent, the solution including the precursor of the first metal oxide and the polymer, but is not limited thereto. Herein, a precursor compound of a metal oxide, which is generally used in the art, may be used as the precursor of the first metal oxide, and a polymer, which is generally used in the art in performing the electrospinning method, may be used as the polymer, but the present invention is not limited thereto.

According to Specific Example 1 of the present invention, the shell may be formed by using an atomic layer deposition, but is not limited thereto. Also, the shell may be formed on an outer surface of the core by using a chemical vapor deposition (CVD), a laser ablation, or a template in addition to the atomic layer deposition, but is not limited thereto.

When the shell is formed by using the atomic layer deposition, a temperature and a pressure inside a reactor function as two important variables, and may be values varied according to a vapor pressure of a material to which the atomic layer deposition is applied. For example, when $Zn(C_2H_5)_2$ (DEZn) and $H_2O$ are used as starting materials in order to form a ZnO shell layer, the temperature and the pressure inside the reactor are set to about 150° C. and about 0.3 Torr, respectively to perform the atomic layer deposition, but are not limited thereto.

For example, the atomic layer deposition may be performed several times in order to form the shell, but is not limited thereto. For example, when DEZn and $H_2O$ are used as starting materials in order to perform the ZnO shell layer, the supply of DEZn, the ventilation using an inert gas, such as nitrogen, and the supply of $H_2O$ may correspond to the atomic layer deposition performed one time, and the processes may be performed several times to form a shell having a thickness that is increased in linear proportion to the performed number, but the present invention is not limited thereto.

According to Specific Example 1 of the present invention, the performed number of the atomic layer deposition is adjusted such that the thickness of the shell has a value equal to or less than a Debye length, but the present invention is not limited thereto. For example, a thickness of the shell may be adjusted to a value equal to or less than a Debye length in order to form a fully depleted layer throughout the entire shell, and the Debye length may be a value determined according to a species of a compound forming the shell, but is not limited thereto.

According to Specific Example 1 of the present invention, a shell, which includes the second metal oxide different from the first metal oxide, may be formed on the core to form a heterojunction on an interface between the core and the shell which are included in the core-shell nanostructure, but the present invention is not limited thereto. The heterojunction may contribute to improvement of a sensitivity of the sensor including the core-shell nanostructure of the present invention, but is not limited thereto. For example, the first metal oxide and the second metal oxide may have different energy band structures from each other, and accordingly, a fully depleted layer may be formed in the core-shell nanostructure of the present invention, but the present invention is not limited thereto.

According to Specific Example 1 of the present invention, the core may be formed by using a p-type metal oxide, and the shell may be formed on the core by using an n-type metal oxide to prepare a p-n type core-shell nanostructure, but the present invention is not limited thereto. For example, the p-n type core-shell nanostructure may include a $CuO$—$ZnO$, $CuO$—$SnO_2$, $CuO$—$TiO_2$, $NiO$—$ZnO$, $NiO$—$SnO_2$, $NiO$—$TiO_2$, $Co_3O_4$—$ZnO$, $Co_3O_4$—$SnO_2$, or $Co_3O_4$—$TiO_2$ core-shell nanostructure, but is not limited thereto. In case that the p-n type core-shell nanostructure is included in the sensing part of the sensor, the case may allow the sensor to show a high sensitivity with respect to a reducing gas compared to a case that a nanostructure formed of a single material is included in the sensing part of the sensor, but the present invention is not limited thereto. Also, the core-shell nanostructure of the present invention may be suitable to prepare the sensing part of the sensor having a high sensitivity compared to an alloy hetero nanostructure prepared by alloying different materials, but the present invention is not limited thereto.

According to Specific Example 1 of the present invention, the core may be formed by using an n-type metal oxide, and the shell may be formed on the core by using an n-type metal oxide different from the n-type metal oxide included in the core to prepare an n-n type core-shell nanostructure, but the present invention is not limited thereto. For example, the n-n type core-shell nanostructure may include an $Fe_2O_3$—$ZnO$, $In_2O_3$—$ZnO$, $SnO_2$—$ZnO$, $TiO_2$—$ZnO$, $ZnO$—$TiO_2$, or $TiO_2$—$SnO_2$ core-shell nanostructure, but is not limited thereto. In case that the n-n type core-shell nanostructure is included in the sensing part of the sensor, the case may allow the sensor to show a high sensitivity with respect to a reducing gas compared to a case that a nanostructure formed of a single material is included in the sensing part of the sensor, but the present invention is not limited thereto. Also, the core-shell nanostructure of the present invention may be suitable to prepare the sensing part of the sensor having a high sensitivity compared to an alloy hetero nanostructure prepared by alloying different materials, but the present invention is not limited thereto.

According to Specific Example 1 of the present invention, the preparing method of the present invention may include performing the depositing of the core-shell nanostructure on the electrode as the sensing part through a printing, but is not limited thereto. For example, the core-shell nanostructure may be deposited on the electrode layer as a sensing part by printing the core-shell structure mixed with a binder on the electrode layer, and then heat-treating the resultant mixture to remove the binder, but the present invention is not limited thereto.

Hereinafter, Specific Example 1 of the present invention will be descried in more detail with reference to the schematic view of FIG. 26.

FIG. 26 is a schematic view illustrating a sensor including a core-shell nanostructure prepared according to Specific Example 1 of the present invention. As illustrated in FIG. 26, the sensor may include a base material 100, an insulation layer 110 formed on the base material 100, a sensing part 200 formed on the insulation layer 110, and two electrode layer 300 spaced apart from each other on the sensing part 200, in which the sensing part 200 includes a core 210, which includes a first metal oxide and has a networked shape of nanowires, and a shell 220, which includes a second metal oxide and is formed on the core 210, but is not limited thereto.

In the core-shell nanostructure provided in the sensing part 200 of FIG. 26, the core 210 may be formed in a networked shape of nanowires by using an electrospinning, and the shell 220, which is formed on the core 210, may be formed by using an atomic layer deposition, but are limited thereto.

For example, the electrospinning 210 for forming the core 210 may be sequentially performed according to processes to be described below, but the present invention is not limited thereto.

First, a spinning solution for performing the electrospinning is prepared. The spinning solution may be prepared by mixing a first metal oxide for forming a core and a polymer solution, and then converted to a viscous solution by stirring the resultant mixture for a predetermined time period after mixing. For example, the stirring may be performed at a temperature of about 40° C. to about 80° C. for about 3 hours to about 10 hours, but is not limited thereto.

Next, the spinning solution may be loaded in a syringe. For example, the viscous solution is filled into the syringe, and the syringe may be disposed at a predetermined height from the base material 100 disposed on a conduction material such as aluminum. At this time, a needle of the syringe and the base material 100 may form a predetermined angle. For example, the syringe may be disposed at a height of about 10 cm to about 50 cm from the base material 100, and the needle of the syringe and the base material 100 may form an angle of about 10° to about 90°, but the present invention is not limited thereto.

Next, the spinning solution may be spun on the base material 100. For example, a predetermined positive voltage is applied to the needle of the syringe, and a predetermined negative voltage is applied to the conductive material disposed on a lower portion of the base material 100, and accordingly, the spinning solution may be electrospun on the base material 100 to form the core 210 having the networked shape of nanowires, but the present invention is not limited thereto. For example, each of the positive voltage and the negative voltage may have a magnitude of 5 kV to 50 kV, but is not limited thereto. Also, a feeding rate of the spinning solution with respect to the base material 100 may range, for example, from 0.01 mL/h to 2 mL/h, but is not limited thereto.

Next, the core 210 may be calcinated. The calcination may be performed in order to remove unnecessary impurities from the core 210, which has the networked shape of nanowires, and on which impurities may be included immediately after electrospinning, and for example, may be performed at a temperature of about 100° C. to 1,000° C. for 3 hours to 15 hours under various ambients, such as air, Ar, $N_2$, or $O_2$, but is not limited thereto.

Meanwhile, after the core 210 is formed according to the electrospinning exemplarily described, for example, the shell 220 may be formed on the core 210 through an atomic layer deposition, but the present invention is not limited thereto. The shell 220 may be formed by performing the atomic layer deposition several times, and the performed number of the atomic layer deposition may be adjusted to form the shell 220 at a desired thickness, but the present invention is not limited thereto. For example, a temperature and a pressure inside the reactor in which the atomic layer deposition is performed, may be in a range of about 100° C. to about 300° C. and in a range of about 0.1 Torr to 0.6 Torr, respectively, but are not limited thereto. Also, for example, while the atomic layer deposition is performed, a pulse length with respect to each of elements may range from about 0.1 seconds to 5 seconds, and the performed number of the atomic layer deposition may be about 1 time or more times, for example, about 1 time to about 10 times, about 1 time to about 100 times, about 1 time to about 1,000 times, and about 1 time to about 10,000 times, but the present invention is not limited thereto.

Meanwhile, in the sensor of FIG. 26, the electrode layer 300 may be disposed on the sensing part 200 including the core-shell nanostructure, and a first electrode layer 310 and a second electrode layer 320 may be spaced apart from each other, but the present invention is not limited thereto. Also, each of the first electrode layer 310 and the second electrode 320 may be connected to the core-shell nanostructure, but are not limited thereto. The electrode layer 300 may be formed by stacking at least one metal layer, and be formed according to a method, such as a sputtering method or an evaporation method, which is generally used in the art, but is not limited thereto.

The sensor, which includes, as the sensing part 200, the core-shell nanostructure of the present invention formed according to the foregoing exemplary processes, is a sensor that has an excellent sensitivity with respect to an infinitesimal amount of a reducing gas, and may be applied in various fields, but is not limited thereto.

MODE FOR CARRYING OUT THE PRESENT INVENTION

Hereinafter, the present invention will be described in more detail through Examples below. However, the following Examples are provided only for illustration of the present invention and should not be construed as limiting the scope of the present invention.

<Example 1> Preparing 1 of a Gas Sensor $Cr_2O_3$ nano islands were discretely formed on a surface of a $SnO_2$ nanowire.

At this time, the forming of the nano islands was performed through processes described below.

A $SnO_2$ nanowire was selectively grown on a PIEs substrate for 5 minutes by applying a vapor-liquid-solid method (VLS) on a $SiO_2$ (300 nm)/Si substrate on which PIEs (Au 3 nm/Pt 200 nm/Ti 50 nm) were formed. At this time, the Au layer, which is disposed on a top of the PIEs substrate, was used as a catalyst for growing the nanowire, and the Pt layer was used as an electrode. Also, the Ti layer was used for improving a bonding between the substrate and the electrode layer.

Further, chromium was deposited on the substrate on which the $SnO_2$ nanowire was grown, for 30 seconds by using a DC sputter equipped with a chromium (Cr) target, and the chromium-deposited substrate was heat-treated for 2 hours under an oxygen atmosphere having a temperature of 700° C., and finally, the $SnO_2$ nanowire on which the $Cr_2O_3$ nano islands were formed, was disposed on the substrate to prepare a gas sensor.

<Example 2> Preparing 2 of a Gas Sensor

Except that the sputtering was performed by equipping a titanium (Ti) target instead of the chromium (Cr) target of Example 1, Example 2 was performed in the same manner as Example 1, to prepare a gas sensor in which a $SnO_2$ nanowire was provided on a substrate and $TiO_2$ nano islands were discretely formed on a surface of the $SnO_2$ nanowire.

<Example 3> Preparing 3 of a Gas Sensor

Except that the sputtering was performed by equipping a tungsten (Ti) target instead of the chromium (Cr) target of Example 1, Example 2 was performed in the same manner as Example 1 to prepare a gas sensor in which a $SnO_2$ nanowire was provided on a substrate and $WiO_3$ nano islands were discretely formed on a surface of the $SnO_2$ nanowire.

<Example 4> Preparing 4 of a Gas Sensor $TiO_2$ nano islands were discretely formed on a surface of a NiO nanowire.

At this time, the forming of the nano islands was performed through processes described below.

In order to prepare an electrospinning solution, 1 g of copper acetate as a precursor was dissolved in 22 g of distilled water that is a solvent, and 2 g of polyvinyl alcohol was added to the nickel acetate-dissolved solvent in order to maintain appropriate viscosity for electrospinning, and the resultant mixture was stirred at a temperature of about 60° C. to 70° C. for 4 hours or more.

The prepared electrospinning solution was electrospun at a flow rate of 0.05 ml/h and at an applied voltage of (+)15 kV/(−)5 kV for about 10 minutes to prepare a p-type NiO nanowire.

Titanium was deposited on the prepared p-type NiO nanowire for 30 seconds by using a DC sputter equipped with a Ti target, and the Ti-deposited nanowire was heat-treated in an oxygen atmosphere at a temperature of 700° C. for 2 hours to prepare a NiO nanowire on which $TiO_2$ nano islands were formed.

Interdigital electrodes (IDEs) were formed by using a sputtering on the prepared NiO nanowire on which the $TiO_2$ islands were formed, and the IDEs were formed in a Pt (200 nm)/Ti (50 nm) structure.

A gas sensor was finally prepared through this.

Comparative Example 1

Except that nano islands were not formed on a $SnO_2$ nanowire, Comparative Example 1 was performed in the same manner as Example 1 to prepare a gas sensor.

<Experimental Example 1> Analysis 1 of a Gas Sensor Having a p-n Junction Structure The following analyses were performed in order to analyze characteristics of the gas sensor prepared in Example 1.

(1) Scanning Electron Microscope and Transmission Electron Microscope Observations In the gas sensor prepared in Example 1, a microstructure of the $SnO_2$ nanowire that is a gas sensing material, was observed by using a scanning electron microscope and a transmission electron microscope (TEM/EDS), and the observed results are shown in FIGS. 5 to 8.

As shown in FIGS. 5 to 8, in the gas sensor prepared in Example 1, it may be seen that $Cr_2O_3$ nano islands are discretely attached to a surface of the $SnO_2$ nanowire that is a gas sensing material.

Through this, it may be confirmed that the gas sensor according to the present invention includes, as gas sensing materials, a nanowire and nano islands that are discretely formed on a surface of the nanowire.

(2) X-Ray Diffraction Analysis

Figure 9:
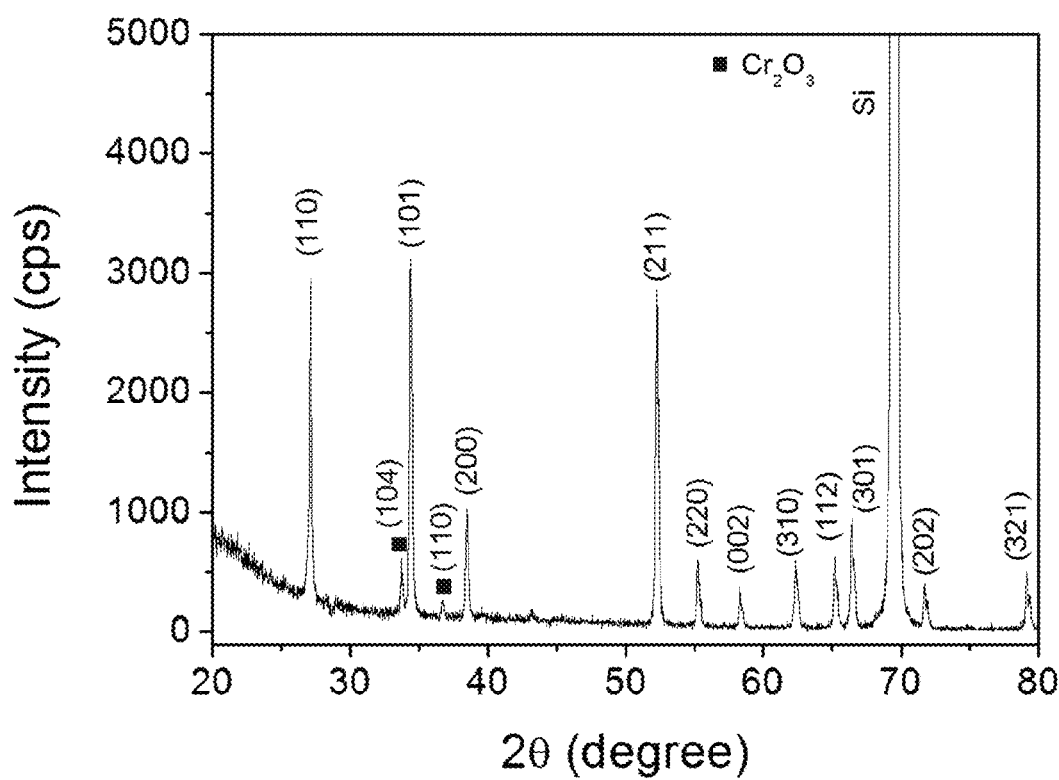
FIG. 9 is a graph showing an X-ray diffraction analysis of a gas sensor prepared in Example 1 according to the present invention.

In the gas sensor prepared in Example 1, a phase analysis was performed by an X-ray diffractometer to analyze a phase of the $SnO_2$ nanowire that is a gas sensing material, and the analyzed results are shown in FIG. 9.

As shown in FIG. 9, it may be seen that a peak corresponding to $Cr_2O_3$ attached on a surface of the $SnO_2$ nanowire that is a gas sensing material, is detected.

(3) Response Analysis According to a Gas Concentration

Figure 10:
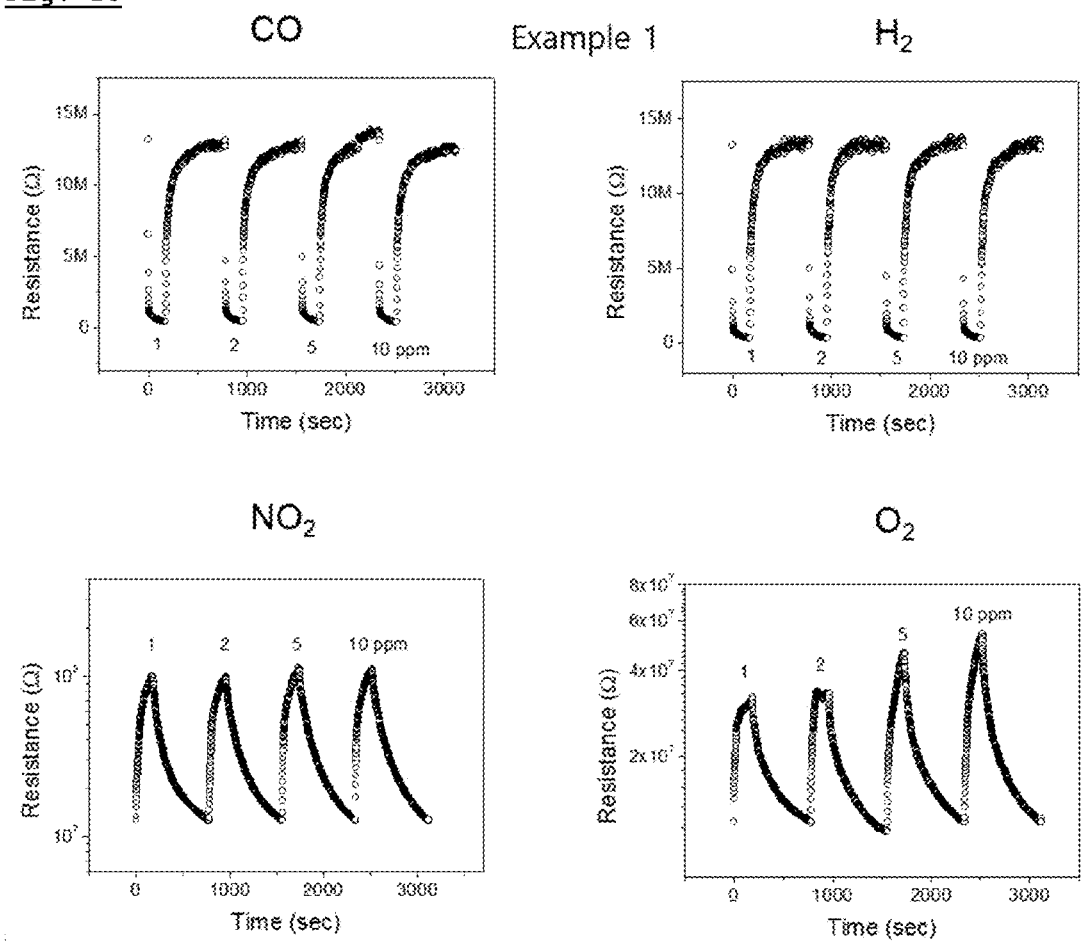
FIG. 10 is a response curve graph showing a sensitivity depending on a concentration of a reaction gas in a gas sensor prepared in Example 1 according to the present invention.
Figure 11:
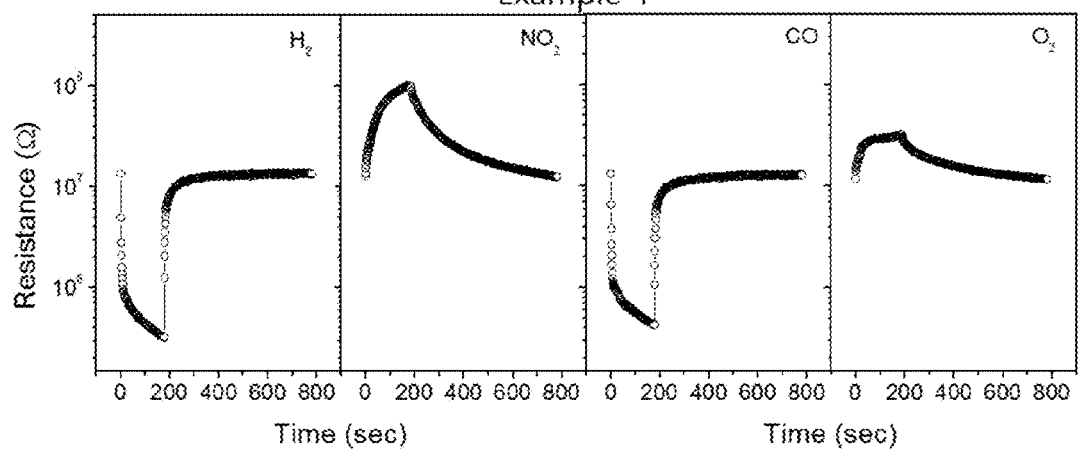
FIG. 11 is a response curve graph showing a sensitivity depending on a concentration of a reaction gas in a gas sensor prepared in Example 1 according to the present invention.

In the gas sensor prepared in Example 1, a resistance change of the sensor was measured by changing a gas concentration of CO, $H_2$, $NO_2$, and $O_2$ in order to analyze a sensitivity according to a gas concentration, and the measured results are shown in FIGS. 10 and 11.

As shown in FIG. 10, it may be seen that the gas sensor prepared in Example 1 shows that a resistance change with respect to a reducing gas is greater than a resistance change with respect to an oxidizing gas.

Also, as shown in FIG. 11, it may be seen that the gas sensor prepared in Example 1 shows that an improvement in sensitivity with respect to reducing gases (CO and $H_2$) is considerably greater than an improvement in sensitivity with respect to oxidizing gases ($NO_2$ and $O_2$) due to a formation of the $Cr_2O_3$ nano islands.

(4) Response Analysis According to Existence or Non-Existence of Nano Islands

In order to analyze a response rate of gas sensors prepared in Example 1 and Comparative Example 1 for each response gas, a resistance change of the sensor according to a concentration of $H_2$, CO, $NO_2$, and $O_2$ gases was measured to measure response R.

At this time, a resistance change was measured at a gas concentration of 1 ppm to 50 ppm at a temperature of 300° C. to measure the response R. Also, the response R is defined as R=Rg/Ra or R=Ra/Rg, where Rg represents a resistance value when a reactive gas exists, and Ra represents an initial resistance value when a reactive gas does not exist. The response analysis results are shown in FIG. 12.

Figure 12:
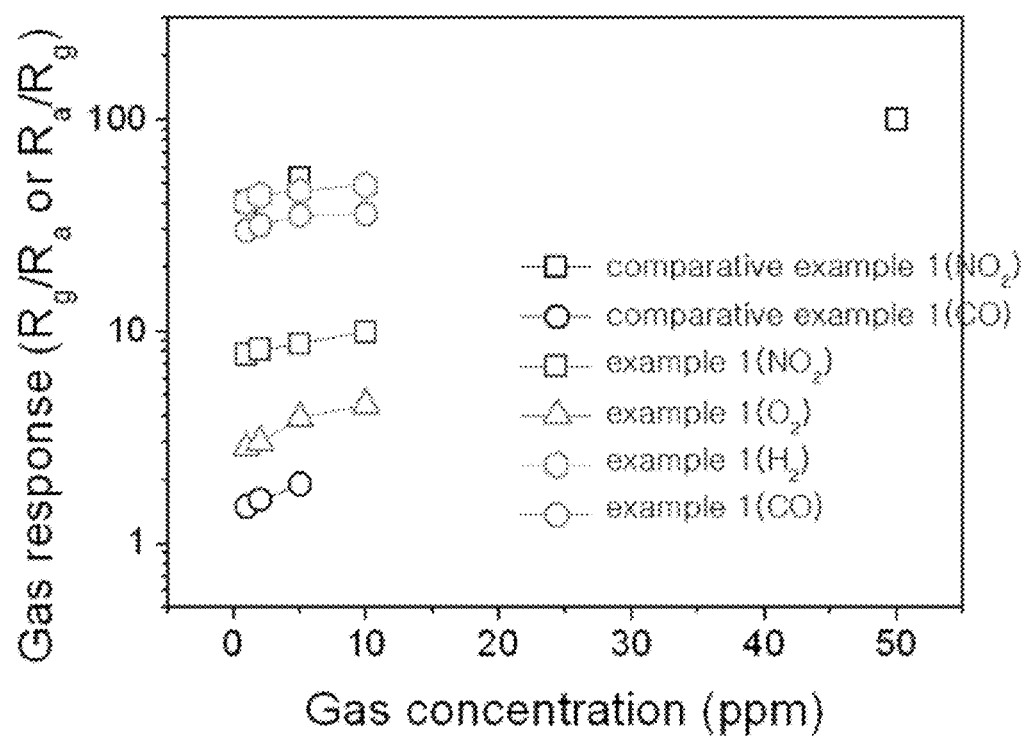
FIG. 12 shows graphs comparing a sensitivity of a gas sensor prepared in Example 1 according to the present invention and a sensitivity of a sensor prepared in Comparative Example 1.
Figure 13:
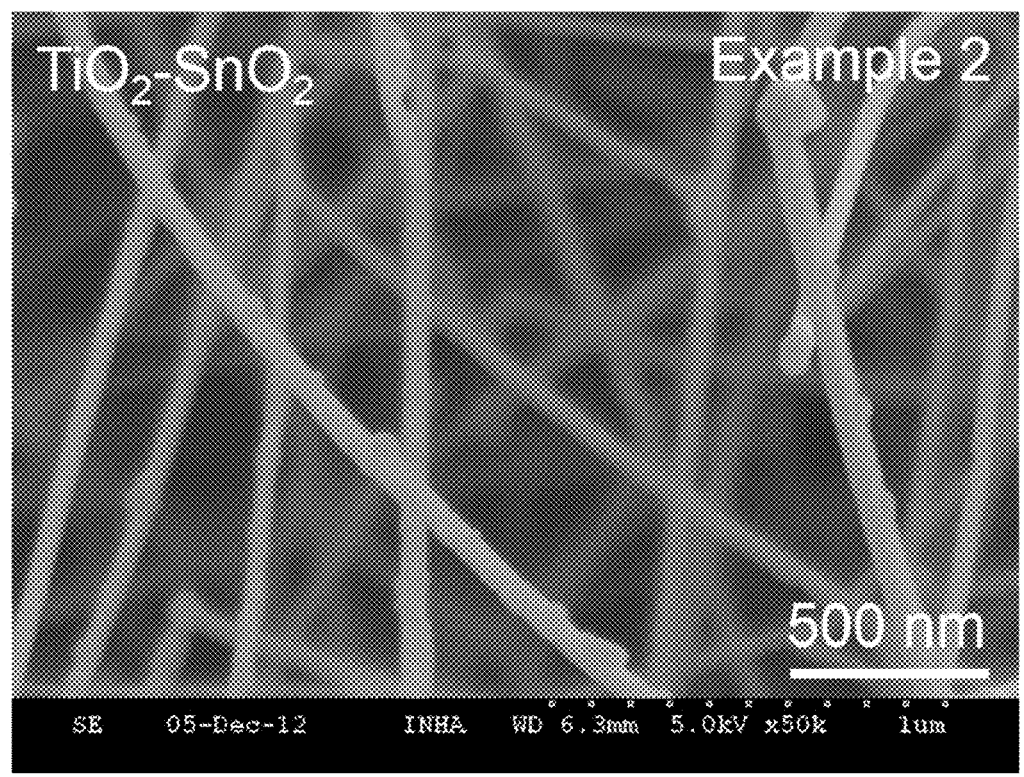
FIG. 13 is a field-emission scanning electron microscope image of a gas sensor prepared in Example 2 according to the present invention.
Figure 14:
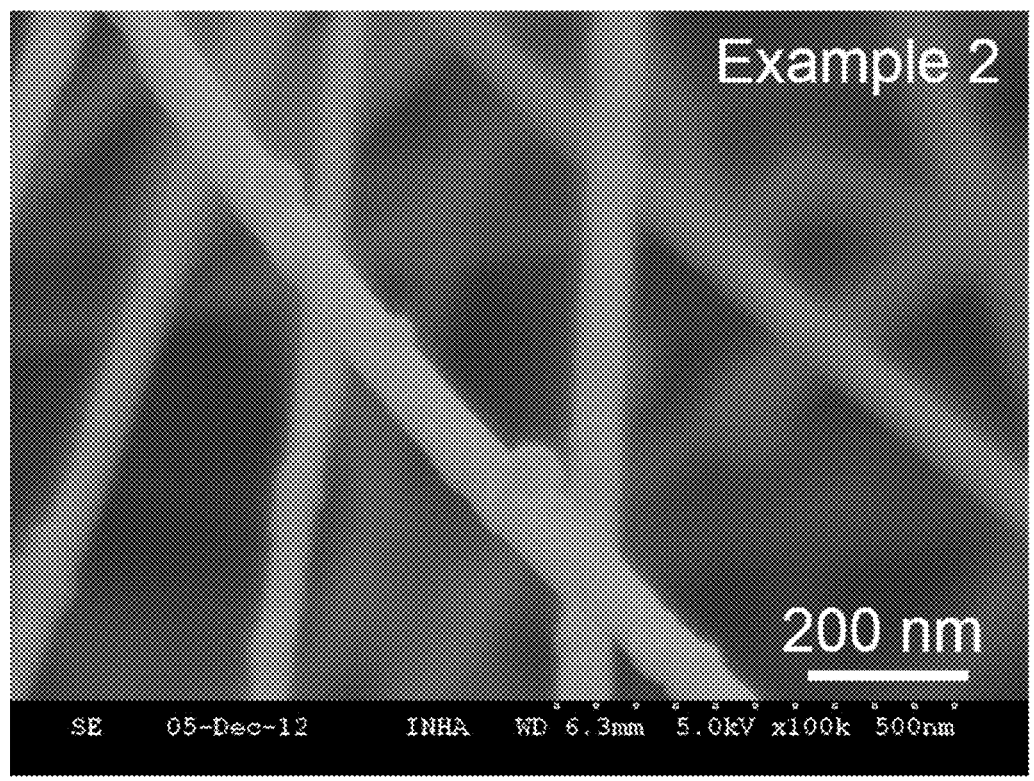
FIG. 14 is a field-emission scanning electron microscope image of a gas sensor prepared in Example 2 according to the present invention.
Figure 15:
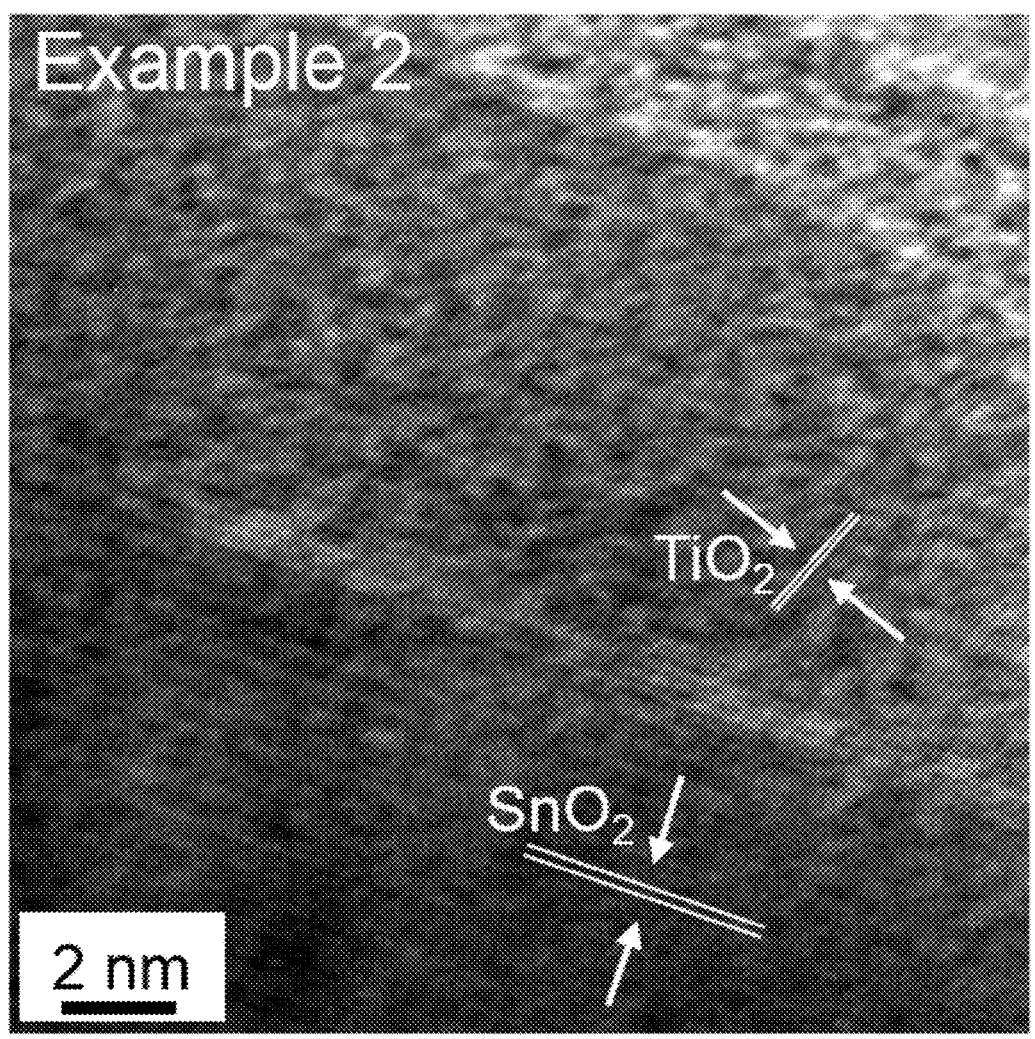
FIG. 15 is a transmission electron microscope/energy dispersive spectroscopy (TEM/EDS) image of a gas sensor prepared in Example 2 according to the present invention.
Figure 16:
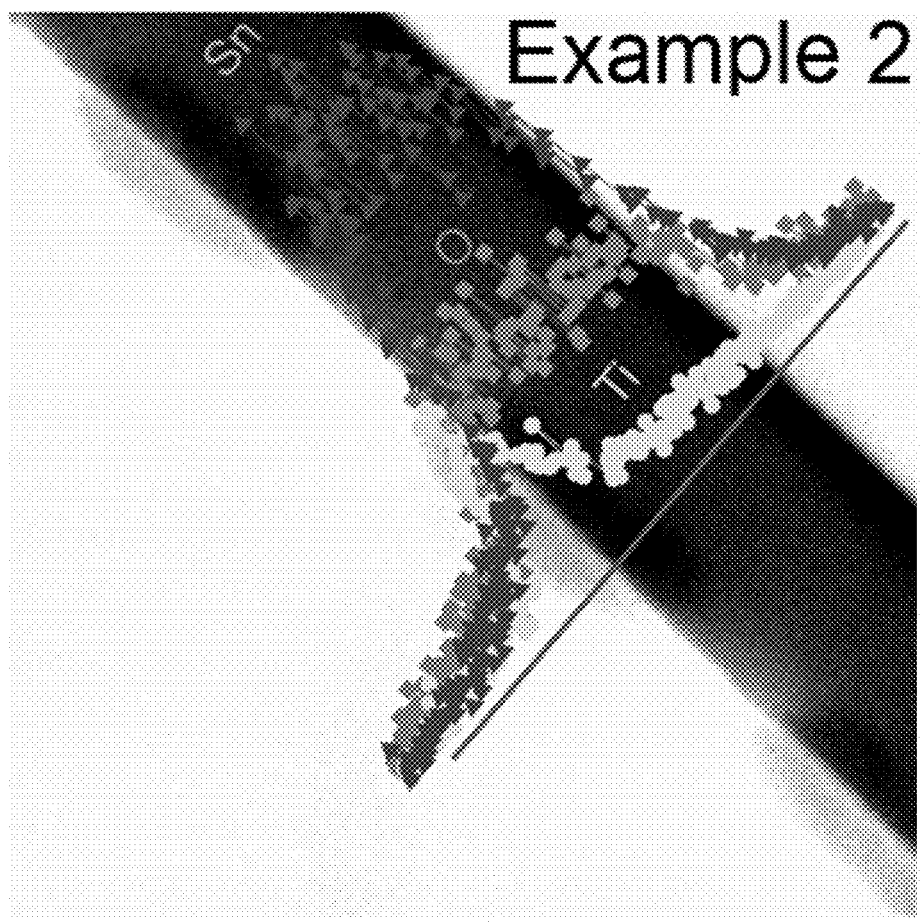
FIG. 16 is a transmission electron microscope/energy dispersive spectroscopy (TEM/EDS) image of a gas sensor prepared in Example 2 according to the present invention.

As shown in FIG. 12, it may be seen that the gas sensor prepared in Example 1 according to the present invention shows that a response with respect to reducing gases such as CO and $H_2$ is 3 times up to 10 times faster than a response with respect to oxidizing gases such as $NO_2$ and $O_2$. Also, it may be seen that the gas sensor may sense even a reducing gas having an infinitesimal concentration of 10 ppm or less with a high sensitivity.

Meanwhile, it may be seen that the gas sensor prepared in Comparative Example 1 shows that a response with respect to an oxidizing gas $NO_2$ is dozens times higher than a response with respect to a reducing gas CO, and especially, it may be seen that a response is very low when an infinitesimal amount of a CO gas not more than 10 ppm exists.

Through this, it has been confirmed that since the gas sensor according to the present invention includes, as gas sensing materials, an n-type oxide semiconductor nanowire and p-type oxide semiconductor nano islands, the gas sensor may sense an infinitesimal amount of a reducing gas with a high sensitivity.

<Experimental Example 2> Analysis 1 of the Gas Sensor Prepared in an n-n Junction Structure by Using a Work Function Difference The following analyses were performed in order to analyze characteristics of the gas sensor prepared in Example 2.

(1) Scanning Electron Microscope and Transmission Electron Microscope Observations In the gas sensor prepared in Example 2, a microstructure of the $SnO_2$ nanowire that is a gas sensing material, was observed by using a scanning electron microscope and a transmission electron microscope (TEM/EDS), and the observed results are shown in FIGS. 13 to 16.

As shown in FIGS. 13 to 16, in the gas sensor prepared in Example 2, it may be seen that $TiO_2$ nano islands are discretely attached to a surface of the $SnO_2$ nanowire that is a gas sensing material.

Through this, it may be confirmed that the gas sensor according to the present invention includes, as gas sensing materials, a nanowire and nano islands that are discretely formed on a surface of a nanowire.

(2) X-Ray Diffraction Analysis

Figure 17:
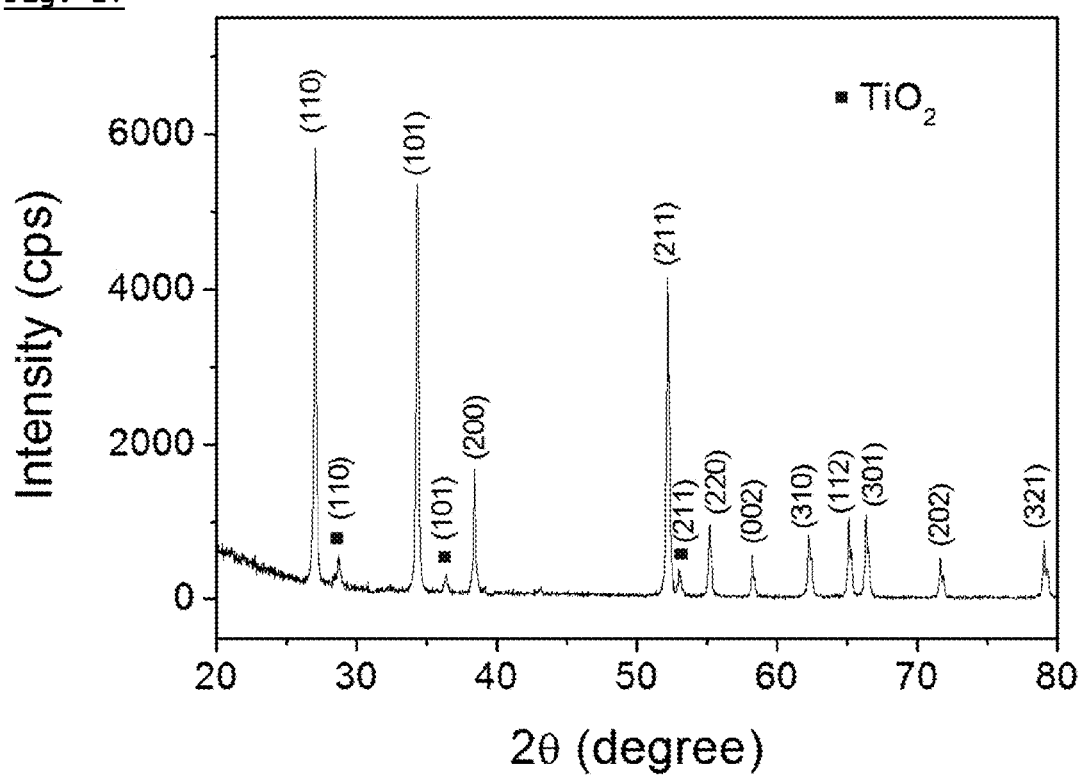
FIG. 17 is a graph showing an X-ray diffraction analysis of a gas sensor prepared in Example 2 according to the present invention.

In the gas sensor prepared in Example 2, a phase analysis was performed by an X-ray diffractometer to analyze a phase of the $SnO_2$ nanowire that is a gas sensing material, and the analyzed results are shown in FIG. 17.

As shown in FIG. 17, it may be seen that a peak corresponding to $TiO_2$ attached on a surface of the $SnO_2$ nanowire that is a gas sensing material, is detected. Also, since $TiO_2$ has a transition temperature at which a phase change occurs, it may be confirmed from a relevant XRD peak result that a rutile phase $TiO_2$ is formed.

(3) Response Analysis According to a Gas Concentration

Figure 18:
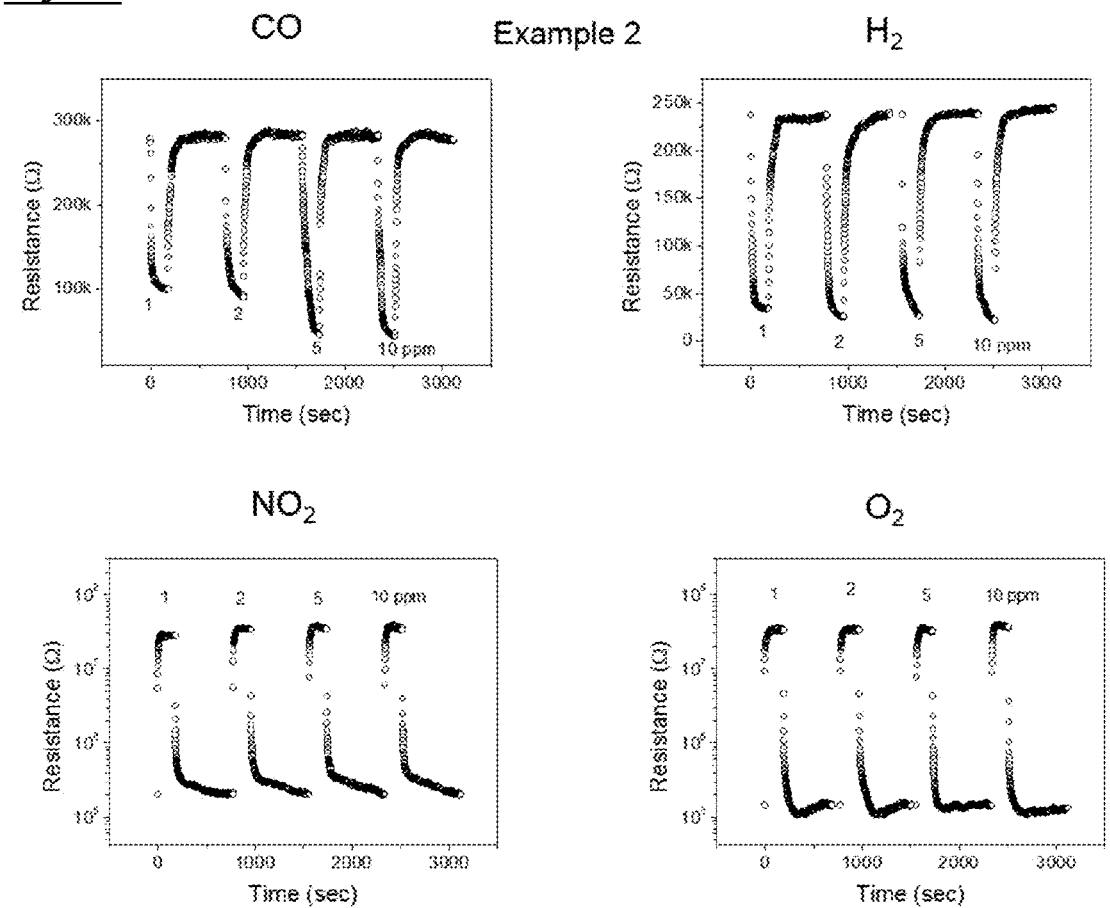
FIG. 18 is a response curve graph showing a sensitivity depending on a concentration of a reaction gas in a gas sensor prepared in Example 2 according to the present invention.
Figure 19:
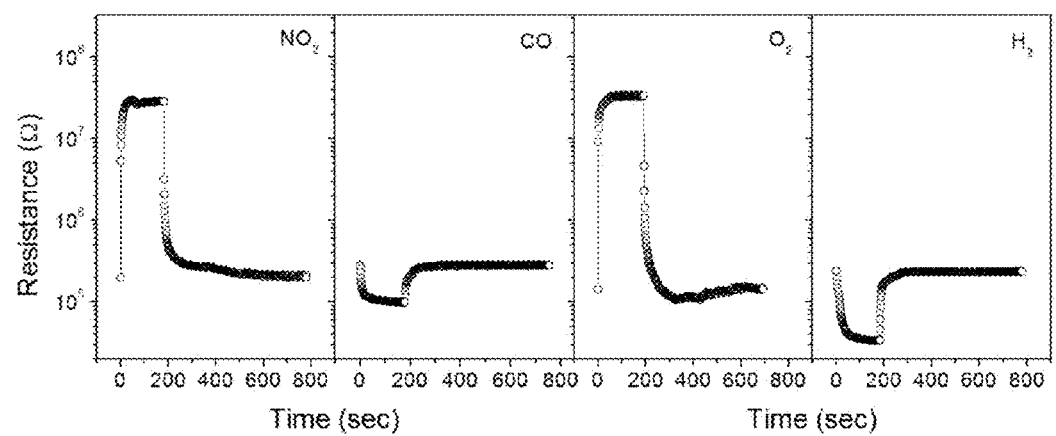
FIG. 19 is a response curve graph showing a sensitivity depending on a concentration of a reaction gas in a gas sensor prepared in Example 2 according to the present invention.

In the gas sensor prepared in Example 2, a resistance change of the sensor was measured by changing a gas concentration of $H_2$, CO, $NO_2$, and $O_2$ in order to analyze a sensitivity according to a gas concentration, the measured results are shown in FIGS. 18 and 19.

As shown in FIG. 18, it may be seen that the gas sensor prepared in Example 2 shows that a resistance change with respect to an oxidizing gas, such as $NO_2$ is greater than a resistance change with respect to a reducing gas such as $H_2$.

Also, as shown in FIG. 19, in comparison of cases of a gas concentration of 1 ppm, as a $TiO_2$ nano islands are formed as the gas sensor prepared in Example 2, an improvement in response with respect to oxidizing gases ($NO_2$ and $O_2$) is considerably greater than an improvement in sensitivity with respect to reducing gases (CO and $H_2$).

(4) Response Analysis According to Existence or Non-Existence of Nano Islands

In order to analyze a response rate of gas sensors prepared in Example 2 and Comparative Example 1 for each response gas, a resistance change of the sensor according to a concentration of $H_2$, CO, $NO_2$, and $O_2$ gases was measured to measure response R.

At this time, a resistance change was measured at a gas concentration of 1 ppm to 50 ppm at a temperature of 300° C. to measure the response R. Also, the response R is defined as R=Rg/Ra or R=Ra/Rg, where Rg represents a resistance value when a reactive gas exists, and Ra represents an initial resistance value when a reactive gas does not exist. The response analysis results are shown in FIG. 20.

Figure 20:
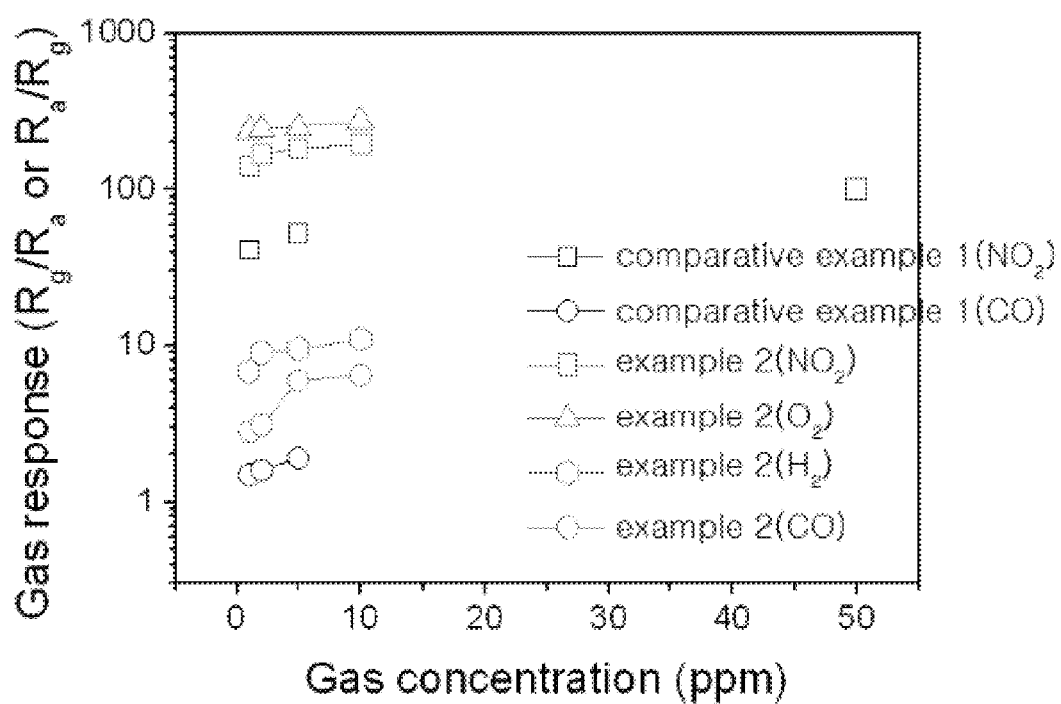
FIG. 20 shows graphs comparing a sensitivity of a gas sensor prepared in Example 2 according to the present invention and a sensitivity of a sensor prepared in Comparative Example 1.

As shown in FIG. 20, it may be seen that the gas sensor prepared in Example 2 is more excellent in response with respect to oxidizing gases ($NO_2$ and $O_2$) than the gas sensor prepared in Comparative Example 1.

<Experimental Example 3> Analysis of the Gas Sensor Prepared in an n-n Junction Structure by Using a Work Function Difference 1

The following analyses were performed in order to analyze characteristics of the gas sensor prepared in Example 3.

(1) Response Analysis According to a Gas Concentration

Figure 21:
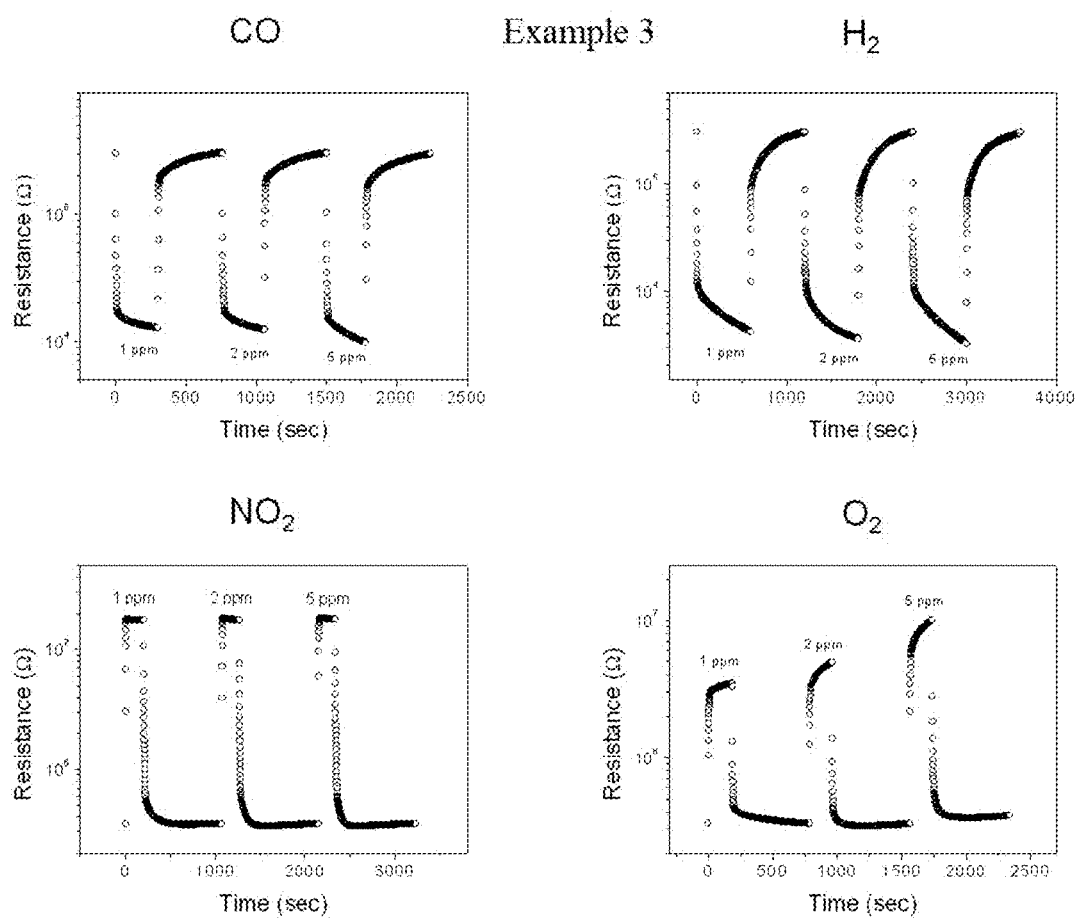
FIG. 21 is a response curve graph showing a sensitivity depending on a concentration of a reaction gas in a gas sensor prepared in Example 3 according to the present invention.
Figure 22:
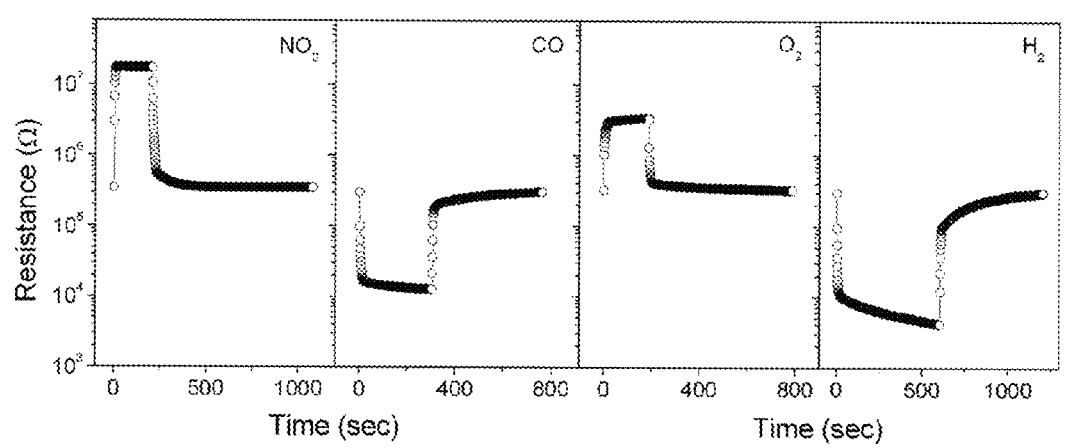
FIG. 22 is a response curve graph showing a sensitivity depending on a concentration of a reaction gas in a gas sensor prepared in Example 3 according to the present invention.

In the gas sensor prepared in Example 3, a resistance change of the sensor was measured by changing a gas concentration of $H_2$, CO, $NO_2$, and $O_2$ in order to analyze a response according to a gas concentration, and the measured results are shown in FIGS. 21 and 22.

As shown in FIG. 21, it may be seen that a resistance change with respect to reducing gases, such as CO and $H_2$ is greater than a resistance change with respect to oxidizing gases such as $NO_2$ and $O_2$.

Also, as shown in FIG. 22, in comparison of cases of a gas concentration of 1 ppm, it may be seen that an improvement in response with respect to reducing gases (CO and $H_2$) is considerably greater than an improvement in response with respect to oxidizing gases ($NO_2$ and $O_2$) due to a formation of the $WO_3$ nano islands.

(2) Response Analysis According to Existence or Non-Existence of Nano Islands

In order to analyze a response rate of gas sensors prepared in Example 3 and Comparative Example 1 for each response gas, a resistance change of the sensor according to a concentration of $H_2$, CO, $NO_2$, and $O_2$ gases was measured to measure response R.

At this time, a resistance change was measured at a gas concentration of 1 ppm to 50 ppm at a temperature of 300° C. to measure the response R. Also, the response R is defined as R=Rg/Ra or R=Ra/Rg, where Rg represents a resistance value when a reactive gas exists, and Ra represents an initial resistance value when a reactive gas does not exist. The response analysis results are shown in FIG. 23.

Figure 23:
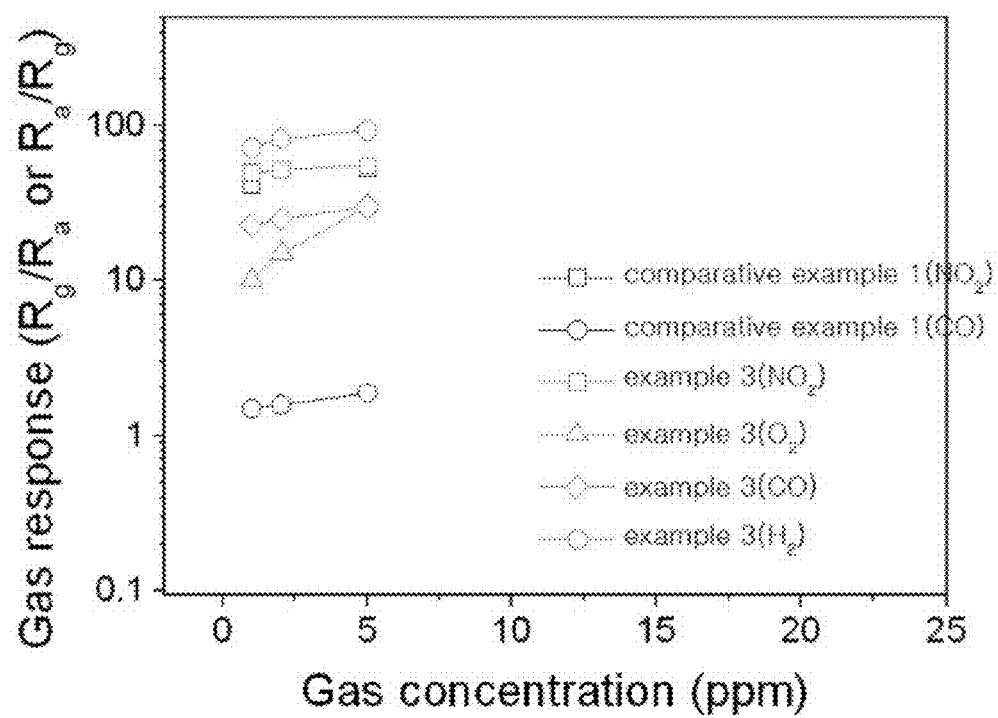
FIG. 23 shows graphs comparing a sensitivity of a gas sensor prepared in Example 3 according to the present invention and a sensitivity of a sensor prepared in Comparative Example 1.

As shown in FIG. 23, it may be seen that the gas sensor prepared in Example 3 according to the present invention has a high response with respect to reducing gases (CO and $H_2$), and especially, has about 20 times higher response than that of the sensor prepared in comparative Example 1 in the case of CO and $H_2$ among reducing gases. Also, it may be seen that the gas sensor may sense even a reducing gas having an infinitesimal concentration of 5 ppm or less with a high sensitivity.

Through this, it has been confirmed that although the gas sensor according to the present invention includes, as gas sensing materials, an n-type oxide semiconductor nanowire and n-type oxide semiconductor nano islands, the gas sensor may sense an infinitesimal amount of a reducing gas with a high sensitivity by using a work function difference.

<Experimental Example 4> Analysis 1 of the Gas Sensor Having a p-n Junction Structure The following analyses were performed in order to analyze characteristics of the gas sensor prepared in Example 4.
(1) Response Analysis According to a Gas Concentration In the gas sensor prepared in Example 4, a resistance change of the sensor was measured by changing a gas concentration of $H_2$, CO, $NO_2$, and $O_2$ in order to analyze a response according to a gas concentration, and the measured results are shown in FIG. 24.

Figure 24:
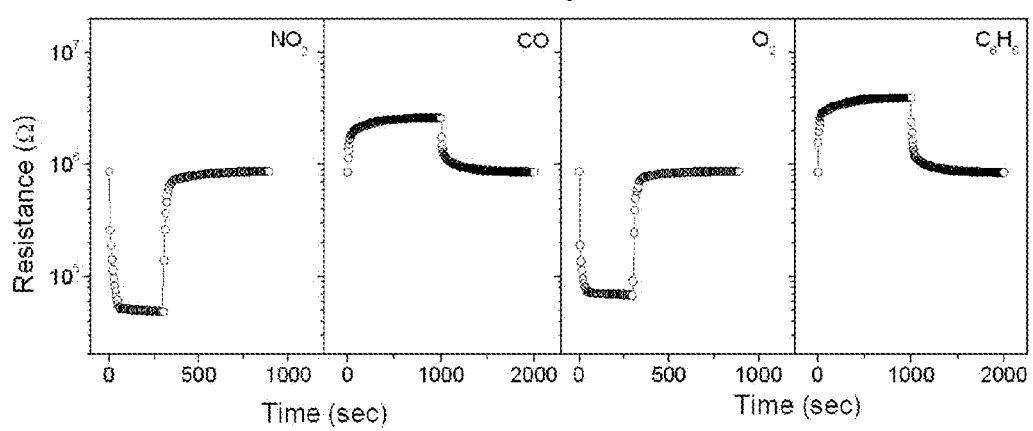
FIG. 24 shows response curve graphs showing a sensitivity to a reaction gas in a gas sensor prepared in Example 4 according to the present invention.

As shown in FIG. 24, in comparison of cases of a gas concentration of 1 ppm, it may be seen that a resistance change with respect to a reducing gas is greater than a resistance change with respect to an oxidizing gas.

(2) Response Analysis According to Existence or Non-Existence of Nano Islands

In order to analyze a response rate of gas sensors prepared in Example 4 and Comparative Example 1 for each response gas, a resistance change of the sensor according to a concentration of $H_2$, CO, $NO_2$, and $O_2$ gases was measured to measure response R.

At this time, a resistance change was measured at a gas concentration of 1 ppm at a temperature of 300° C. to measure the response R. Also, the response R is defined as R=Rg/Ra or R=Ra/Rg, where Rg represents a resistance value when a reactive gas exists, and Ra represents an initial resistance value when a reactive gas does not exist. The response analysis results are shown in FIG. 25.

Figure 25:
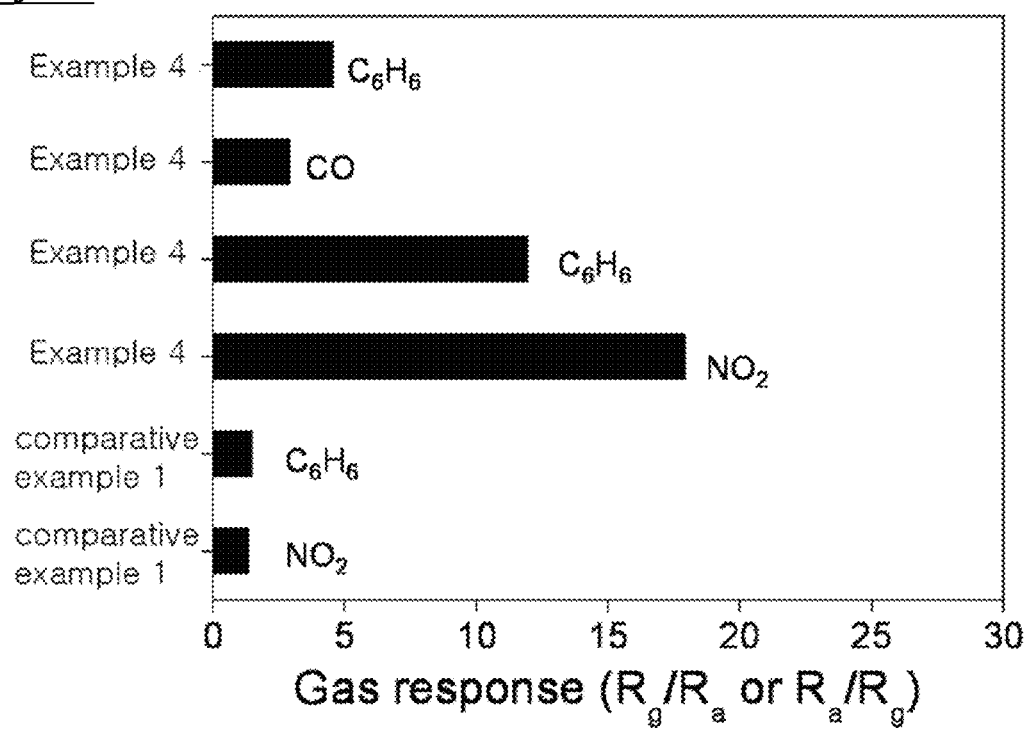
FIG. 25 shows graphs comparing a sensitivity of a gas sensor prepared in Example 4 according to the present invention and a sensitivity of a sensor prepared in Comparative Example 1.

As shown in FIG. 25, it may be seen that the gas sensor prepared in Example 4 shows that a response with respect to oxidizing gases, such as $NO_2$ is higher than a response with respect to a reducing gas such as CO. Also, a response with respect to an oxidizing gas, such as $NO_2$ is 3 times higher compared with the sensor of Comparative Example 1.

Through this, it has been confirmed that as the gas sensor according to the present invention includes, as gas sensing materials, a p-type oxide semiconductor nanowire and n-type oxide semiconductor nano islands, the gas sensor may sense an infinitesimal amount of an oxidizing gas with a high sensitivity.

Specific Example 1

Preparing of CuO—ZnO Core-Shell Nanowire

A CuO—ZnO core-shell nanowire was prepared through a novel two-step process, and through this, a gas sensor was prepared.

First, a CuO core nanowire was synthesized by using an electrospinning method, and then, a ZnO shell layer was deposited by using an ALD method.

Polyvinyl alcohol (PVA) having a molecular weight of 80,000 and copper acetate $(CH_2CO_2)_2Cu$ were used as precursor compounds for synthesizing the CuO core nanowire. For electrospinning, PVA beads were dissolved in diluted water to prepare 9 weight % of a PVA solution. After the PVA solution was stirred at a temperature of 70° C. for 4 hours, the PVA solution was mixed with a copper acetate solution, and the mixed solution was further stirred at a temperature of 70° C. for 6 hours. The viscous copper acetate/PVA solution was loaded inside a glass syringe provided with a 21-gauge stainless steel needle. Nanowires were uniformly electrospun on a $SiO_2$ wafer disposed on a metal collector. The electrospun nanowires were calcinated at a temperature of 600° C. for 48 hours, and at this time, a tube-type furnace was used. In order to minimize a loss of a nanowire under the atmosphere in a laboratory, prepared samples were stored in a dust collection mask and under a vacuum before measurement and characteristic analysis thereof are performed.

A general ALD method was used in order to form a ZnO shell structure on a surface of the CuO core nanowire. In the present Specific Example, an ALD system equipped with a horizontal wall reactor was used. Diethylzinc $(Zn(C_2H_5)_2$, (DEZn)) and $H_2O$ were used as precursors. In order to prevent a violent pre-reaction between the two precursors, DEZn and $H_2O$ were separately introduced into a growth reactor, and a temperature and a pressure of the growth reactor were 150° C. and 0.3 Torr, respectively. DEZn was stored in a bubbler having a temperature of 0° C., and $H_2O$ was stored in a bubbler having a temperature of 10° C. An ALD pulse length was set to 0.12 seconds with respect to DEZn dosing, 3 seconds with respect to $N_2$ purging, and 0.15 seconds with respect to $H_2O$ dosing, and a performing of all the aforementioned processes corresponds to one ALD cycle. The number of the ALD cycle was adjusted between 40 times to 70 times. An average diameter of the CuO core nanowire was about 130 nm, and a thickness of the ZnO shell layer was adjusted to 10 nm to 200 nm.

<Analysis of CuO—ZnO Core-Shell Nanowire>
Analysis Method

A microstructure and a phase of the core-shell nanowire prepared according to the processes were analyzed by using a field emission scanning electron microscope (FE-SEM), a transmission electron microscope (TEM), and an X-ray diffractometer (XRD). Also, an elemental mapping was performed in an energy dispersive spectroscopy (EDS) mode.

Meanwhile, in order to measure the sensor sensitivity, a sensor including the CO—ZnO core-shell nanowire was prepared, and in order to prepare a two-layered electrode of the sensor, Ti and Au were sequentially deposited on a base material at a thickness of about 50 nm and a thickness of about 200 nm, respectively by using a sputtering method and an interdigital electrode mask. A sensor response with respect to a reducing gas, CO was measured at a temperature of 300° C. by using a homemade gas and sensing system. Sensitivity S was calculated according to the following Formula. S=Ra/Rg or Rg/Ra (where Ra corresponds to initial resistance when a gas is not supplied, and Rg corresponds to resistance when a gas to be measured exists). A vapor content inside a CO container was maintained to 3 ppm or less.

Analysis Results

By performing analyses of microstructure, phase, and gas sensitivity of the prepared CuO—ZnO core-shell nanowire, a thickness effect of the ZnO shell layer on the surface of the CuO core nanowire was analyzed, and a heterojunction effect formed on an interface between two different materials was analyzed.

Figure 30A:
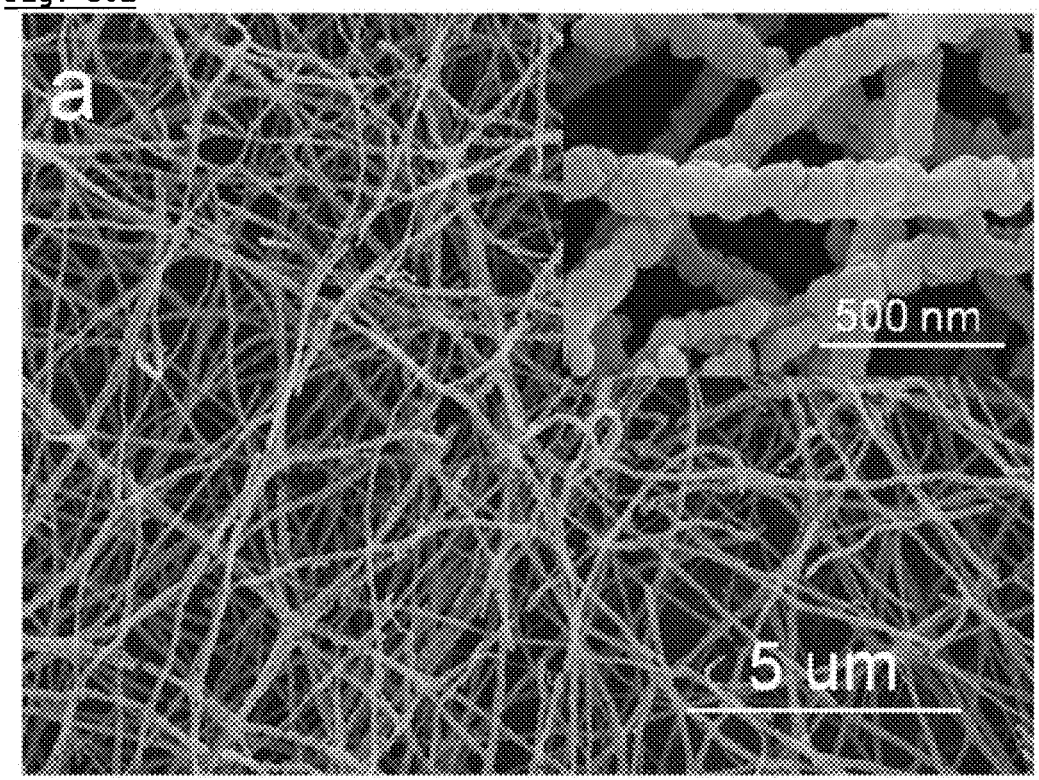
FIG. 30A is a field-emission scanning electron microscope (FE-SEM) image of a CuO core nanowire prepared according to Specific Example 1 of the present invention.
Figure 30B:
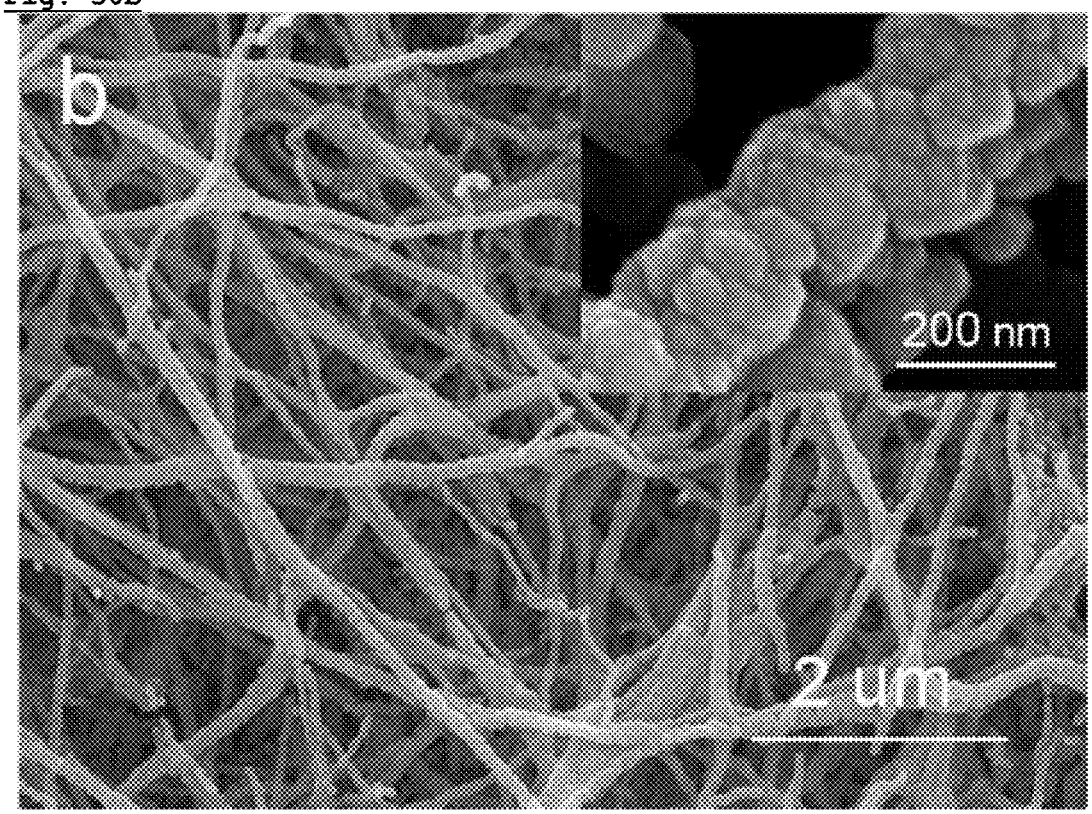
FIG. 30B is a field-emission scanning electron microscope (FE-SEM) image of a CuO—ZnO core-shell nanowire prepared according to Specific Example 1 of the present invention, where an ALD cycle is performed 40 times in order to form a ZnO shell.
Figure 30C:
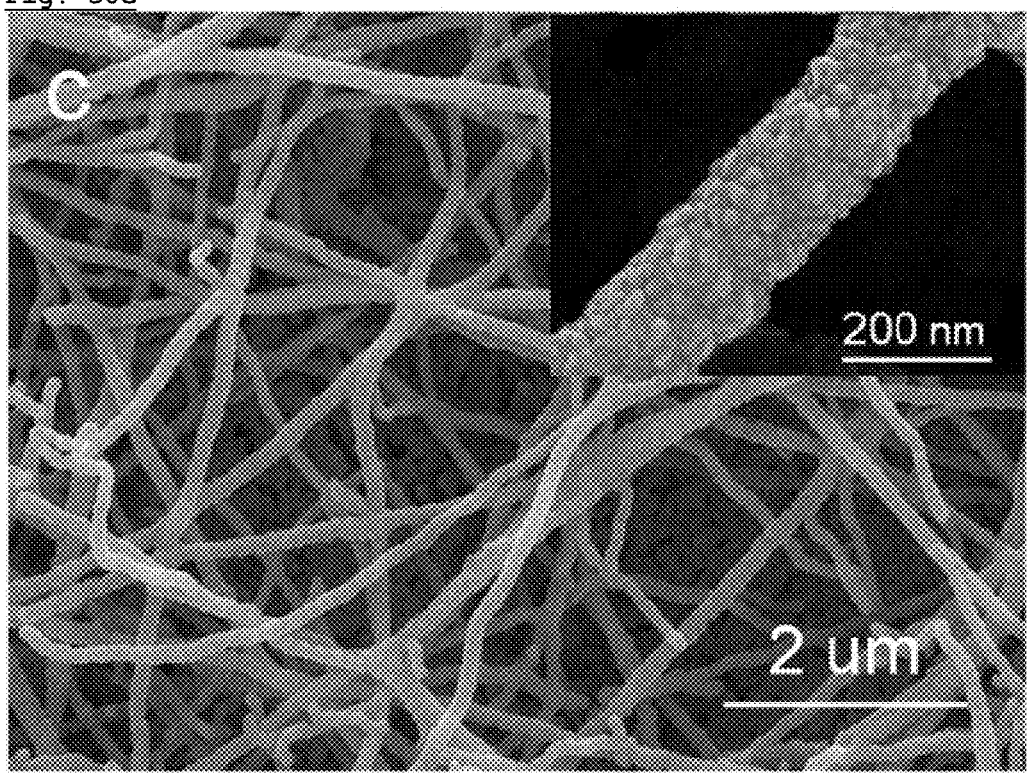
FIG. 30C is a field-emission scanning electron microscope (FE-SEM) image of a CuO—ZnO core-shell nanowire prepared according to Specific Example 1 of the present invention, where an ALD cycle is performed 80 times in order to form a ZnO shell.
Figure 30D:
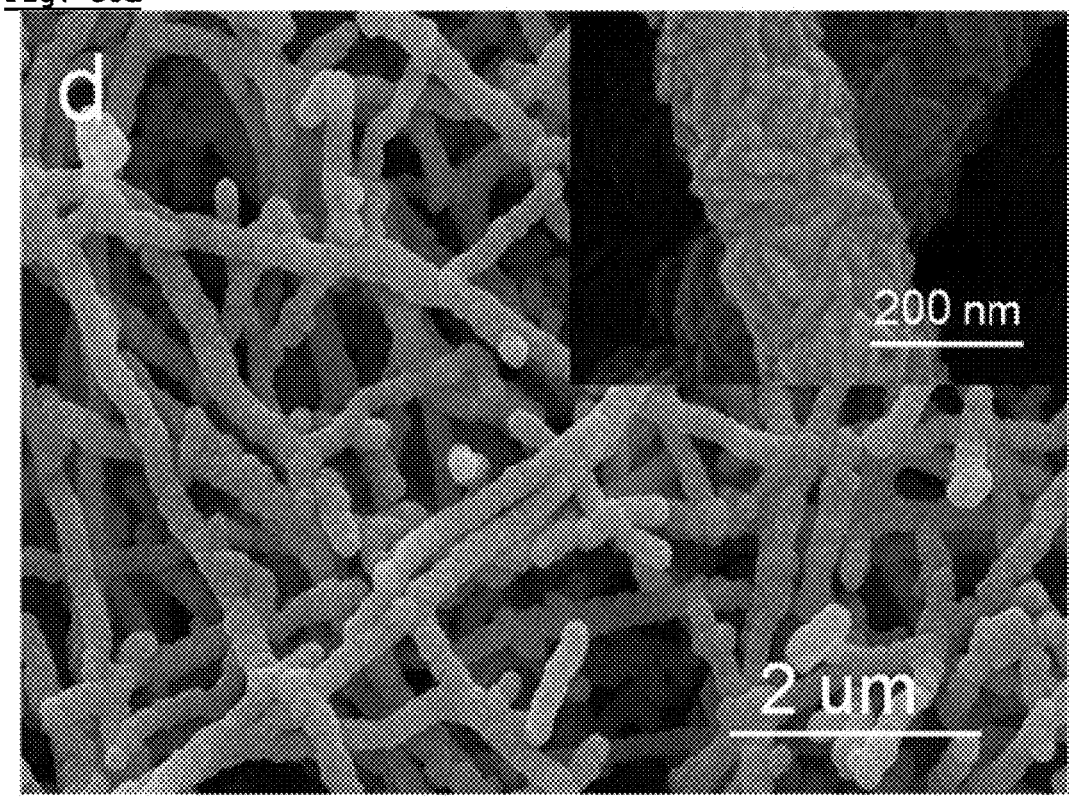
FIG. 30D is a field-emission scanning electron microscope (FE-SEM) image of a CuO—ZnO core-shell nanowire prepared according to Specific Example 1 of the present invention, where an ALD cycle is performed 200 times in order to form a ZnO shell.
Figure 30E:
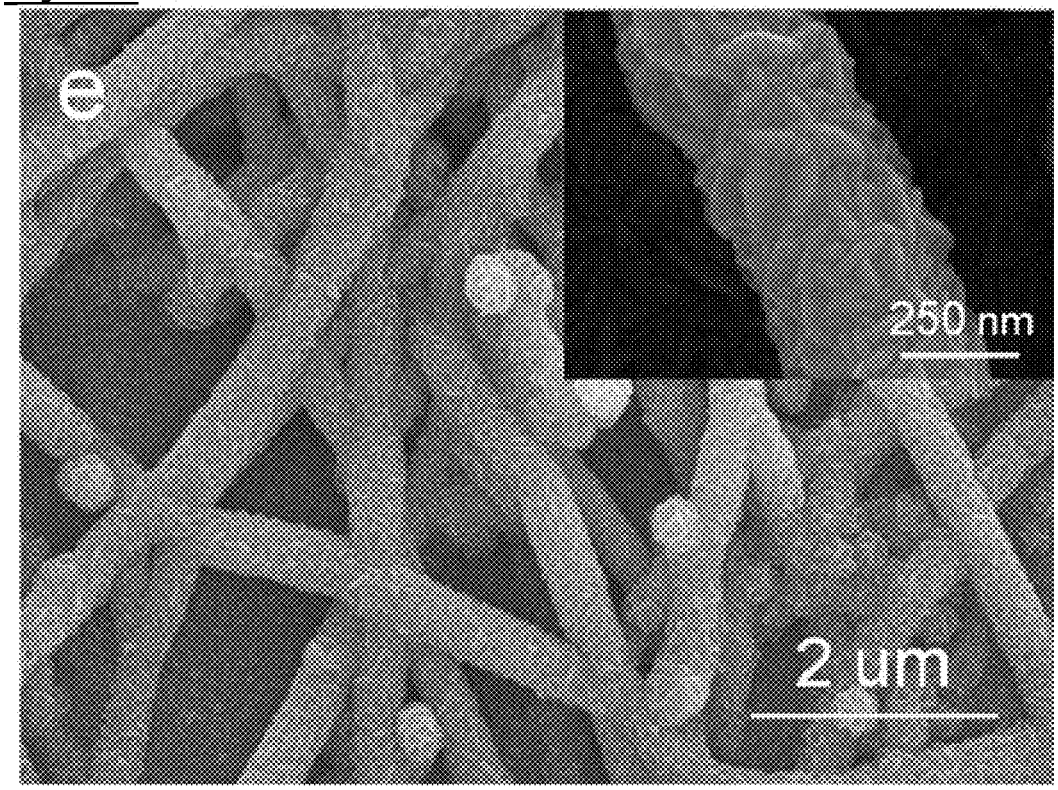
FIG. 30E is a field-emission scanning electron microscope (FE-SEM) image of a CuO—ZnO core-shell nanowire prepared according to Specific Example 1 of the present invention, where an ALD cycle is performed 415 times in order to form a ZnO shell.
Figure 30F:
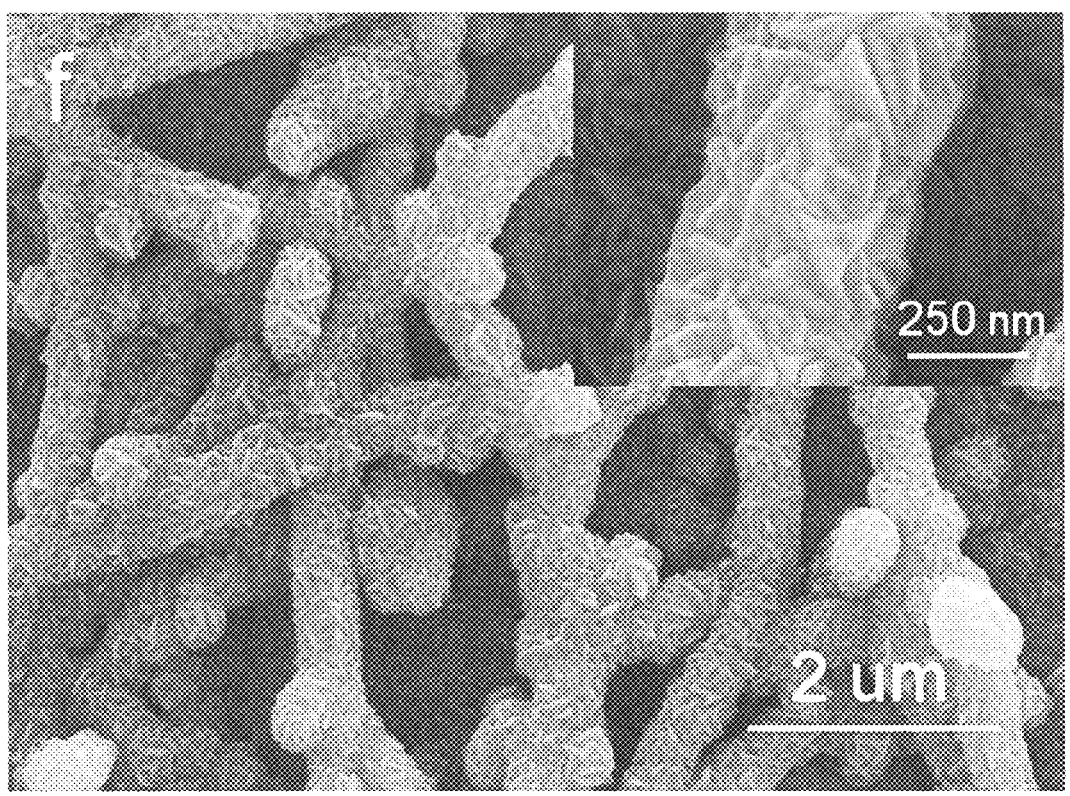
FIG. 30F and is a field-emission scanning electron microscope (FE-SEM) image of a CuO—ZnO core-shell nanowire prepared according to Specific Example 1 of the present invention, where an ALD cycle is performed 667 times in order to form a ZnO shell.

FIG. 30A is a FE-SEM image of CuO core nanowires, which are discretely dispersed on a $SiO_2$ base material, and synthesized through an electrospinning method. Referring to the view of FIG. 30A, it may be apparently confirmed that the CuO core nanowires include nano-sized particles. A ZnO shell layer was deposited on the CuO core nanowire through an ALD method. FIGS. 30B to 30F show FE-SEM images of CuO core-shell nanowires prepared by changing the number of an ALD cycle, and the ALD cycle was repeated 40 times, 80 times, 200 times, 415 times, and 667 times in FIGS. 30B to 30F, respectively in order to form a ZnO shell. Referring to FIGS. 30B to 30F, large size particles forming the CuO core nanowires, and small size particles forming the ZnO shell layer deposited on the CuO core nanowires were apparently distinguished. It is estimated that particles on the shell layer protrude from surfaces thereof to form a rough surface, the rough surface provides an adsorption space when gas molecules are introduced, and thus the rough surface may improve adsorption performance of the sensor. Meanwhile, the heterojunction, which is formed between two different materials, generates a potential barrier on an interface of the two different materials, and forms a path through which electrons penetrate to improve a gas sensitivity.

Figure 31:
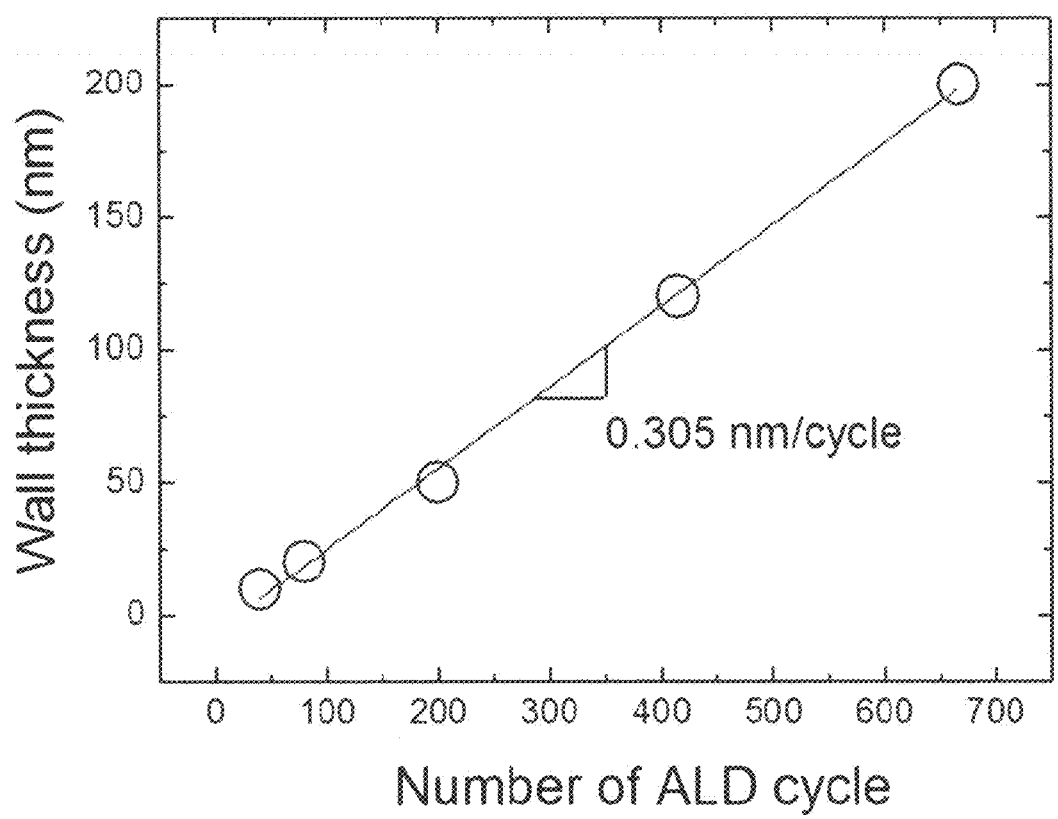
FIG. 31 is a graph showing that when a core-shell nanostructure is prepared according to Specific Example 1 of the present invention, a thickness of the shell is gradually increased in linear proportion to the number of an ALD cycle.

FIG. 31 relates to a ZnO shell thickness of a core-shell nanowire. As the number of the ALD cycle was increased, the ZnO shell thickness was gradually increased. The increment of ZnO shell thickness according to the increment of the number of the ALD cycle appeared to be nearly linear. A forming rate of the ZnO shell layer was calculated at a rate of 0.305 nm/ALD cycle from a gradient of a graph, and from this, it has confirmed that the shell thickness may be adjusted to a nanometer scale level by adjusting the number of the ALD cycle.

Figure 32A:
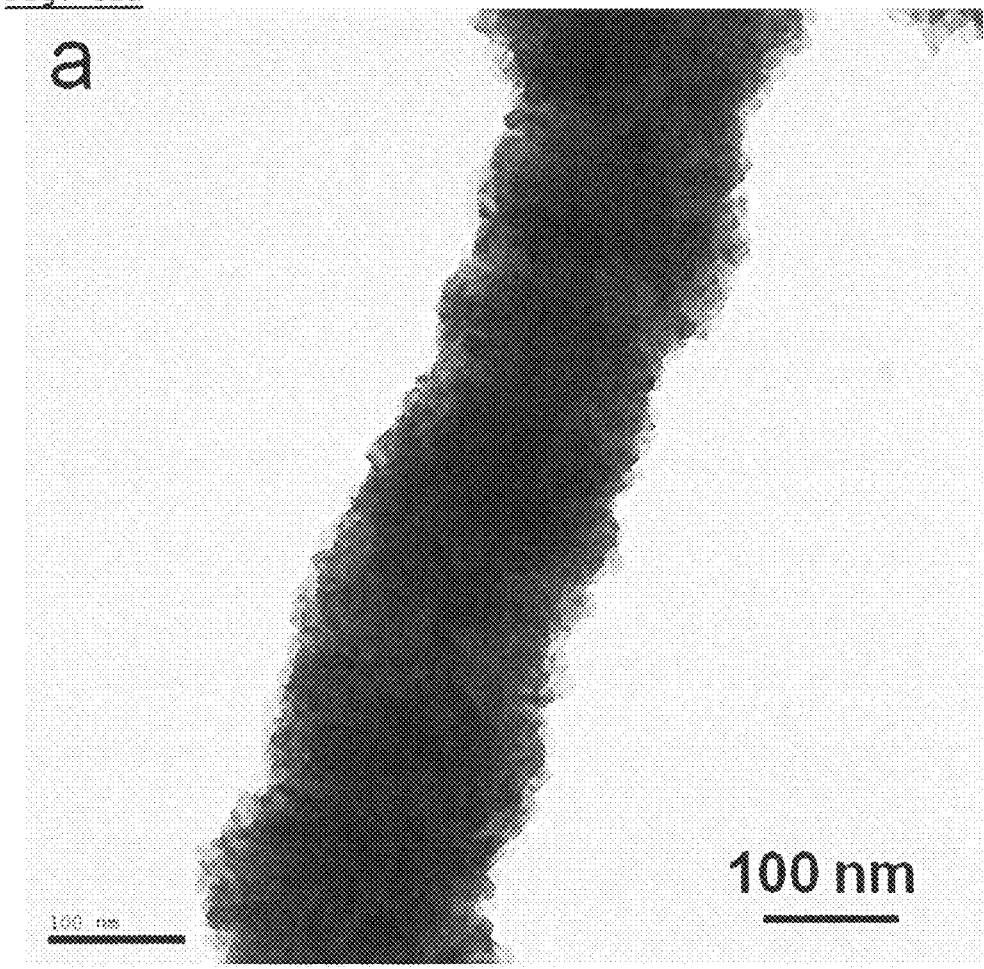
FIG. 32A is a low magnification transmission electron microscope image of a core-shell nanowire having a ZnO shell thickness of 5 nm which is prepared according to Specific Example 1 of the present invention.
Figure 32B:
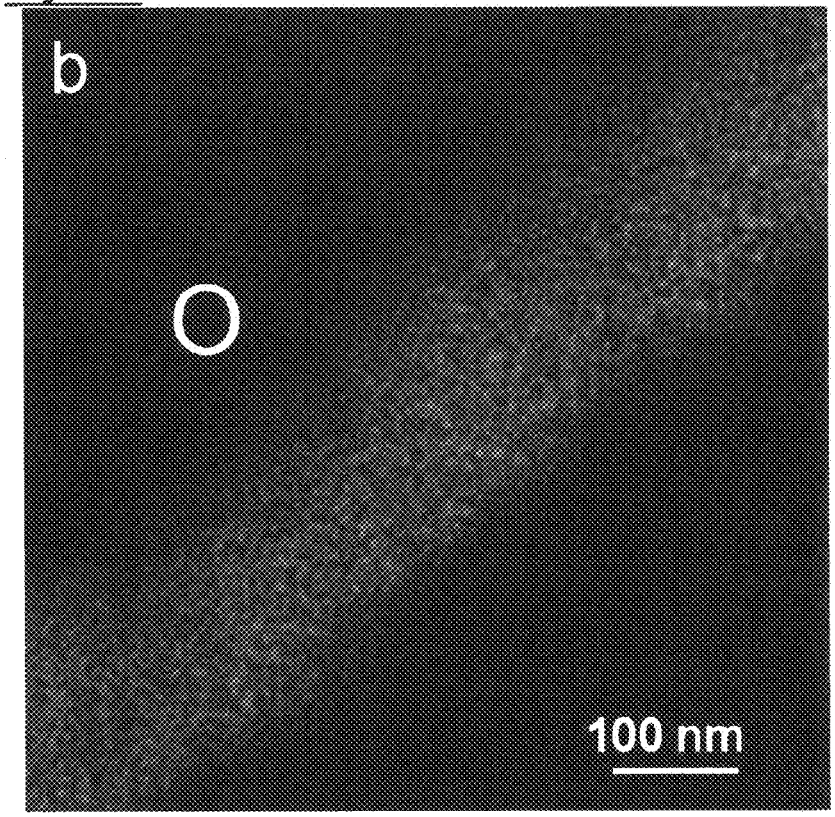
FIG. 32B is an elemental mapping profile of O of the core-shell nanowire.
Figure 32C:
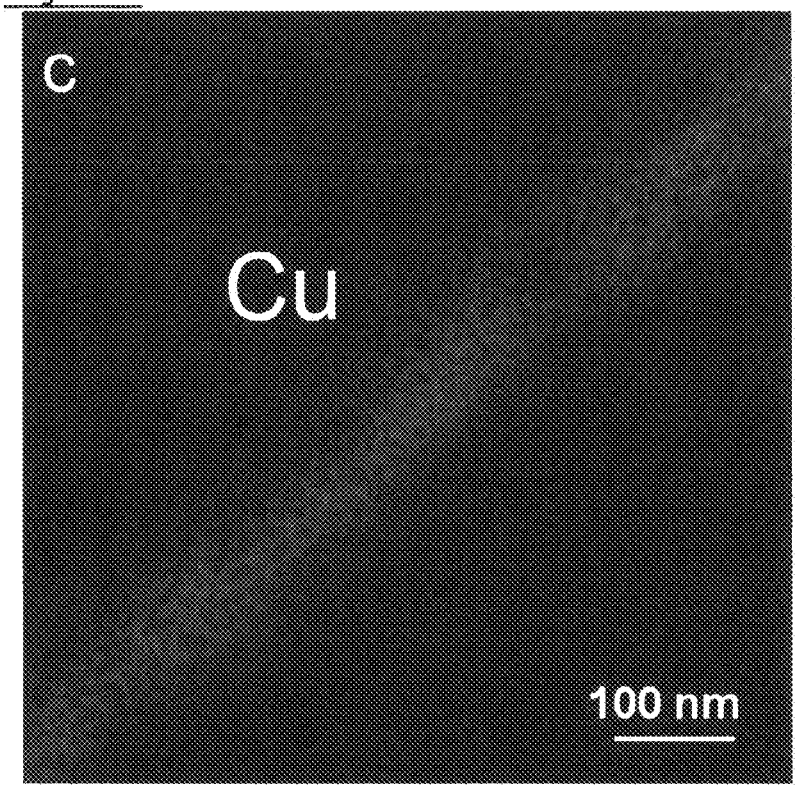
FIG. 32C is an elemental mapping profile of Cu of the core-shell nanowire.
Figure 32D:
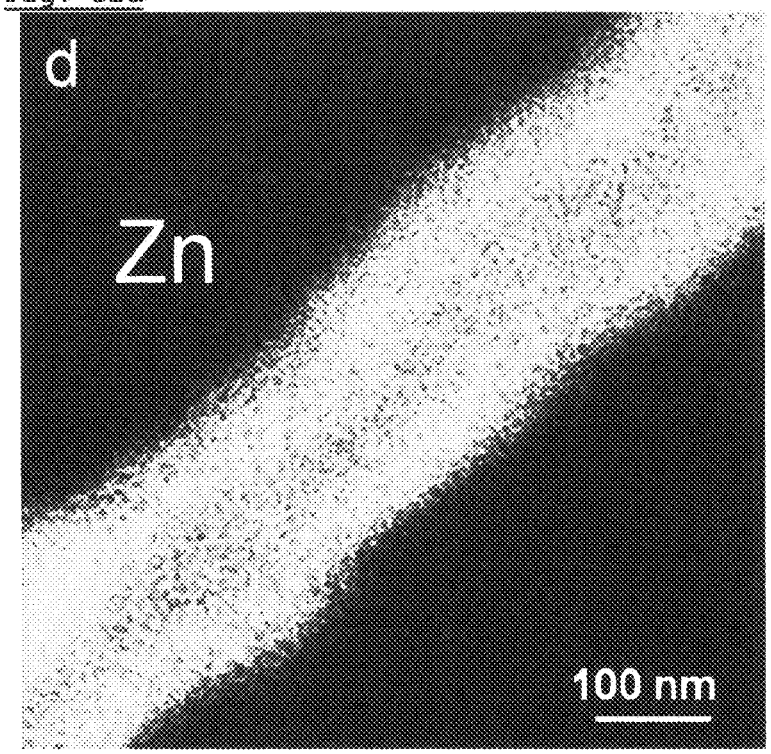
FIG. 32D is an elemental mapping profile of Zn of the core-shell nanowire.
Figure 32E:
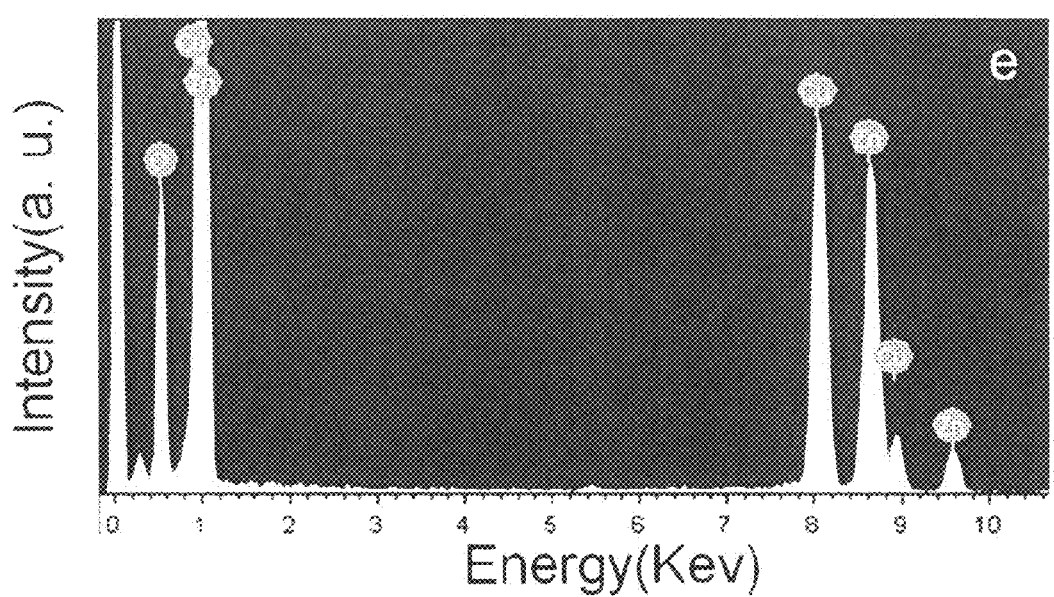
FIG. 32E is a graph showing a chemical composition of the core-shell nanowire analyzed by using an energy-dispersive spectroscopy (EDS)

The microstructure of the core-shell nanowire was additionally analyzed by using a TEM. FIG. 32A is a low magnification TEM image of a core-shell nanowire having a ZnO shell thickness of 5 nm. FIGS. 32B and 32D are elemental mapping profiles of O, Cu, and Zn of the CuO—ZnO core-shell nanowire, respectively, and FIG. 32E is a graph showing a chemical composition of the CuO—ZnO core-shell nanowire analyzed by using an EDS. It has been confirmed that in the core-shell nanowire, Zn is concentrated on an outer surface of the nanowire, and Cu is concentrated inside the nanowire through results of FIGS. 32A to 32E, and accordingly, it has been confirmed that elements, such as O, Cu, and Zn are apparently spatially separated. It has been confirmed from the elemental mapping analysis results that a core-shell nanowire having a shell thickness of 50 nm is formed, and it has been confirmed from the EDS analysis results that ZnO exists on a surface of the core-shell nanowire, and CuO exists in a core.

FIG. 33 shows XRD patterns of a CuO nanowire and a CuO—ZnO core-shell nanowire. The XRD pattern of the CuO nanowire was confirmed for the sake of comparison. CuO—ZnO core-shell nanowires, which have shell thicknesses of 10 nm, 20 nm, 50 nm, 120 nm, and 200 nm, respectively, showed a diffraction peak corresponding to a ZnO phase in addition to a peak by a CuO phase, and from this, it has been again confirmed that the ZnO shell layer is formed on the CuO core nanowire. Increased intensity of the XRD peak was proportional to an increased thickness of the ZnO shell layer formed on the CuO nanowire.

Figure 34A:
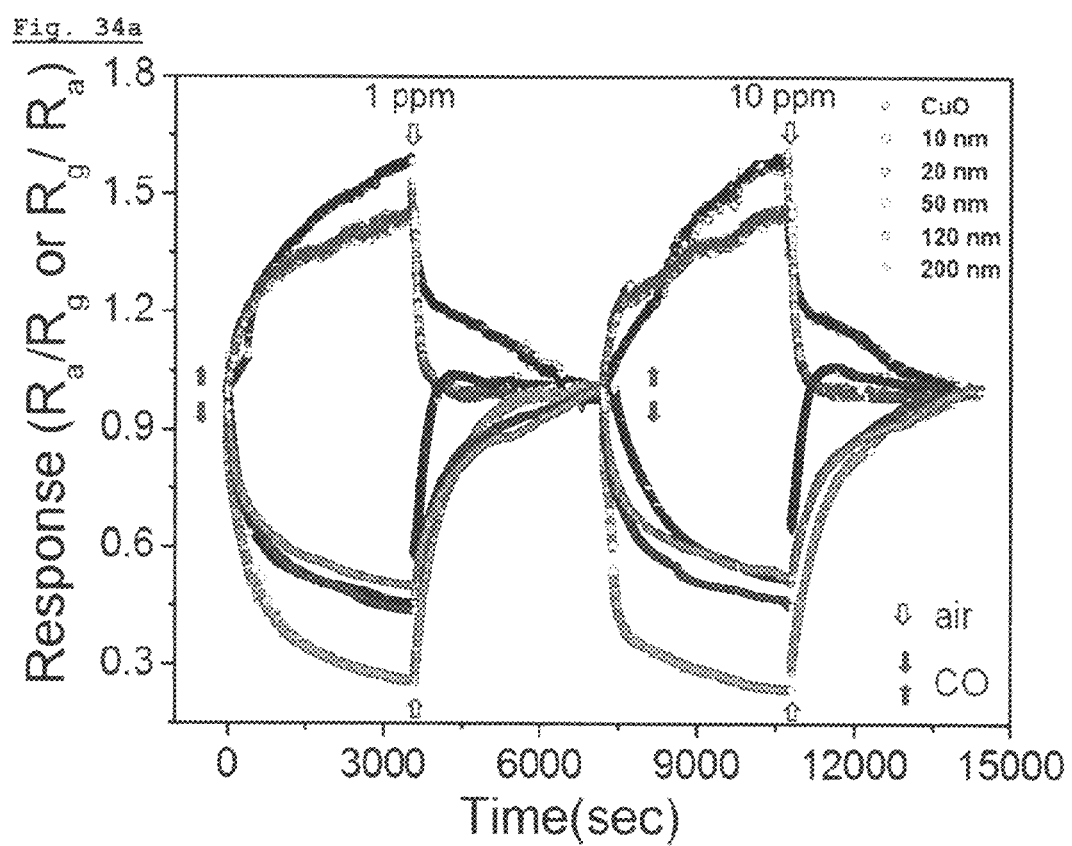
FIG. 34A shows response curves to a CO gas of each of a CuO—ZnO core-shell nanowire prepared so as to have various thicknesses according to Specific Example 1 of the present invention, and a comparison group of a CuO nanowire.

In order to confirm sensitivities with respect to respective gases in the CuO nanowire and the CuO—ZnO core-shell nanowires having various thicknesses, the experiment was performed under an atmosphere of a concentration of 1 ppm to 10 ppm of CO. All sensor responses occurred according to a concentration change of CO. FIG. 34A is a graph showing CO gas response curves of sensors including a CuO nanowire and a CuO—ZnO core-shell nanowire, respectively at a temperature of 300° C. It has been observed that the sensor including the core-shell nanowire shows a response difference from that of the sensor including the CuO nanowire. The CuO nanowire has shown an aspect that a p-type response thereof is converted into an n-type response according to increment of a ZnO thickness of the CuO—Zno core-shell nanowire.

Figure 34B:
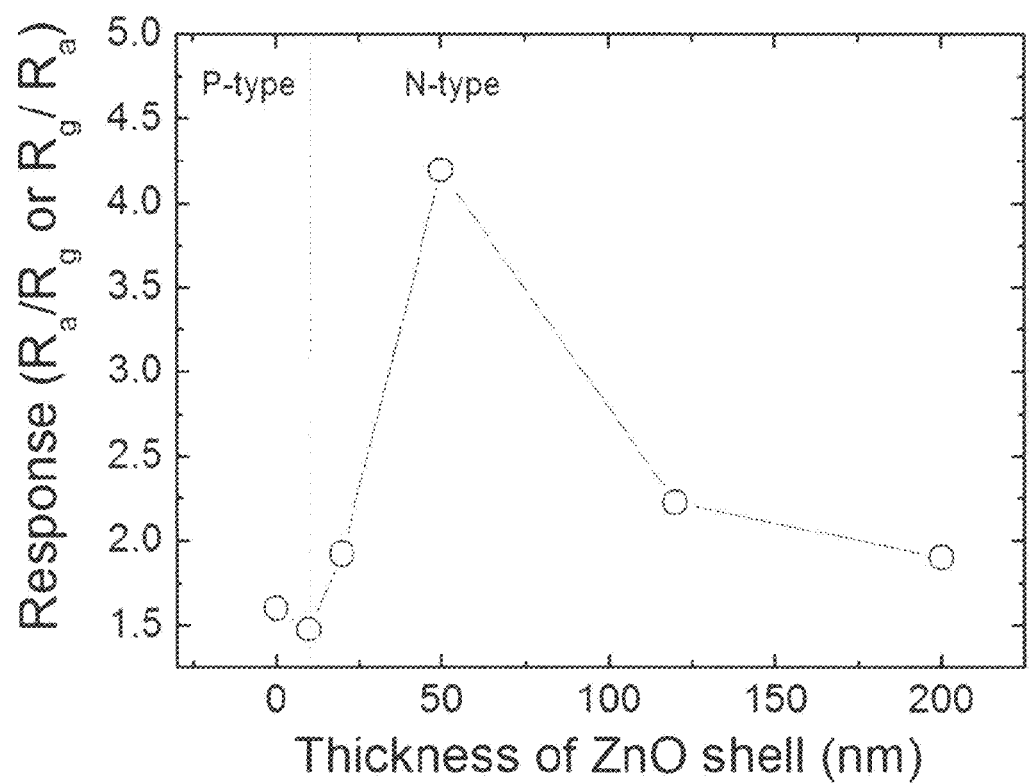
FIG. 34B is a graph expressing data of FIG. 34A in a different way.

A response of the sensor including the CuO nanowire was increased when the sensor was exposed to a CO gas, but the response was decreased when the sensor was exposed to the atmosphere, which showed a typical p-type response. Meanwhile, a response of the core-shell nanowire having a ZnO shell thickness of 10 nm was more decreased, which showed the n-type response of the ZnO shell layer. Referring to FIG. 34B, in a case of the core-shell nanowire having a shell thickness of 10 nm, it is estimated that a surface of the CuO nanowire is not uniformly applied with the ZnO shell layer. Also, when the sensor is exposed to a gas, it is estimated that gas molecules are diffused through a channel formed between ZnO particles existing on a surface of the CuO nanowire. All the CuO core and the ZnO shell respond to a CO gas, the n-type response of the ZnO eventually reduces the p-type response of the CuO nanowire. Since the sensor is exposed to the CO gas, and accordingly, conductivity of an n-type material is increased, it has been expected that response is decreased. A gas response of the ZnO—CuO core-shell nanowire appears similarly under a CO atmosphere, and this is because the p-type CuO added to the n-type ZnO reduces the response due to a decrease in conductivity of the p-type CuO under the CO atmosphere.

Meanwhile, in the case of the core-shell nanowire having a shell thickness of 10 nm or more, the core-shell nanowire was sufficiently applied with particles of the ZnO shell layer. While resistance of the sensor was reduced under a CO atmosphere, the resistance of the sensor was increased under the atmosphere. When the core-shell nanowire is exposed to a CO gas, CO gas molecules produces the following reaction with oxygen adsorbed to a surface of ZnO: $[CO+O_2^- \rightarrow CO_2+2e^-]$. Therefore, free electrons reduce resistance. Meanwhile, when the supply of the CO gas is cut off, oxygen molecules in the atmosphere are adsorbed to a surface of a nanowire, and accordingly, resistance is increased due to the electron adsorption of the nanowire. FIG. 34B relates to a relative response of the core-shell nanowire. A sensor including a core-shell nanowire having a shell thickness of about 50 nm showed a high response of about 4.2 in comparison with other sensors. A sensor including a core-shell nanowire having a shell thickness of 20 nm showed a relatively low response of about 1.9 in comparison with a case of a shell thickness of 50 nm, and showed an n-type response, and from this, it has been re-confirmed a possibility that CO gas particles may be diffused through a channel formed between ZnO particles disposed on a surface of the CuO nanowire. When the shell thickness of the core-shell nanowire is a Debye length, gas particles may extract electrons from a core. When the shell thickness of the core-shell nanowire is 10 nm or less, a p-type response appeared, but when the shell thickness excesses 10 nm, an n-type response appeared. The all analysis results described above supported that the ZnO shell thickness in the core-shell nanowire functioned as a major factor in response of the sensor.

Figure 35A:
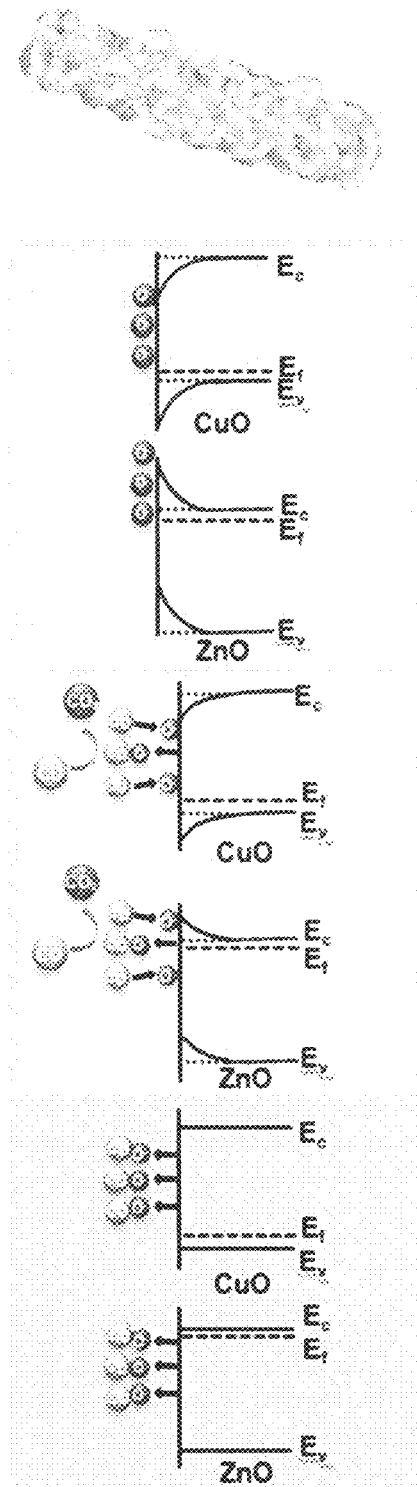
FIG. 35A is a schematic view illustrating nanostructures prepared according to Specific Example 1 of the present invention so as to be used as a sensing part of a sensor, in which an electron transfer, a conduction band energy level EC, and a Fermi energy level EF are schematically illustrated, and in particular, FIG. 35A corresponds to a case that the nanostructure is a comparison group of a CuO nanowire.
Figure 35B:
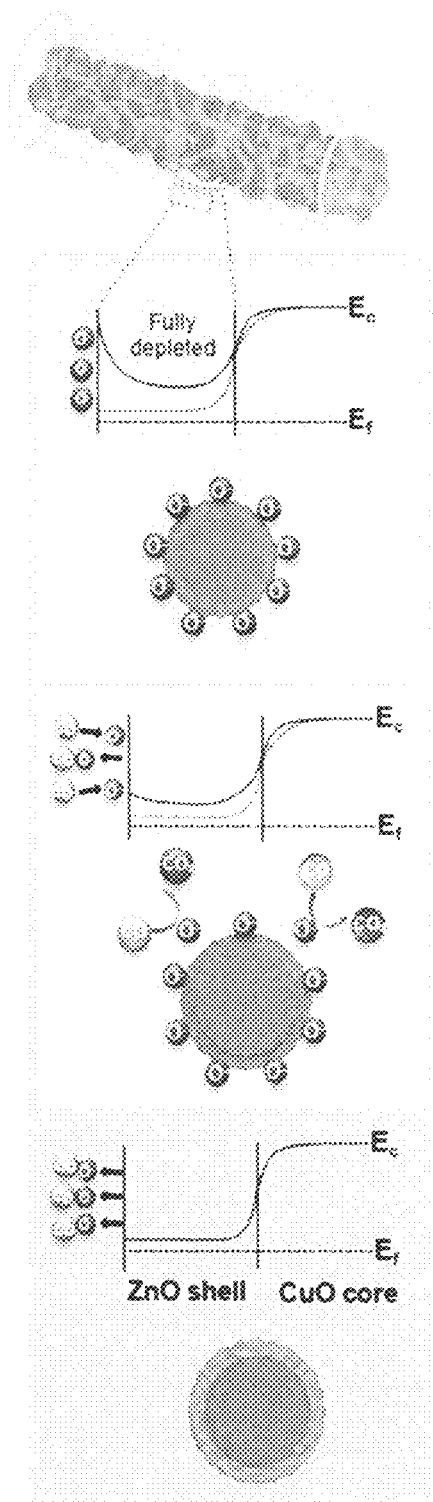
FIG. 35B is a schematic view illustrating nanostructures prepared according to Specific Example 1 of the present invention so as to be used as a sensing part of a sensor, in which an electron transfer, a conduction band energy level EC, and a Fermi energy level EF are schematically illustrated, and in particular, FIG. 35B corresponds to a case that the nanostructure is a CuO—ZnO core-shell nanowire in which a fully depleted layer is formed.
Figure 35C:
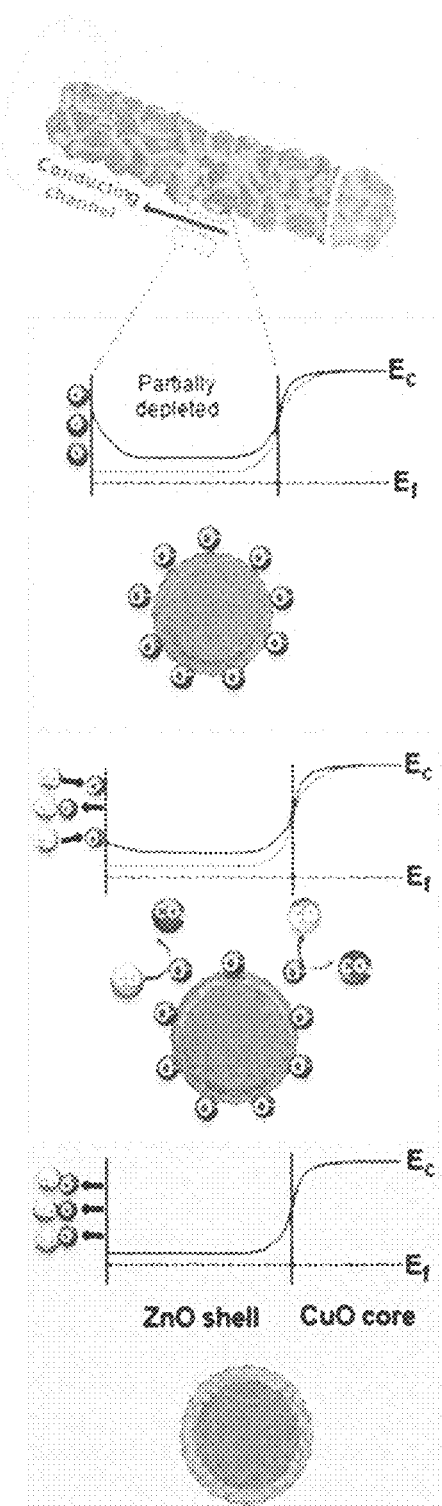
FIG. 35C is a schematic view illustrating nanostructures prepared according to Specific Example 1 of the present invention so as to be used as a sensing part of a sensor, in which an electron transfer, a conduction band energy level EC, and a Fermi energy level EF are schematically illustrated, and in particular, FIG. 35C corresponds to a case that the nanostructure is a CuO—ZnO core-shell nanowire in which a partially depleted layer is formed, respectively.

A response mechanism with the respect to a gas in the core-shell nanowire is related to a depletion layer formed on the shell layer due to electron adsorption of a gaseous chemical species chemically adsorbed and a heterojunction formed between the shell layer and the core nanowire. In this regard, FIGS. 35A to 35C are schematic views illustrating a nanostructure prepared according to the present Specific Example so as to be used as a sensing part of a sensor, and schematic views illustrating an electron transfer, a conduction band energy level EC, and a Fermi energy level EF, in case that the nanostructure is a comparison group of a CuO nanowire, in case that the nanostructure is a CuO—ZnO core-shell nanowire in which a fully depleted layer is formed, and in case that the nanostructure is a CuO—ZnO core-shell nanowire in which a partially depleted layer is formed, respectively. In a core-shell nanowire having a shell thickness of 10 nm, adsorption of oxygen molecules occurred on all surfaces of a ZnO shell layer and CuO, and it has been estimated that oxygen molecules will be diffused along a channel formed between small particles of the ZnO shell layer. FIG. 35A showed a relative band bending. Meanwhile, in a core-shell nanowire having a shell thickness of 50 nm, a fully depleted layer was formed on the shell layer by complex effects such as a band bending on a surface of the ZnO shell layer due to adsorption of an oxygen chemical species and a band bending on a heterojunction formed between the ZnO shell layer and the CuO core nanowire. Under the atmosphere, inner defects such as oxygen vacancy on a surface of the n-type ZnO shell layer, is utilized as an adsorption site of oxygen molecules. Free electrons inside the ZnO shell layer are removed by the adsorbed oxygen molecules through the following reaction: $[O_2(g)+e^- \rightarrow O_2^-$ (Adsorption)]. Reduction under free charge density inside the ZnO shell depletes a surface charge state, and generates a space charge region. Resultantly, the band bending occurs on a surface of the ZnO shell layer. A thickness of a depletion layer by the adsorption, which is calculated by the following Mathematical Equation 1, was about 69 nm.

$$d = \sqrt{\frac{2\varepsilon_{ZnO}\varepsilon_0 \Phi_S}{e^2 N_D^+(T)}} \quad \text{[Mathematical Equation 1]}$$

In Mathematical Equation 1, $\varepsilon_{ZnO}$ is a relative dielectric constant value, in which the value is about 8.7, $\varepsilon_0$ is permittivity of vacuum, e is an electronic charge, $N_D^+(T)$ is a donor concentration at room temperature, in which the concentration is about $10^{17}$ cm$^{-3}$, and $\Phi$ is a potential barrier height, in which the value is 0.5 eV.

ZnO—CuO is a p-n isotope heterojunction. The band bending inside the ZnO—CuO hetero structure may be evaluated on the basis of an energy band structure thereof. Electron affinity ($\chi$), a band gap (Eg)m and a work function (W) of ZnO and CuO are required for analyzing an energy band structure, and $\chi$ZnO and $\chi$CuO are 4.29 eV and 4.07 eV, respectively, Eg, ZnO and Eg, CuO are 3.3 eV and 1.35 eV, respectively, and WZnO and WCuO are 4.45 eV and 5.2 eV, respectively. A band bending occurs while a heterojunction between ZnO and CuO is formed, and the results are schematically shown on a bottom of FIGS. 35B and 35C. In this case, a difference between WZnO and WCuO caused a built-in-potential on an interface between ZnO and CuO, and the built-in potential was 0.75 eV. A depletion layer with (Wd) in the heterojunction may be calculated from Mathematical Equation q by substituting the built-in potential of 0.75 eV for $\Phi$s. The calculated Wd was about 85 nm. Resultantly, as schematically shown in FIGS. 35B and 35C, widths of the depletion layers, which are formed on a surface and a heterojunction, are substantially about 69 nm and 85 nm, respectively, and when the ZnO shell thickness is up to 50 nm, a fully depleted layer was formed, and when the ZnO shell thickness is each of 120 nm and 200 nm, a partially depleted layer was formed.

For the sake of understanding, the described FIGS. 35A to 35C will be described in other words. Graphs disposed on a top of each of FIGS. 35A to 35C show a band structure in a state that oxygen is adsorbed before the nanostructure is exposed to a reducing gas. FIG. 35A is a view in case that the nanostructure is a CuO nanowire as a comparison group, FIG. 35b is a view in case that the nanostructure is a CuO—ZnO core-shell nanowire on which a fully depleted layer is formed as preferable Specific Example, and FIG. 35C is a view in case that the nanowire is a CuO—ZnO core-shell nanowire on which a partially depleted layer is formed as another Specific Example. In comparison between top graphs of FIGS. 35B and 35C different from each other in fullness of the depletion layer, it has been confirmed that initial resistance shows very high value in FIG. 35B, but shows a relatively low value in FIG. 35C. Next, graphs disposed on a center and a bottom in each of FIGS. 35a to 35C show that all of oxygen ions or molecules adsorbed to a shell surface are detached from the shell surface through a reaction with a reducing gas when a sensor is exposed to the reducing gas, and it has been conformed that a resistance change is induced due to the detachment of the oxygen ions or molecules. In comparison with the graphs, in a case of a sensor in which the shell is formed at a thickness equal to or less than that the fully depleted layer, when the sensor is exposed to an infinitesimal amount of a reducing gas, the sensor shows a large resistance change, so, it has been confirmed that the sensor may be used as a high sensitive sensor.

For example, when a core-shell nanowire in which a fully depleted layer is formed on a shell, is exposed to a CO gas, $CO_2$ molecules are released by interactions between CO molecules and oxygen chemical species chemically adsorbed to a surface. The oxygen species are removed from the surface, emit electrons, and recover their initial band shape. Meanwhile, when a core-shell nanowire in which a partially depleted layer is formed on a shell, is exposed to a CO gas, a resistance change is decreased due to a conduction channel between the depletion layer and the heterojunction of the shell, so that the response is mostly generated due to the depletion layer of the shell. In putting the analysis results together, when the shell thickness about 120 nm and about 200 nm, the shell thickness of about 120 nm and about 200 nm excesses a shell thickness for forming a fully depleted layer on a shell, and in this case, a response with respect to a Co gas was decreased.

Specific Example 2

Preparing of $SnO_2$—ZnO Core-Shell Nanowire 1

A $SnO_2$—ZnO core-shell nanowire was prepared through a novel two-step process like Specific Example 1, and through this, a gas sensor was prepared.

First, a $SnO_2$ core nanowire was synthesized by using an electrospinning method, and then, a ZnO shell layer was deposited by using an ALD method.

Polyvinyl pyrrolidone (PVP) having a molecular weight of 1,300,000 and tin chloride [$SnO_2.2H_2O$] were used as precursor compounds for synthesizing the $SnO_2$ core nanowire. For electrospinning, 1.75 g of tin chloride was mixed with a dimethylformamide (DMF) and ethanol solvent having a volume ratio of 1:1, and the resultant mixture was stirred at a temperature of 70° C. for 30 minutes. PVD beads were dissolved in a solution containing the precursors to prepare 8 weight % of a solution, and the solution ws additionally stirred for 8 hours. The viscous tin chloride/PVA solution is loaded inside a glass syringe provided with a 21-gauge stainless steel needle. The nanowires were uniformly spun on a $SiO_2$ wafer disposed on a metal collector. The electrospun nanowires were calcinated at a temperature of 600° C. for 4 hours, and at this time, a tube-type furnace was used. In order to minimize a loss of a nanowire under the atmosphere in a laboratory, prepared samples were stored in a dust collection mask and under a vacuum before a measurement and a characteristic analysis thereof are performed.

A general ALD method was used in order to form a ZnO shell structure on a surface of the $SnO_2$ nanowire. In the present Specific Example, an ALD system equipped with a horizontal wall reactor, were used. Diethylzinc [$Zn(C_2H_5)_2$, DEZn] and $H_2O$ were used as precursors. In order to prevent a violent pre-reaction between the two precursors, DEZn and $H_2O$ were separately introduced into a growth reactor, and a temperature and a pressure of the growth reactor were 150° C. and 0.3 Torr, respectively. DEZn was stored in a bubbler having a temperature of 0° C., and $H_2O$ was stored in a bubbler having a temperature of 10° C. An ALD pulse length was set to 0.12 seconds with respect to DEZn dosing, 3 seconds with respect to $N_2$ purging, and 0.15 seconds with respect to $H_2O$ dosing, and aforementioned processes correspond to one ALD cycle of are performed. The number of the ALD cycle was adjusted to 30 times, 80 times, 200 times, 350 times, and 650 times. An average diameter of the $SnO_2$ core nanowire was about 90 nm, and a thickness of a ZnO shell layer was adjusted to 20 nm to 90 nm.

<Analysis of CuO—ZnO Core-Shell Nanowire>

Analysis Method

A microstructure and a phase of the core-shell nanowire prepared according to the processes were analyzed by using a field emission scanning electron microscope (FE-SEM), a transmission electron microscope (TEM), and X-ray diffractometer (XRD). Also, an elemental mapping was performed in an energy dispersive spectroscopy EDS) mode.

Meanwhile, in order to measure a sensor response, a sensor including the $SnO_2$—ZnO core-shell nanowire was prepared, and in order to prepare a two-layered electrode of the sensor, Ti and Au were sequentially deposited on a base material at a thickness of about 50 nm and a thickness of about 200 nm, respectively by using a sputtering method and an interdigital electrode mask A sensor response with respect to a reducing gas, CO was measured at a temperature of 300° C. by using a homemade gas and sensing system. A sensitivity S was calculated according to the following Formula. S=Ra/Rg or Rg/Ra (where the Ra corresponds to initial resistance when a gas is not supplied, and the Rg corresponds to resistance when a gas to be measured exists) A vapor content inside a CO container was maintained to 3 ppm or less.

Also, by performing analyses of microstructure, phase, and gas sensitivity of the prepared $SnO_2$—ZnO core-shell nanowire, a thickness effect of the ZnO shell layer on the surface of the $SnO_2$ core nanowire was analyzed, and a heterojunction effect formed on an interface between two different materials was analyzed.

Analysis Results

Figure 36A:
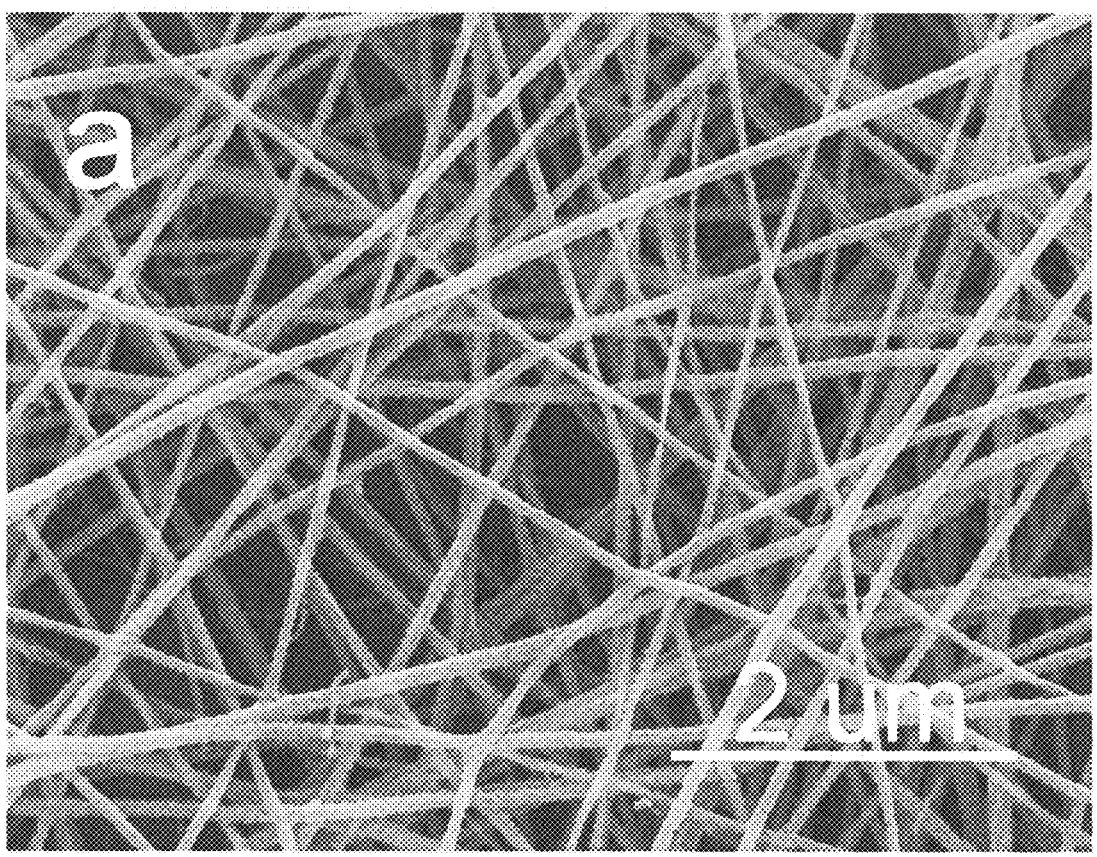
FIG. 36A is a field-emission scanning electron microscope (FE-SEM) image of a $SnO_2$ core nanowire prepared according to Specific Example 1 of the present invention.
Figure 36B:
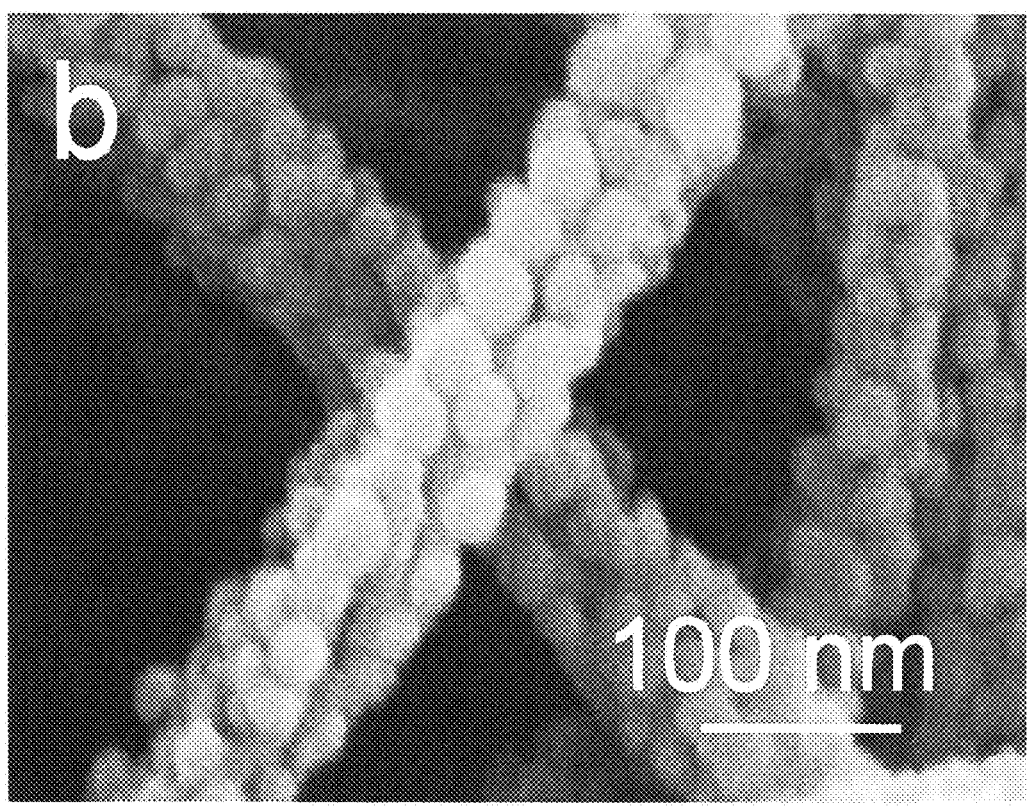
FIG. 36B is an enlarged view of FIG. 36A.
Figure 36C:
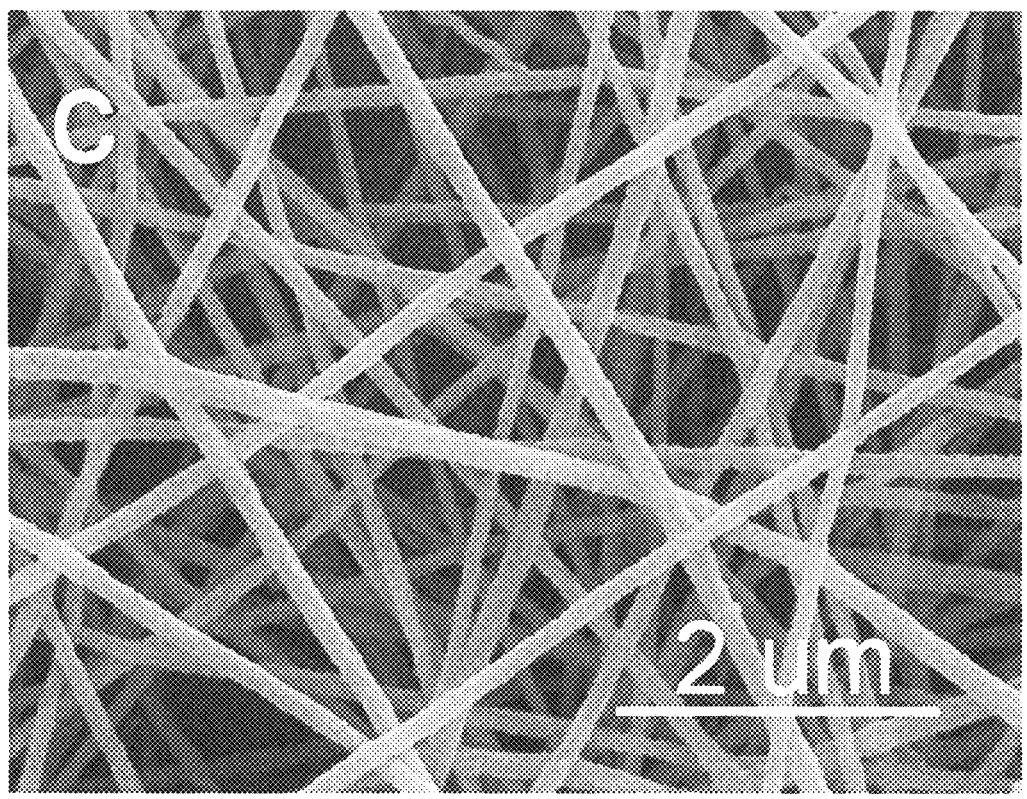
FIG. 36C is a field-emission scanning electron microscope (FE-SEM) image of a $CnO_2$—ZnO core-shell nanowire prepared by changing the number of an ALD cycle.
Figure 36D:
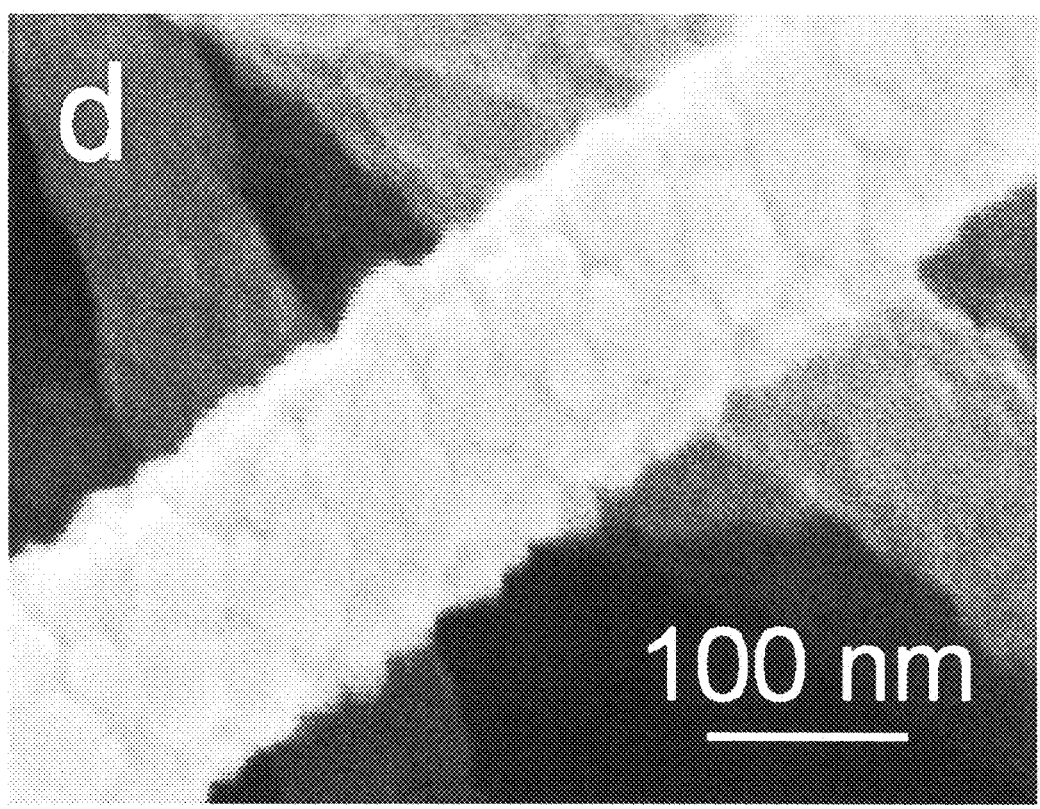
FIG. 36D is a detailed view of FIG. 36C.
Figure 36E:
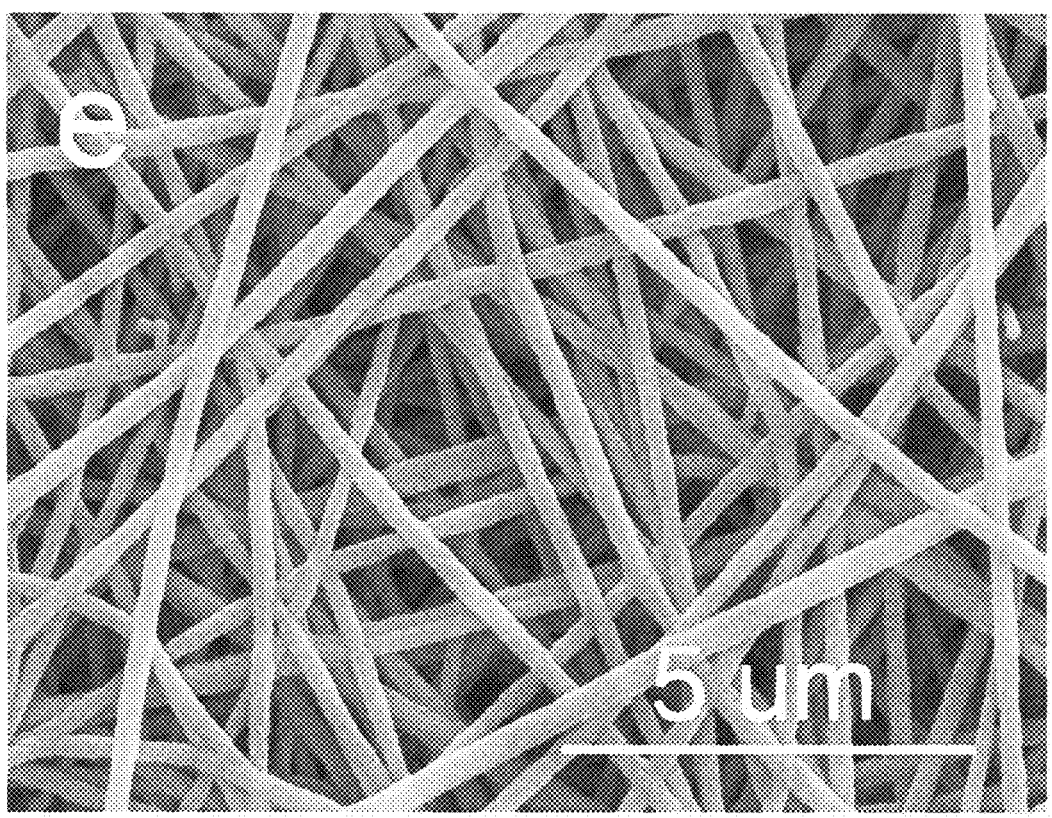
FIG. 36E is a field-emission scanning electron microscope (FE-SEM) image of a $CnO_2$—ZnO core-shell nanowire prepared by changing the number of an ALD cycle.
Figure 36F:
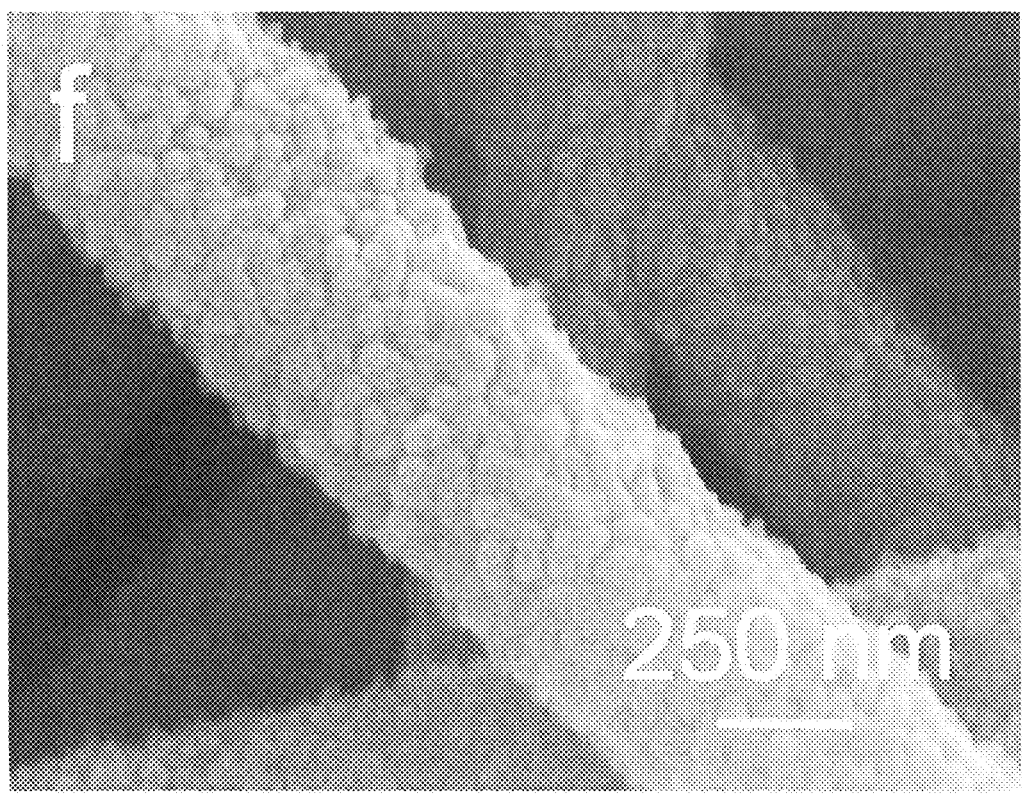
FIG. 36F is a detailed view of FIG. 36E.

First, FIG. 36A is a FE-SEM image of a $SnO_2$ core nanowire, which is discretely dispersed on a $SiO_2$ base material, synthesized through an electrospinning method, and FIG. 36B is an enlarged view of FIG. 36A. Meanwhile, FIGS. 36C and 36E are FE-SEM images of a $SnO_2$—ZnO core-shell nanowire prepared by increasing the number of an ALD cycle, the ALD cycle was repeated 80 times in FIG. 36C, the ALD cycle was repeated 350 times in FIG. 36D, and it has been confirmed that as the number of the ALD cycle is increased, a ZnO shell thickness is gradually increased. Meanwhile, FIG. 36D is an enlarged FE-SEM image of FIG. 36C, FIG. 36F is is an Enlarged FE-SEM image of FIG. 36E, and through this, it has been apparently confirmed that the $SnO_2$—ZnO core-shell nanowire includes a nano-sized particles. Referring to the views, large size particle forming the $SnO_2$ core nanowire, and small size particles forming the ZnO shell layer deposited on the $SnO_2$ core nanowire were apparently distinguished. It is estimated that Particles on the shell layer protrude from a surface thereof to form a rough surface, the rough surface provides an adsorption space when gas molecules are introduced, and thus the rough surface may improve adsorption performance of the sensor. Meanwhile, the heterojunction, which is formed between two different materials, generated a potential barrier on an interface of the two different materials, and formed a path through which electrons penetrate to improve a gas sensitivity.

Figure 37A:
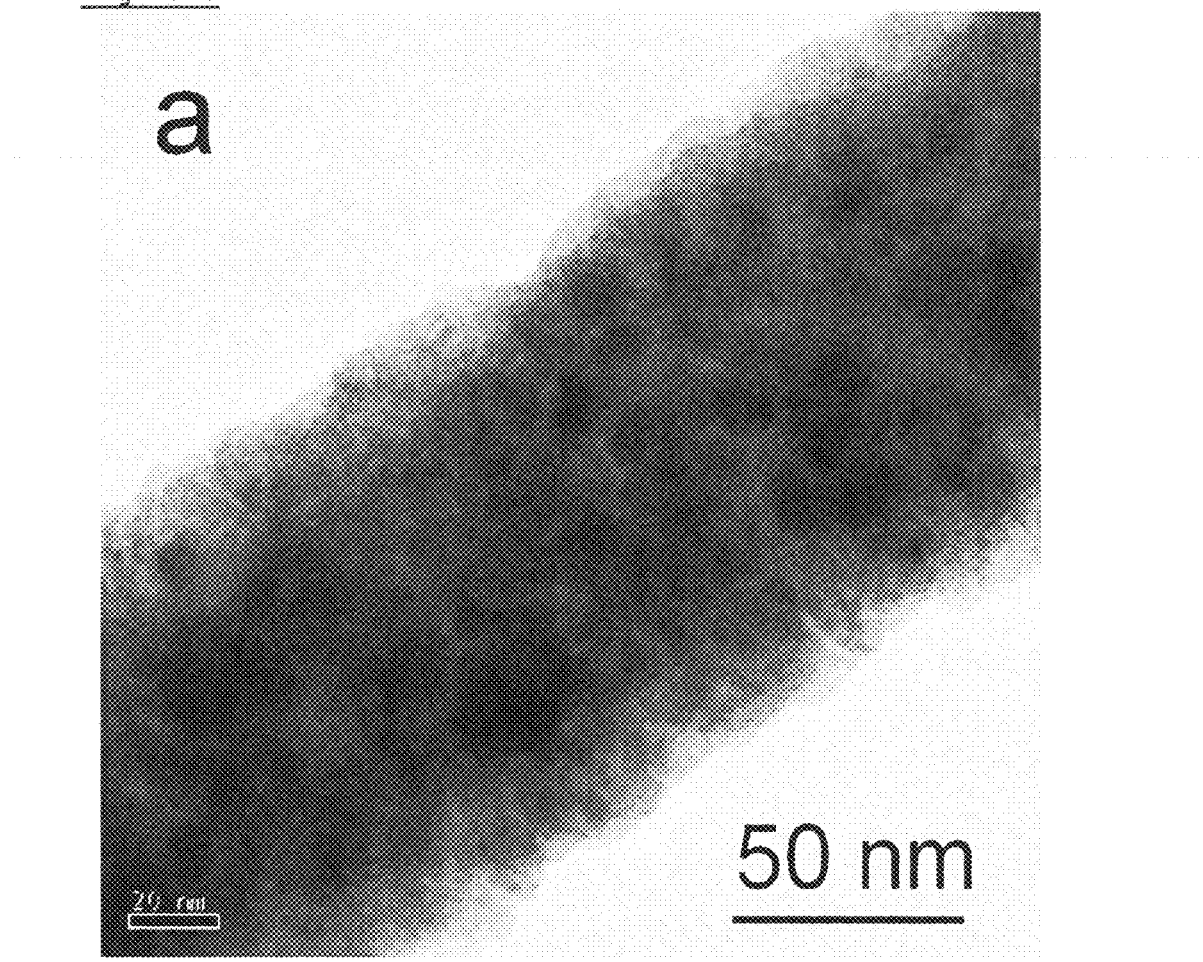
FIG. 37A is a low magnification transmission electron microscope image of a core-shell nanowire having a ZnO shell thickness of 20 nm, which is prepared according to Specific Example 1 of the present invention.
Figure 37B:
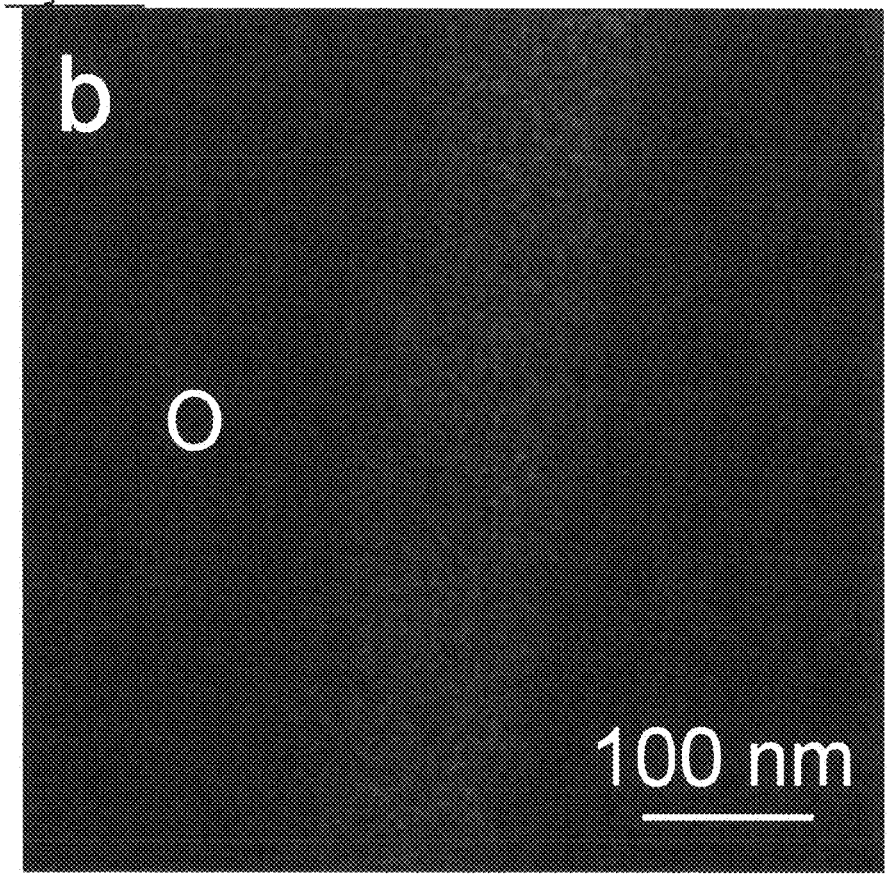
FIG. 37B is an elemental mapping profiles of O of the core-shell nanowire.
Figure 37C:
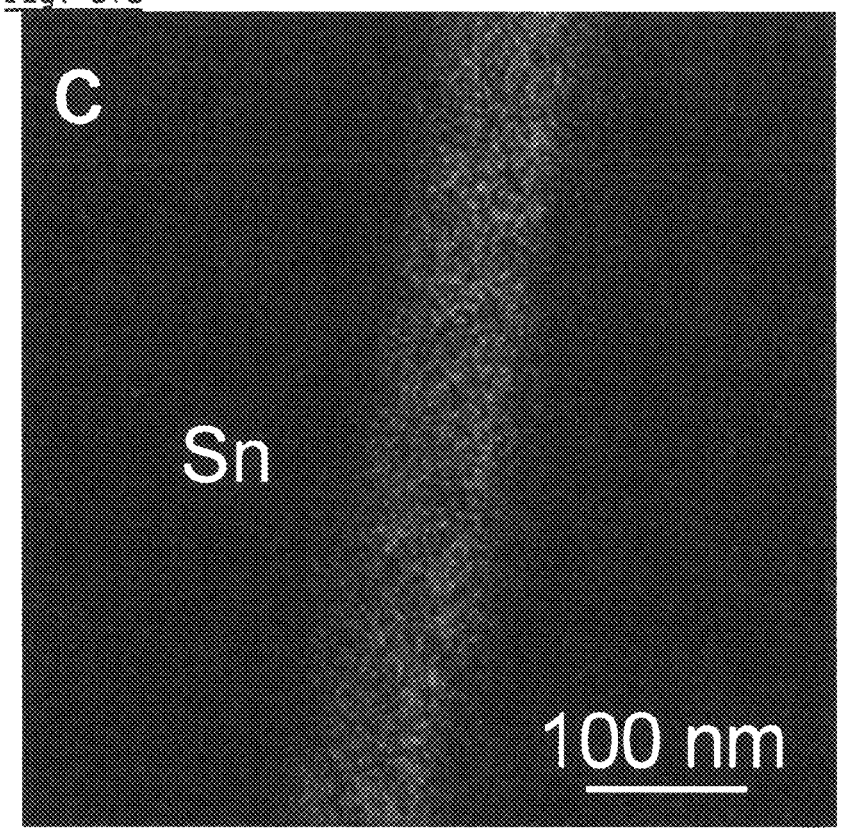
FIG. 37C is an elemental mapping profiles of Sn of the core-shell nanowire.
Figure 37D:
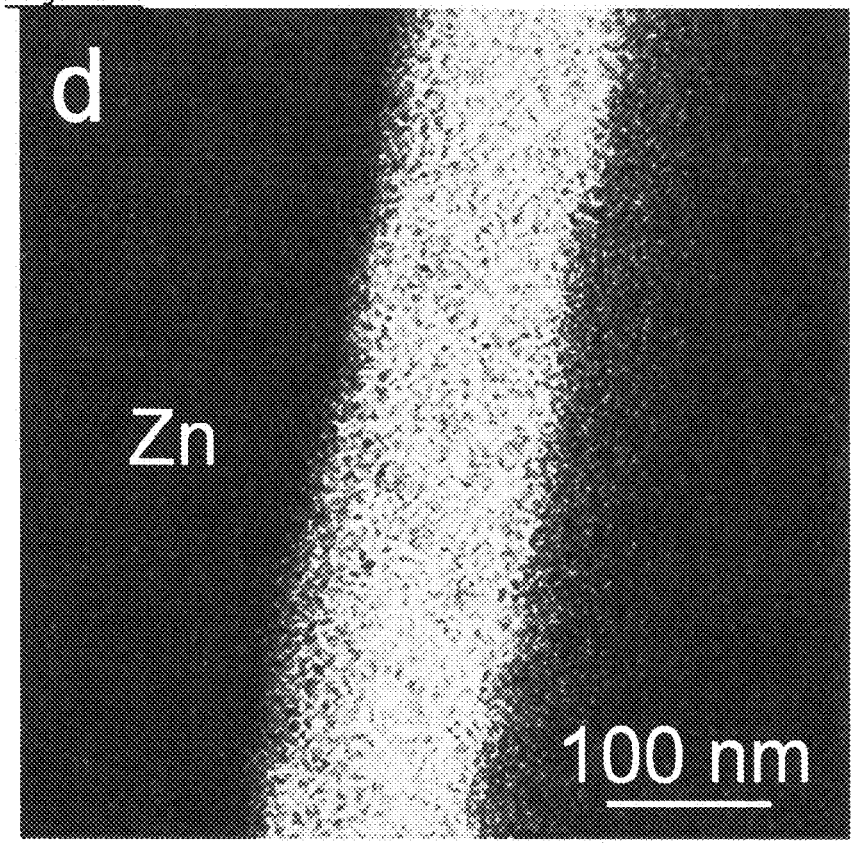
FIG. 37D is an elemental mapping profiles of Zn of the core-shell nanowire.
Figure 37E:
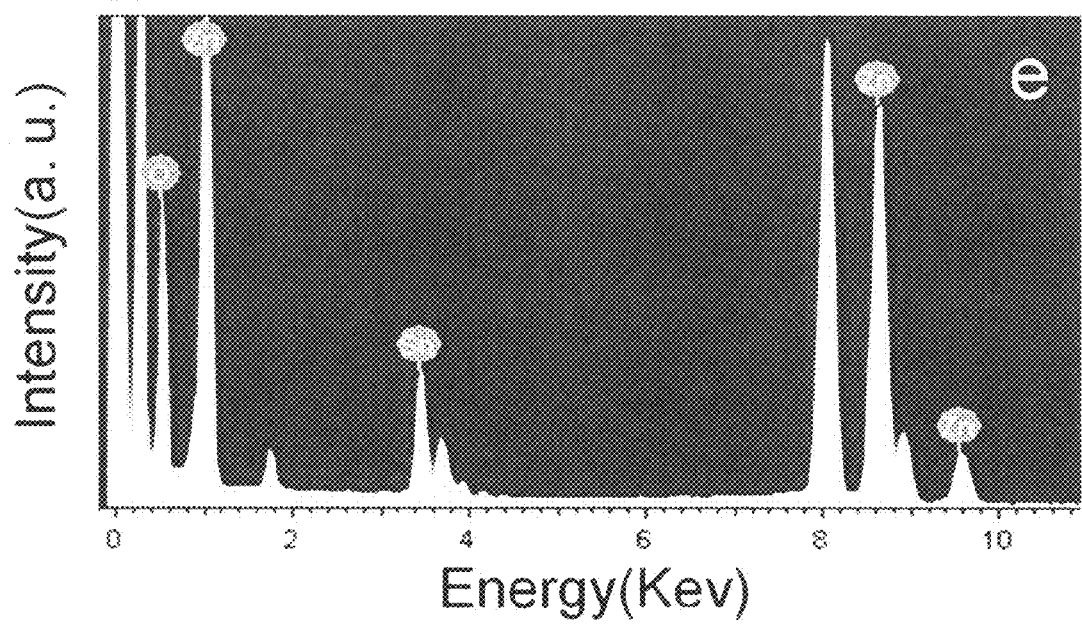
FIG. 37E is a graph showing a chemical composition of the core-shell nanowire analyzed by using an energy-dispersive spectroscopy (EDS)

The microstructure of the core-shell nanowire was additionally analyzed by using a TEM. FIG. 37A is a low magnification TEM image of a core-shell nanowire having a ZnO shell thickness of 20 nm. FIGS. 37B and 37D are elemental mapping profiles of O, Sn, and Zn of the $SnO_2$—ZnO core-shell nanowire, respectively, and FIG. 37E is a graph showing a chemical composition of the $SnO_2$—ZnO core-shell nanowire analyzed by using an EDS. It has been confirmed that in the core-shell nanowire, Zn is concentrated on an outer surface of the nanowire, and Su is concentrated inside the nanowire through results of FIGS. 37A to 37E, and accordingly, it has been confirmed that elements, such as O, Sn, and Zn are apparently spatially separated. It has been confirmed from the elemental mapping analysis results that a core-shell nanowire having a shell thickness of 20 nm is formed, and it has been confirmed from the EDS analysis results that ZnO exists on a surface of the core-shell nanowire, and $SnO_2$ exists in a core.

FIG. 38 shows XRD patterns of a $SnO_2$ nanowire and a $SnO_2$—ZnO core-shell nanowire. The XRD pattern of the $SnO_2$ nanowire was confirmed for the sake of comparison. $SnO_2$—ZnO core-shell nanowires, which have shell thicknesses of 20 nm and 90 nm, respectively, showed a diffraction peak corresponding to a ZnO phase in addition to a peak by a $SnO_2$ phase, and from this, it has been again confirmed that the ZnO shell layer is formed on the $SnO_2$ core nanowire. Increased intensity of the XRD peak was proportional to an increased thickness of the ZnO shell layer formed on a surface of the $SnO_2$ nanowire.

Figure 39A:
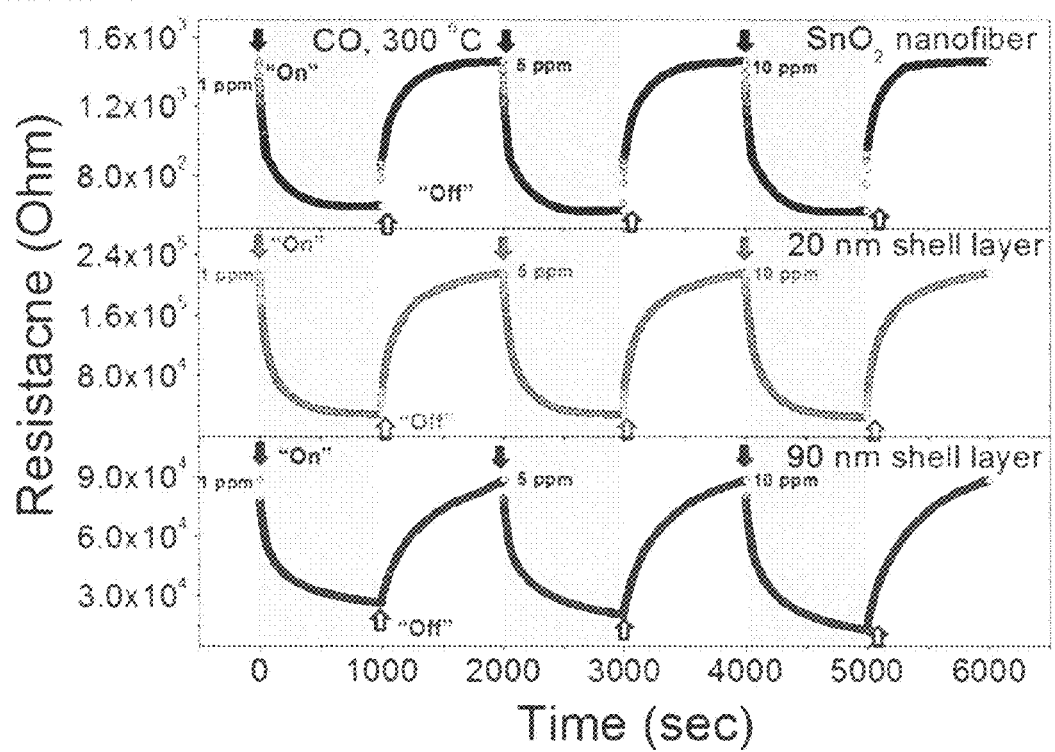
FIG. 39A shows response curves to a CO gas of each of a $SnO_2$—ZnO core-shell nanowire prepared so as to have various thicknesses according to Specific Example 1 of the present invention, and a comparison group of a $SnO_2$ nanowire.

In order to confirm sensitivities with respect to respective gases in the $SnO_2$ nanowire and the $SnO_2$—ZnO core-shell nanowires having various thicknesses, the experimental was performed under an atmosphere of a concentration of 1 ppm to 10 ppm of CO. All sensor responses showed according to a concentration change of CO. FIG. 39A is a graph showing response curves to a CO gas at a temperature of 300° C. of sensors including a $SnO_2$ nanowire and a $SnO_2$—ZnO core-shell nanowire, respectively.

Figure 39B:
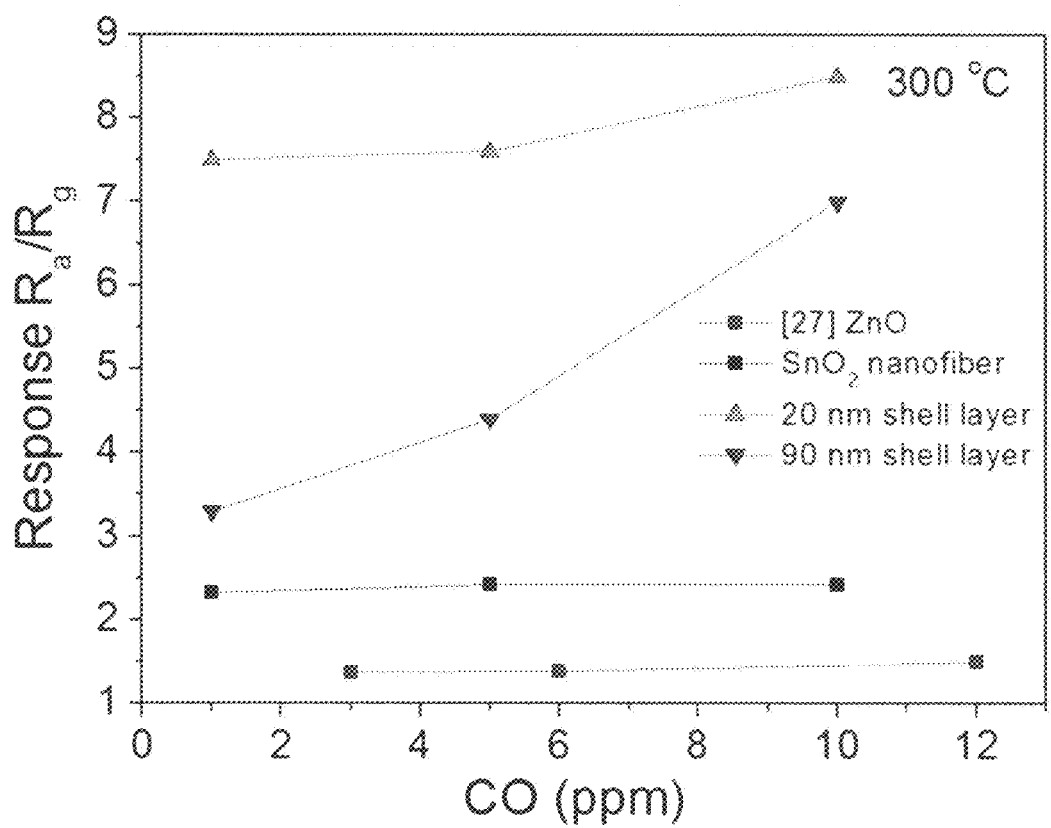
FIG. 39B shows response curves to a CO gas of each of a $SnO_2$—ZnO core-shell nanowire prepared so as to have various thicknesses according to Specific Example 1 of the present invention, and a comparison group of a $SnO_2$ nanowire.
Figure 39C:
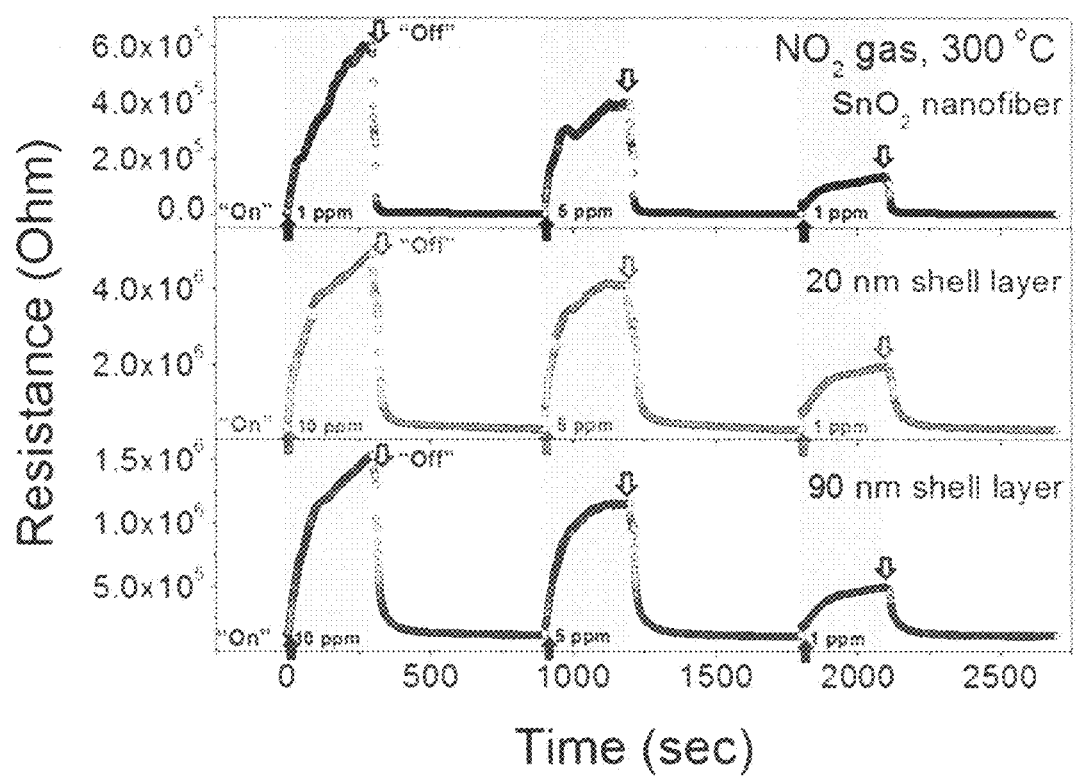
FIG. 39C shows response curves to a $NO_2$ gas of each of the $SnO_2$—ZnO core-shell nanowire prepared so as to have various thicknesses according to Specific Example 1 of the present invention, and the comparison group of the $SnO_2$ nanowire.
Figure 39D:
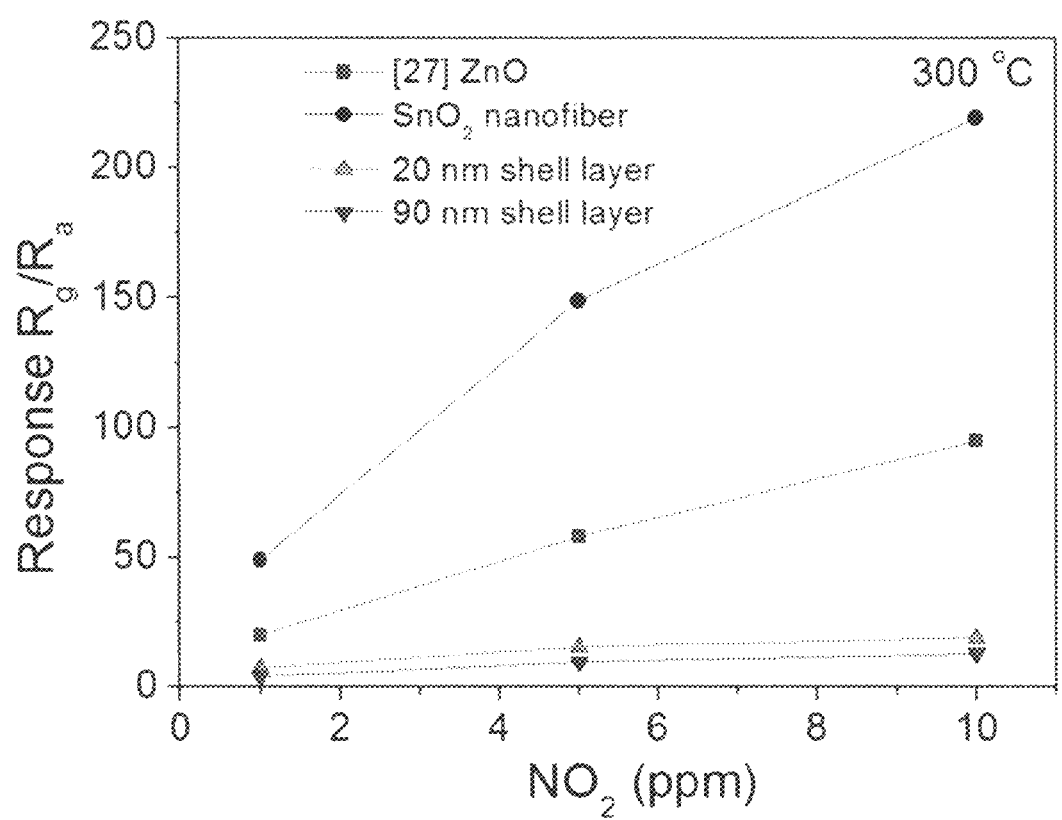
FIG. 39D shows response curves to a $NO_2$ gas of each of the $SnO_2$—ZnO core-shell nanowire prepared so as to have various thicknesses according to Specific Example 1 of the present invention, and the comparison group of the $SnO_2$ nanowire.
Figure 39E:
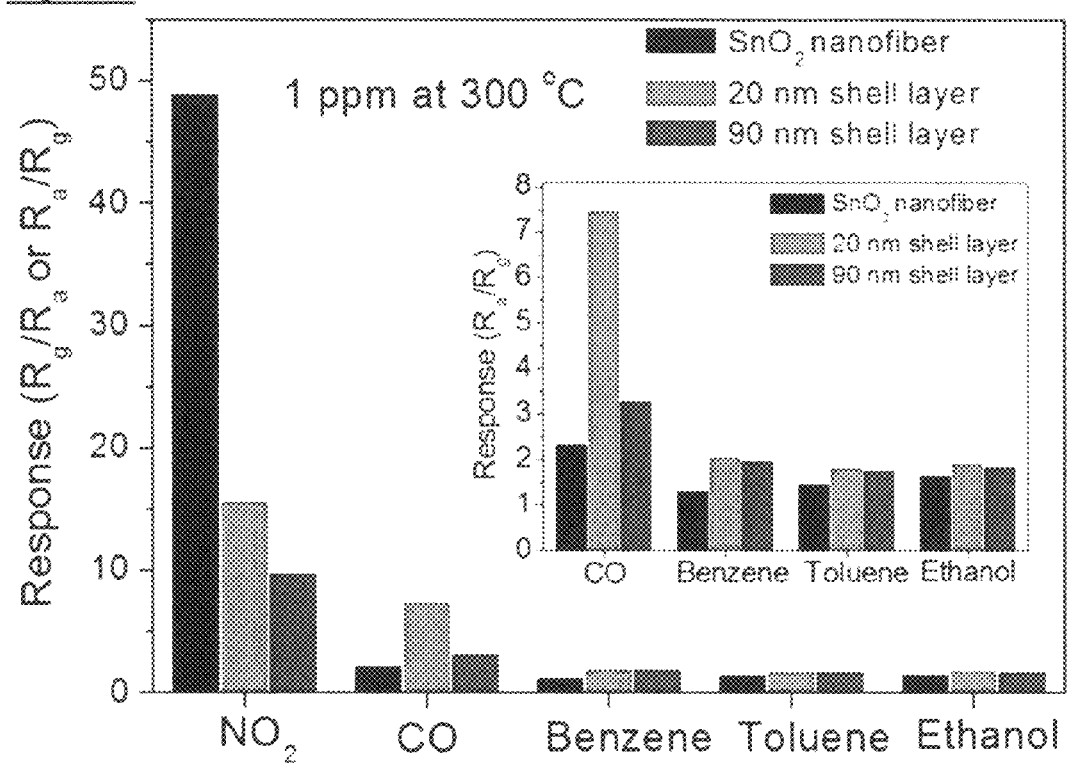
FIG. 39E expresses the results of FIGS. 39A to 39D in one graph.

When the core-shell nanowire is exposed to a CO gas, CO gas molecules produce the following reaction with oxygen adsorbed to a surface of ZnO: [CO+$O_2^-$→$CO_2$+2$e^-$]. Therefore, free electrons reduce resistance. Meanwhile, when the supply of the CO gas is cut off, oxygen molecules in the atmosphere are adsorbed to a surface of a nanowire, and accordingly, resistance is increased due to the electron adsorption of the nanowire. FIG. 39B relates to a relative response of the core-shell nanowire. The sensor including a core-shell nanowire having a shell thickness of about 20 nm showed a response about 7.5, about 7.6, and about 8.5 with respect to a concentration of 10 ppm of CO, and in the sensor including a core-shell nanowire having a shell thickness of about 90 nm, a response is reduced to 3.3, 4.4, and 7. It has been shown that a reducing gas detection response is reduced in a shell thickness of a Debye length or more, but this shows an improved response compared to a sensor including a pure $SnO_2$ nanowire and a pure ZnO nanowire. When the shell thickness of the core-shell nanowire is equal to or less than a Debye length, gas particles may extract electrons from a core. When the shell thickness of the core-shell nanowire is 10 nm or less, a p-type response appeared, but when the shell thickness excesses 10 nm, an n-type response appeared. The all analysis results described above supported that the ZnO shell thickness in the core-shell nanowire functioned as a major factor in response of the sensor. Meanwhile, FIGS. 39C and 39D are different from FIGS. 39A and 39D in that a response not with respect to a CO gas but with respect to a $NO_2$ gas is measured. Also, FIGS. 39E and 39F show, in one graph, results of FIGS. 39A and 39B related to a response to a CO gas and FIGS. 39C and 39D related to a response with respect to a $NO_2$ gas, and show such that responses with respect to different gases are seen at a single glance.

Figure 40A:
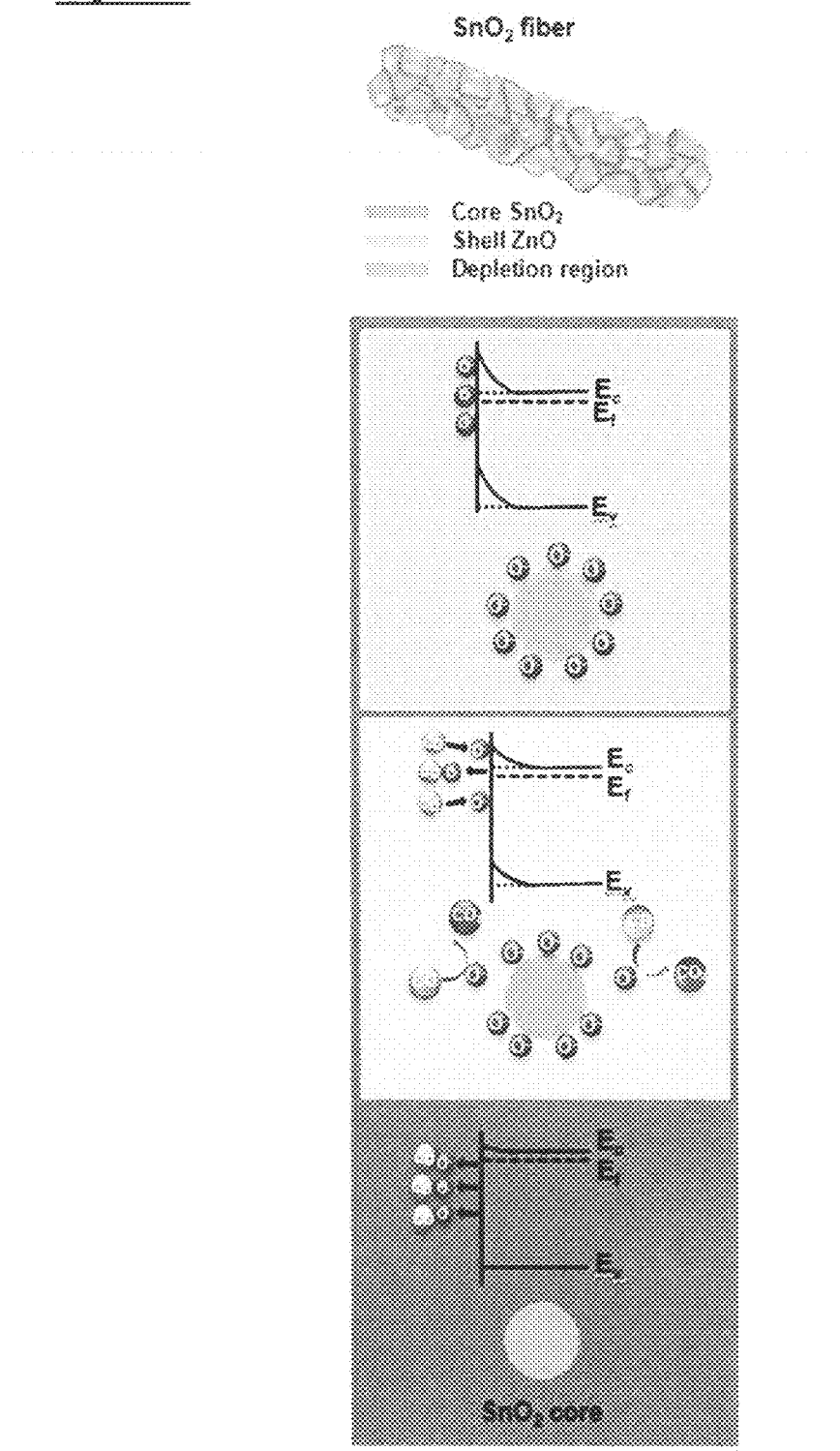
FIG. 40A is a schematic view illustrating a nanostructure prepared according to Specific Example 1 of the present invention so as to be used as a sensing part of a sensor, in which an electron transfer, a conduction band energy level EC, and a Fermi energy level EF are schematically illustrated, and in particular, FIG. 40A corresponds to a case that the nanostructure is a comparison group of a $SuO_2$ nanowire.
Figure 40B:
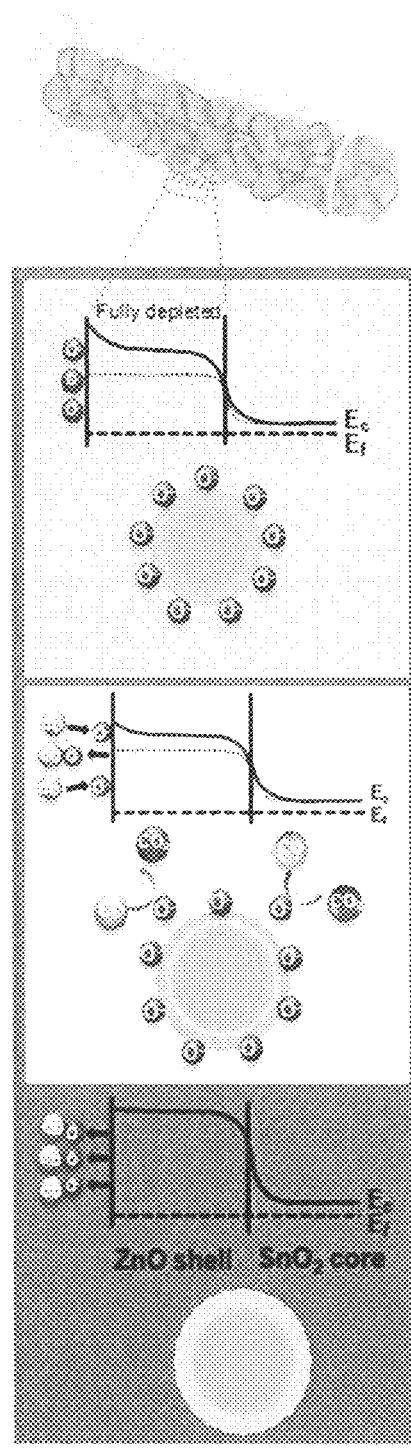
FIG. 40B is a schematic view illustrating a nanostructure prepared according to Specific Example 1 of the present invention so as to be used as a sensing part of a sensor, in which an electron transfer, a conduction band energy level EC, and a Fermi energy level EF are schematically illustrated, and in particular, FIG. 40B corresponds to a case that the nanostructure is a $SnO_2$—ZnO core-shell nanowire in which a fully depleted layer is formed.
Figure 40C:
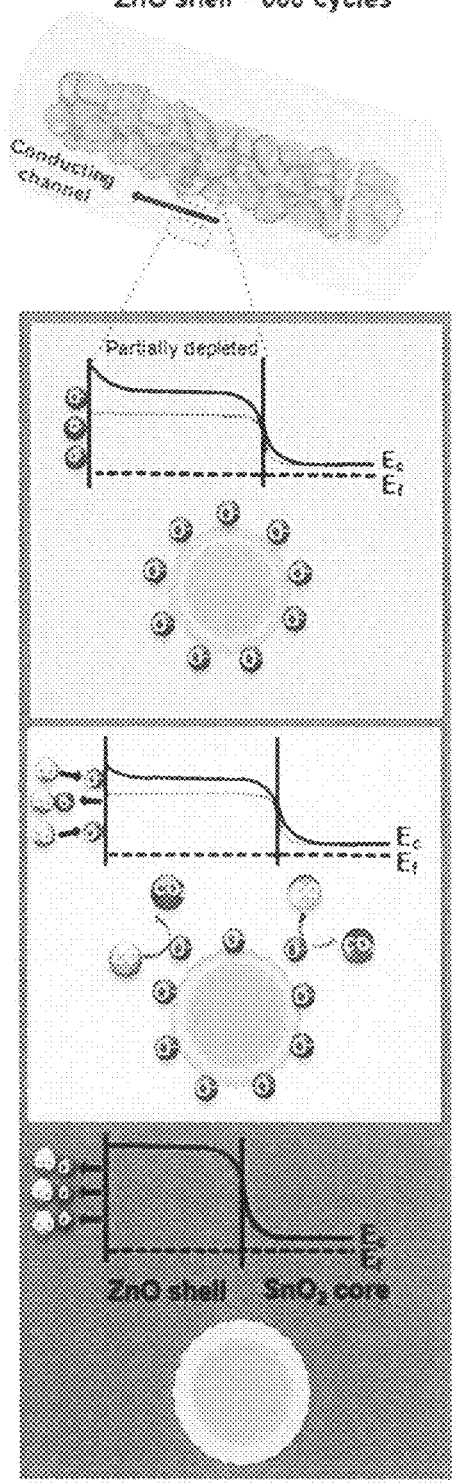
FIG. 40C is a schematic view illustrating a nanostructure prepared according to Specific Example 1 of the present invention so as to be used as a sensing part of a sensor, in which an electron transfer, a conduction band energy level EC, and a Fermi energy level EF are schematically illustrated, and in particular, FIG. 40C corresponds to a case that the nanostructure is a $SnO_2$—ZnO core-shell nanowire in which an partially depleted layer is formed, respectively.

A response mechanism with the respect to a gas in the core-shell nanowire is related to a depletion layer formed on the shell layer due to electron adsorption of a gaseous chemical species chemically adsorbed and a heterojunction formed between the shell layer and the core nanowire. In this regard, FIGS. 40A to 40C are schematic views illustrating a nanostructure prepared according to the present Specific Example so as to be used as a sensing part of a sensor, and schematic views illustrating an electron transfer, a conduction band energy level EC, and a Fermi energy level EF, in case that the nanostructure is a comparison group of a $SnO_2$ nanowire, in case that the nanostructure is a $SnO_2$—ZnO core-shell nanowire in which a fully depleted layer is formed, and in case that the nanostructure is a $SnO_2$—ZnO core-shell nanowire in which a partially depleted layer is formed, respectively. In a core-shell nanowire having a shell thickness of 10 nm, adsorption of oxygen molecules occurred on all surfaces of a ZnO shell layer and a $SnO_2$ surface, and it has been estimated that oxygen molecules may be diffused along a channel formed between small particles of the ZnO shell layer. FIG. 40A showed a relative band bending. Meanwhile, in a core-shell nanowire having a shell thickness of 50 nm, a fully depleted layer was formed on the shell layer by complex effects such as a band bending on a surface of the ZnO shell layer due to adsorption of an oxygen chemical species and a band bending on a heterojunction formed between the ZnO shell layer and the $SnO_2$ core nanowire. Under the atmosphere, inner defects such as oxygen vacancy on a surface of the n-type ZnO shell layer, is utilized as an adsorption site of oxygen molecules. Free electrons inside the ZnO shell layer are removed by the adsorbed oxygen molecules through the following reaction: [$O_2$(g)+$e^-$→$O_2^-$ (Adsorption)]. Reduction under free charge density inside the ZnO shell depletes a surface charge state, and generates a space charge region. Resultantly, the band bending occurs on a surface of the ZnO shell layer. A thickness of a depletion layer by the adsorption described in Specific Example 1, which is calculated by Mathematical Equation 1, was about 69 nm. Mathematical Equation may 1 be again written as described below for convenience for description.

$$d = \sqrt{\frac{2\varepsilon_{ZnO}\varepsilon_0 \Phi_S}{e^2 N_D^+(T)}} \quad \text{[Mathematical Equation 1]}$$

In the Mathematical Equation 1, $\varepsilon_{ZnO}$ is a relative dielectric constant value, in which the value is about 8.7, $\varepsilon_0$ is permittivity of vacuum, e is an electronic charge, ND+(T) is a donor concentration at room temperature, in which the concentration is about 1017 $cm^{-3}$, and $\Phi$ is a potential barrier height, in which the value is 0.5 eV.

ZnO—$SnO_2$ is a p-n isotope heterojunction. The band bending inside the ZnO—$SnO_2$ hetero structure may be evaluated on the basis of an energy band structure thereof. Electron affinity ($\chi$), a band gap (Eg)m and a work function (W) of ZnO and $SnO_2$ are required for analyzing an energy band structure, and $\chi$ZnO and $\chi SnO_2$ are 4.29 eV and 4.07 eV, respectively, Eg, ZnO and Eg, $SnO_2$ are 3.3 eV and 1.35 eV, respectively, and WZnO and W$SnO_2$ are 4.45 eV and 5.2 eV, respectively. A band bending occurs while a heterojunction between ZnO and $SnO_2$ is formed, and the results are schematically shown on a bottom of FIGS. 40B and 40C. In this case, a difference between WZnO and W$SnO_2$ caused a built-in-potential on an interface between ZnO and $SnO_2$, and the built-in potential was 0.75 eV. A depletion layer with (Wd) in the heterojunction may be calculated from Mathematical Equation q by substituting the built-in potential of 0.75 eV for $\Phi$s. The calculated Wd was about 85 nm. Resultantly, as schematically illustrated in FIGS. 40B and 40C, widths of the depletion layers, which are formed on a surface and a heterojunction, are substantially about 69 nm and 85 nm, respectively, and when the ZnO shell thickness is up to 50 nm, a fully depleted layer was formed, and when the ZnO shell thickness is each of 120 nm and 200 nm, a partially depleted layer was formed.

When a core-shell nanowire in which a fully depleted layer is formed on a shell, is exposed to a CO gas, $CO_2$ molecules are released by interactions between CO molecules and oxygen chemical species chemically adsorbed to a surface. The oxygen species are removed from the surface, emit electrons, and recover their initial band shape. Meanwhile, when a core-shell nanowire in which a partially depleted layer is formed on a shell, is exposed to a CO gas, a resistance change is decreased due to a conduction channel between the depletion layer and the heterojunction of the shell, so that the response is mostly generated due to the depletion layer of the shell. In putting the analysis results together, when the shell thickness about 120 nm and about 200 nm, the shell thickness of about 120 nm and about 200 nm excesses a shell thickness for forming a fully depleted layer on a shell, and in this case, a response with respect to a Co gas was decreased.

The description of the present invention is provided only for illustration, and it will be understood that by those of ordinary skill in the art that various changes in form and details may be made therein without departing from the substantial features of the embodiments. Thus, the above embodiments should be construed to be exemplary rather than as limitative. For example, any elements described herein as singular can be pluralized, and plural elements can be used in the singular.

The scope of the invention is defined not by the detailed description of the invention but by the appended claims, and all modifications or modified forms deduced from meaning, scope, and equivalent concept will be construed as being included in the scope of the present invention.

The invention claimed is:

1. A method for preparing a sensor, the method comprising:

forming a core of an n-type oxide semiconductor nanowire on a base material;

forming a shell of a plurality of discrete n-type oxide semiconductor nano islands on the core to form a sensing part including a core-shell nanostructure; and forming a substantially planar electrode layer comprising two electrodes spaced apart from each other on the sensing part, wherein the shell has a thickness of a Debye length or less such that a fully depleted layer is formed throughout the entire shell, wherein the n-type oxide semiconductor of the plurality of discrete nano islands and the n-type oxide semiconductor of the nanowire have different work functions from each other, and when a work function of the n-type oxide semiconductor of the plurality of discrete nano islands is greater than that of the n-type oxide semiconductor of the nanowire, the sensor senses a reducing gas; and when a work function of the n-type oxide semiconductor of the plurality of discrete nano islands is smaller than that of the n-type oxide semiconductor of the nanowire, the sensor senses an oxidizing gas.

* * * * *